(12) United States Patent
Fallin et al.

(10) Patent No.: US 9,265,498 B2
(45) Date of Patent: Feb. 23, 2016

(54) COMPACT LINE LOCKS AND METHODS

(71) Applicant: IMDS LLC, Providence, UT (US)

(72) Inventors: T. Wade Fallin, Hyde Park, UT (US); M. Mary Sinnott, Logan, UT (US)

(73) Assignee: IMDS LLC, Providence, UT (US)

( * ) Notice: Subject to any disclaimer, the term of this patent is extended or adjusted under 35 U.S.C. 154(b) by 353 days.

(21) Appl. No.: 13/758,171

(22) Filed: Feb. 4, 2013

(65) Prior Publication Data

US 2013/0165973 A1   Jun. 27, 2013

Related U.S. Application Data

(63) Continuation of application No. 12/754,774, filed on Apr. 6, 2010, now Pat. No. 8,388,655, which is a continuation of application No. 11/125,885, filed on May 9, 2005, now Pat. No. 7,722,644, which is a continuation-in-part of application No. 10/459,375, filed on Jun. 11, 2003, now Pat. No. 7,150,757, and a continuation-in-part of application No. 10/936,376, filed on Sep. 7, 2004, now Pat. No. 7,566,339, and a continuation-in-part of application No. 10/942,275, filed on Sep. 15, 2004, now Pat. No. 7,806,909, and a continuation-in-part of application No. 11/001,866, filed on Dec. 1, 2004, now Pat. No. 7,594,923.

(51) Int. Cl.
| | | |
|---|---|---|
| *A61B 17/04* | (2006.01) | |
| *A61B 17/82* | (2006.01) | |
| *A61B 17/58* | (2006.01) | |
| *F16G 11/00* | (2006.01) | |

(52) U.S. Cl.
CPC ......... *A61B 17/0487* (2013.01); *A61B 17/0401* (2013.01); *A61B 2017/0404* (2013.01); *A61B 2017/0458* (2013.01); *A61B 2017/0459* (2013.01); *Y10T 24/3916* (2015.01)

(58) Field of Classification Search
CPC ........... A61B 17/0401; A61B 17/0487; A61B 2017/0404; A61B 2017/0458; A61B 2017/0459; Y10T 24/3916
See application file for complete search history.

(56) References Cited

U.S. PATENT DOCUMENTS

| | | | |
|---|---|---|---|
| 65,499 | A | 6/1867 | Miller |
| 678,533 | A | 7/1901 | Bancker |

(Continued)

FOREIGN PATENT DOCUMENTS

| | | |
|---|---|---|
| CN | 1173119 | 2/1998 |
| CN | 1988859 | 6/2007 |

(Continued)

OTHER PUBLICATIONS

Biomet Orthopedics; Comprehensive Fracture Stem, Surgical Technique Brochure. pp. 1-14.

*Primary Examiner* — Julian W Woo

(74) *Attorney, Agent, or Firm* — Maywood IP Law; G. Jo Hays; David W. Meibos

(57) ABSTRACT

A line lock includes a body at least partially bounding two passageways that cooperate to receive a locking portion of a line such as a suture in such a manner that the locking portion can only be drawn through the passageways along one direction. A second suture locking portion may also be received by the passageways, or by one of the two passageways in combination with a third passageway. The body may have an elongated, compact shape that is easily implantable in the body.

24 Claims, 57 Drawing Sheets

(56) References Cited

U.S. PATENT DOCUMENTS

| | | | |
|---|---|---|---|
| 757,820 A * | 4/1904 | Lykke | 24/130 |
| 904,747 A | 11/1908 | Anderson | |
| 1,083,958 A | 1/1914 | Bromfield | |
| 1,205,496 A | 11/1916 | Whitehead | |
| 1,421,026 A | 6/1922 | Regan | |
| 1,452,338 A | 4/1923 | Flowers | |
| 1,565,041 A | 12/1925 | Arney | |
| 1,610,309 A | 12/1926 | Niederer | |
| 1,713,106 A | 5/1929 | Ulfers | |
| 1,782,625 A | 11/1930 | Neuberger | |
| 1,806,162 A * | 5/1931 | Paul | 24/712.6 |
| 2,025,663 A | 12/1935 | Iuliano | |
| 2,169,528 A | 8/1939 | Heffron | |
| 2,441,336 A | 5/1948 | Sova | |
| 2,543,056 A | 2/1951 | Pollack | |
| 3,165,080 A | 1/1965 | Castelletti | |
| 3,168,850 A | 2/1965 | Tennican | |
| 3,309,745 A | 3/1967 | Gintz | |
| 3,332,118 A | 7/1967 | Temple | |
| 3,399,432 A | 9/1968 | Merser | |
| 3,409,014 A | 11/1968 | Shannon | |
| 3,440,984 A | 4/1969 | Hofe | |
| 3,675,276 A | 7/1972 | Nuse | |
| 3,678,543 A | 7/1972 | Hobbs | |
| 3,699,969 A | 10/1972 | Allen | |
| 3,715,782 A | 2/1973 | Newell | |
| 3,785,009 A | 1/1974 | Nysten | |
| 3,857,645 A | 12/1974 | Klein | |
| 3,880,166 A | 4/1975 | Fogarty | |
| 3,910,281 A | 10/1975 | Kletschka | |
| 3,976,079 A | 8/1976 | Samuels | |
| 3,993,076 A | 11/1976 | Fogarty | |
| 4,034,443 A | 7/1977 | Turner | |
| 4,034,850 A | 7/1977 | Mandel | |
| 4,105,349 A | 8/1978 | Kupperman | |
| 4,280,435 A | 7/1981 | Loomis | |
| 4,296,698 A | 10/1981 | Davidson | |
| 4,439,079 A | 3/1984 | Losada | |
| 4,477,947 A | 10/1984 | Lyons | |
| 4,479,271 A | 10/1984 | Bolesky | |
| 4,480,357 A | 11/1984 | Cummins | |
| 4,480,358 A | 11/1984 | Barling | |
| 4,502,161 A | 3/1985 | Wall | |
| 4,596,329 A | 6/1986 | Eldridge, Jr. | |
| 4,627,853 A | 12/1986 | Campbell | |
| 4,646,394 A | 3/1987 | Krauss | |
| 4,649,664 A | 3/1987 | Mahan | |
| 4,673,407 A | 6/1987 | Martin | |
| 4,721,103 A | 1/1988 | Freedland | |
| 4,723,634 A | 2/1988 | Fisk | |
| 4,773,910 A | 9/1988 | Chen | |
| 4,785,509 A | 11/1988 | Fisher | |
| 4,790,850 A | 12/1988 | Dunn et al. | |
| 4,823,794 A | 4/1989 | Pierce | |
| 4,831,692 A | 5/1989 | Chuan | |
| 4,910,834 A | 3/1990 | Minkler | |
| 4,910,934 A | 3/1990 | Hennings | |
| 4,927,421 A | 5/1990 | Goble | |
| 4,932,962 A | 6/1990 | Yoon | |
| 4,946,377 A | 8/1990 | Kovach | |
| 4,950,270 A | 8/1990 | Bowman | |
| 4,976,013 A | 12/1990 | Wax | |
| 5,030,228 A | 7/1991 | Wong | |
| 5,035,699 A | 7/1991 | Coates | |
| 5,037,439 A | 8/1991 | Albrektsson | |
| 5,067,964 A | 11/1991 | Richmond | |
| 5,074,874 A | 12/1991 | Yoon | |
| 5,092,895 A | 3/1992 | Albrektsson | |
| 5,098,433 A | 3/1992 | Freedland | |
| 5,100,409 A | 3/1992 | Coates | |
| 5,119,539 A * | 6/1992 | Curry | 24/712.1 |
| 5,123,913 A | 6/1992 | Wilk | |
| 5,139,520 A | 8/1992 | Rosenberg | |
| 5,156,616 A | 10/1992 | Meadows | |
| 5,176,684 A | 1/1993 | Ferrante | |
| 5,201,760 A | 4/1993 | West | |
| 5,205,687 A | 4/1993 | Boyland | |
| 5,210,911 A | 5/1993 | Brown | |
| 5,217,470 A | 6/1993 | Weston | |
| 5,261,343 A | 11/1993 | Elterman | |
| 5,284,485 A | 2/1994 | Kammerer | |
| 5,306,301 A | 4/1994 | Graf et al. | |
| 5,307,751 A | 5/1994 | Shell | |
| 5,320,626 A | 6/1994 | Schmieding | |
| 5,350,383 A | 9/1994 | Schmieding | |
| 5,366,327 A | 11/1994 | Nelson | |
| 5,366,480 A | 11/1994 | Corriveau | |
| 5,374,269 A | 12/1994 | Rosenberg | |
| 5,376,126 A | 12/1994 | Lin | |
| D356,154 S | 3/1995 | Ferragamo | |
| 5,403,330 A | 4/1995 | Tuason | |
| 5,445,167 A | 8/1995 | Yoon | |
| 5,454,821 A | 10/1995 | Harm | |
| 5,456,721 A | 10/1995 | Legrand | |
| 5,464,427 A | 11/1995 | Curtis | |
| 5,489,311 A | 2/1996 | Cipolletti | |
| 5,527,341 A | 6/1996 | Gogolewski | |
| 5,562,668 A | 10/1996 | Johnson | |
| 5,569,259 A | 10/1996 | Ferrante | |
| 5,572,770 A | 11/1996 | Boden | |
| D376,095 S | 12/1996 | Curtis | |
| 5,582,288 A | 12/1996 | Zatarga | |
| 5,584,835 A | 12/1996 | Greenfield | |
| 5,593,411 A | 1/1997 | Stalcup | |
| 5,601,557 A | 2/1997 | Hayhurst | |
| 5,607,430 A | 3/1997 | Bailey | |
| 5,625,925 A | 5/1997 | Richards | |
| 5,630,824 A | 5/1997 | Hart | |
| 5,632,745 A | 5/1997 | Schwartz | |
| 5,645,588 A | 7/1997 | Sklar et al. | |
| 5,653,719 A | 8/1997 | Raiken | |
| 5,665,089 A | 9/1997 | Dall | |
| 5,674,224 A | 10/1997 | Howell | |
| 5,688,284 A | 11/1997 | Chervitz | |
| 5,693,060 A | 12/1997 | Martin | |
| 5,725,556 A | 3/1998 | Moser | |
| 5,741,281 A | 4/1998 | Martin | |
| 5,741,301 A | 4/1998 | Pagedas | |
| 5,743,915 A | 4/1998 | Bertin | |
| 5,752,964 A | 5/1998 | Mericle | |
| 5,759,189 A | 6/1998 | Ferragamo | |
| 5,766,250 A | 6/1998 | Chervitz | |
| 5,766,255 A | 6/1998 | Slamin | |
| 5,769,894 A * | 6/1998 | Ferragamo | 606/148 |
| 5,769,899 A | 6/1998 | Schwartz | |
| 5,776,201 A | 7/1998 | Colleran | |
| 5,782,864 A | 7/1998 | Lizardi | |
| 5,784,763 A | 7/1998 | Cassidy | |
| 5,800,543 A | 9/1998 | McLeod et al. | |
| 5,839,768 A | 11/1998 | Wackerly | |
| 5,860,981 A | 1/1999 | Bertin | |
| 5,879,391 A | 3/1999 | Slamin | |
| 5,891,168 A | 4/1999 | Thal | |
| 5,921,986 A | 7/1999 | Bonutti | |
| 5,931,855 A | 8/1999 | Buncke | |
| 5,950,284 A | 9/1999 | Persson | |
| 6,010,525 A | 1/2000 | Bonutti | |
| 6,024,758 A | 2/2000 | Thal | |
| 6,030,007 A | 2/2000 | Bassily | |
| 6,045,574 A | 4/2000 | Thal | |
| 6,056,752 A | 5/2000 | Roger | |
| 6,063,106 A | 5/2000 | Gibson | |
| 6,066,160 A | 5/2000 | Colvin | |
| 6,066,173 A | 5/2000 | McKernan | |
| 6,068,648 A | 5/2000 | Cole | |
| 6,071,311 A | 6/2000 | O'Neil | |
| 6,086,591 A | 7/2000 | Bojarski | |
| 6,093,201 A | 7/2000 | Cooper | |
| 6,095,282 A | 8/2000 | Sadeck | |
| 6,099,568 A | 8/2000 | Simonian | |
| 6,106,545 A | 8/2000 | Egan | |
| 6,117,161 A | 9/2000 | Li | |
| 6,132,439 A | 10/2000 | Kontos | |
| 6,139,565 A | 10/2000 | Stone | |

(56) References Cited

U.S. PATENT DOCUMENTS

| | | | |
|---|---|---|---|
| 6,161,999 A | 12/2000 | Kaye |
| 6,168,629 B1 | 1/2001 | Timoteo |
| 6,171,317 B1 | 1/2001 | Jackson |
| 6,171,342 B1 | 1/2001 | O'Neil |
| 6,193,754 B1 | 2/2001 | Seedhom |
| 6,235,057 B1 | 5/2001 | Roger |
| 6,241,749 B1 | 6/2001 | Rayhanabad |
| 6,283,996 B1 | 9/2001 | Chervitz |
| 6,287,065 B1 | 9/2001 | Berlin |
| 6,317,935 B1 | 11/2001 | O'Rouke |
| 6,319,271 B1 | 11/2001 | Schwartz |
| 6,331,182 B1 | 12/2001 | Tiefenbrun |
| 6,371,958 B1 | 4/2002 | Overaker |
| 6,432,123 B2 | 8/2002 | Schwartz |
| 6,440,134 B1 | 8/2002 | Zaccherotti |
| 6,451,030 B2 | 9/2002 | Li |
| 6,461,373 B2 | 10/2002 | Wyman |
| 6,473,944 B1 | 11/2002 | Vazin |
| 6,482,210 B1 | 11/2002 | Skiba |
| 6,485,065 B2 | 11/2002 | Lusk |
| 6,506,197 B1 | 1/2003 | Rollero |
| 6,511,498 B1 | 1/2003 | Fumex |
| 6,514,274 B1 | 2/2003 | Boucher |
| 6,517,578 B2 | 2/2003 | Hein |
| 6,520,964 B2 | 2/2003 | Tallarida |
| 6,533,802 B2 | 3/2003 | Fromm et al. |
| 6,544,267 B1 | 4/2003 | Cole |
| 6,554,838 B2 | 4/2003 | McGovern |
| 6,558,389 B2 | 5/2003 | Clark |
| 6,562,071 B2 | 5/2003 | Järvinen |
| 6,569,186 B1 | 5/2003 | Winters |
| 6,575,986 B2 | 6/2003 | Overaker |
| 6,599,319 B2 | 7/2003 | Knudsen et al. |
| 6,610,067 B2 | 8/2003 | Tallarida |
| 6,645,227 B2 | 11/2003 | Fallin |
| 6,652,561 B1 | 11/2003 | Tran |
| 6,652,563 B2 | 11/2003 | Dreyfuss |
| 6,656,183 B2 | 12/2003 | Colleran |
| 6,675,447 B1 | 1/2004 | Hofeldt |
| 6,679,917 B2 | 1/2004 | Ek |
| 6,682,549 B2 | 1/2004 | Bartlett |
| 6,689,154 B2 | 2/2004 | Bartlett |
| 6,712,830 B2 | 3/2004 | Esplin |
| 6,716,234 B2 | 4/2004 | Grafton |
| 6,739,450 B2 | 5/2004 | Roshdy |
| 6,743,232 B2 | 6/2004 | Overaker |
| 6,749,616 B1 | 6/2004 | Nath |
| 6,751,143 B2 | 6/2004 | Morgan |
| 6,761,722 B2 | 7/2004 | Cole |
| 6,770,076 B2 | 8/2004 | Foerster |
| 6,773,436 B2 | 8/2004 | Donnelly |
| 6,817,634 B2 | 11/2004 | Champion |
| 6,902,573 B2 | 6/2005 | Strobel |
| 6,923,823 B1 | 8/2005 | Bartlett |
| 6,972,027 B2 | 12/2005 | Fallin |
| 6,994,725 B1 | 2/2006 | Goble |
| 7,048,748 B1 | 5/2006 | Üstüner |
| 7,087,073 B2 | 8/2006 | Bonutti |
| 7,097,654 B1 | 8/2006 | Freedland |
| 7,150,757 B2 | 12/2006 | Fallin et al. |
| 7,243,399 B2 | 7/2007 | Liao |
| 7,338,492 B2 | 3/2008 | Singhatat |
| 7,455,683 B2 | 11/2008 | Geissler |
| 7,500,983 B1 | 3/2009 | Kaiser |
| 7,530,990 B2 | 5/2009 | Fromm et al. |
| 7,537,604 B2 | 5/2009 | Huebner |
| 7,556,640 B2 | 7/2009 | Foerster |
| 7,566,339 B2 | 7/2009 | Fallin et al. |
| 7,572,275 B2 | 8/2009 | Fallin |
| 7,594,923 B2 | 9/2009 | Fallin et al. |
| 7,607,278 B2 | 10/2009 | Witkowski |
| D604,589 S | 11/2009 | Johansson |
| 7,615,061 B2 | 11/2009 | White |
| 7,637,926 B2 | 12/2009 | Foerster |
| 7,641,672 B2 | 1/2010 | Fallin |
| 7,641,694 B1 | 1/2010 | Goble et al. |
| 7,651,509 B2 | 1/2010 | Bojarski |
| 7,682,374 B2 | 3/2010 | Foerster |
| 7,695,503 B1 | 4/2010 | Kaiser |
| 7,722,644 B2 | 5/2010 | Fallin et al. |
| 7,731,718 B2 | 6/2010 | Schwammberger |
| 7,736,108 B2 | 6/2010 | Bruce |
| 7,776,077 B2 | 8/2010 | Kaiser |
| D626,231 S | 10/2010 | Perchik |
| 7,806,909 B2 | 10/2010 | Fallin et al. |
| 7,819,898 B2 | 10/2010 | Stone |
| 7,846,180 B2 | 12/2010 | Cerier |
| 7,857,830 B2 | 12/2010 | Stone |
| 7,862,597 B2 | 1/2011 | Gause |
| 7,867,253 B2 | 1/2011 | McMichael |
| 7,875,057 B2 | 1/2011 | Cook |
| 7,875,058 B2 | 1/2011 | Holmes, Jr. |
| 7,887,551 B2 | 2/2011 | Bojarski |
| 7,908,716 B2 | 3/2011 | Sorensen |
| 7,931,680 B2 | 4/2011 | Myerson |
| 7,934,506 B2 | 5/2011 | Woodson |
| 7,938,847 B2 | 5/2011 | Fanton |
| 7,955,388 B2 | 6/2011 | Jensen |
| 8,052,719 B2 | 11/2011 | Paulos |
| 8,057,511 B2 | 11/2011 | Flores |
| 8,062,334 B2 | 11/2011 | Green |
| 8,109,965 B2 | 2/2012 | Stone |
| 8,128,652 B2 | 3/2012 | Paprocki |
| 8,137,381 B2 | 3/2012 | Foerster |
| 8,162,997 B2 | 4/2012 | Struhl |
| 8,221,454 B2 | 7/2012 | Schaffhausen |
| 8,221,455 B2 | 7/2012 | Shurnas |
| 8,221,463 B2 | 7/2012 | Zucherman |
| 8,231,674 B2 | 7/2012 | Albertorio |
| 8,277,484 B2 | 10/2012 | Barbieri |
| 8,308,780 B2 | 11/2012 | Kaiser |
| 8,317,829 B2 | 11/2012 | Foerster |
| 8,388,655 B2 | 3/2013 | Fallin |
| D679,701 S | 4/2013 | Adelman |
| 8,439,976 B2 | 5/2013 | Albertorio |
| 8,663,324 B2 | 3/2014 | Schmieding |
| 2001/0014825 A1 | 8/2001 | Burke |
| 2002/0019634 A1 | 2/2002 | Bonutti |
| 2002/0019649 A1 | 2/2002 | Sikora |
| 2002/0055783 A1 | 5/2002 | Tallarida |
| 2002/0120274 A1 | 8/2002 | Overaker |
| 2002/0120281 A1 | 8/2002 | Overaker |
| 2002/0123758 A1 | 9/2002 | Bachman |
| 2002/0128684 A1 | 9/2002 | Foerster |
| 2002/0138150 A1 | 9/2002 | Leclercq |
| 2002/0147498 A1 | 10/2002 | Tallarida |
| 2003/0060887 A1 | 3/2003 | Ek |
| 2003/0120276 A1 | 6/2003 | Tallarida |
| 2003/0158606 A1 | 8/2003 | Coon |
| 2003/0225456 A1 | 12/2003 | Ek |
| 2003/0225457 A1 | 12/2003 | Justin |
| 2004/0002734 A1 | 1/2004 | Fallin |
| 2004/0015170 A1 | 1/2004 | Tallarida |
| 2004/0015171 A1 | 1/2004 | Bojarski |
| 2004/0098053 A1 | 5/2004 | Tran |
| 2004/0130155 A1 | 7/2004 | Champion |
| 2004/0133217 A1 | 7/2004 | Watschke |
| 2004/0133238 A1 | 7/2004 | Cerier |
| 2004/0133239 A1 | 7/2004 | Singhatat |
| 2004/0138666 A1 | 7/2004 | Molz |
| 2004/0138683 A1 | 7/2004 | Shelton |
| 2004/0138706 A1 | 7/2004 | Abrams |
| 2004/0148030 A1 | 7/2004 | Ek |
| 2004/0153103 A1 | 8/2004 | Schwartz |
| 2004/0153153 A1 | 8/2004 | Elson |
| 2004/0225291 A1 | 11/2004 | Schwammberger |
| 2004/0243180 A1 | 12/2004 | Donnelly |
| 2004/0254593 A1 | 12/2004 | Fallin |
| 2005/0070932 A1 | 3/2005 | Falahee |
| 2005/0277961 A1 | 12/2005 | Walters et al. |
| 2005/0288709 A1 | 12/2005 | Fallin |
| 2005/0288711 A1 | 12/2005 | Fallin |
| 2006/0122608 A1 | 6/2006 | Fallin |
| 2006/0265064 A1 | 11/2006 | Re |

(56) References Cited

U.S. PATENT DOCUMENTS

| | | |
|---|---|---|
| 2006/0282081 A1 | 12/2006 | Fanton |
| 2006/0293709 A1 | 12/2006 | Bojarski |
| 2007/0049944 A1 | 3/2007 | Stone |
| 2007/0162125 A1 | 7/2007 | Mahoney et al. |
| 2007/0203508 A1 | 8/2007 | White |
| 2007/0225805 A1 | 9/2007 | Schmieding |
| 2007/0233241 A1 | 10/2007 | Graf |
| 2008/0028991 A1 | 2/2008 | Thompson |
| 2008/0046009 A1 | 2/2008 | Schaneville et al. |
| 2008/0161852 A1 | 7/2008 | Kaiser |
| 2008/0177302 A1 | 7/2008 | Shurnas |
| 2008/0234819 A1 | 9/2008 | Schmieding |
| 2008/0287991 A1 | 11/2008 | Fromm |
| 2009/0143821 A1 | 6/2009 | Stupak |
| 2009/0182335 A1 | 7/2009 | Struhl |
| 2009/0204146 A1 | 8/2009 | Kaiser |
| 2010/0125297 A1 | 5/2010 | Guederian |
| 2010/0204731 A1 | 8/2010 | Hart |
| 2010/0256677 A1 | 10/2010 | Albertorio |
| 2010/0262185 A1 | 10/2010 | Gelfand |
| 2010/0312341 A1 | 12/2010 | Kaiser |
| 2011/0022061 A1 | 1/2011 | Orphanos |
| 2011/0046734 A1 | 2/2011 | Tobis |
| 2011/0125189 A1 | 5/2011 | Stoll, Jr. |
| 2011/0160856 A1 | 6/2011 | Sinnott |
| 2011/0301619 A1 | 12/2011 | Walters |
| 2011/0301708 A1 | 12/2011 | Stone |
| 2012/0046747 A1 | 2/2012 | Justin |
| 2012/0053630 A1 | 3/2012 | Denham |
| 2012/0059416 A1 | 3/2012 | Justin |
| 2012/0065677 A1 | 3/2012 | West, Jr. |
| 2012/0065678 A1 | 3/2012 | James |
| 2012/0065731 A1 | 3/2012 | Justin |
| 2012/0078299 A1 | 3/2012 | Ramos Clamote |
| 2012/0083837 A1 | 4/2012 | Ferragamo |
| 2012/0116452 A1 | 5/2012 | Stone |
| 2012/0123474 A1 | 5/2012 | Zajac |
| 2012/0123541 A1 | 5/2012 | Albertorio |
| 2012/0130492 A1 | 5/2012 | Eggli |
| 2012/0245630 A1 | 9/2012 | Napolitano |
| 2012/0283830 A1 | 11/2012 | Myers |
| 2012/0290002 A1 | 11/2012 | Astorino |
| 2013/0035720 A1 | 2/2013 | Perriello |
| 2013/0053884 A1 | 2/2013 | Roorda |
| 2013/0079822 A1 | 3/2013 | Maiorino |
| 2013/0103085 A1 | 4/2013 | Hart |
| 2013/0197577 A1 | 8/2013 | Wolf |
| 2013/0197580 A1 | 8/2013 | Perriello |
| 2013/0218205 A1 | 8/2013 | Stanley |

FOREIGN PATENT DOCUMENTS

| | | |
|---|---|---|
| DE | 199417019 | 2/1995 |
| EP | 0520177 | 12/1992 |
| EP | 0861050 | 9/1998 |
| EP | 0955013 | 11/1999 |
| EP | 1430840 | 6/2004 |
| EP | 2215972 | 8/2010 |
| GB | 2046826 | 11/1980 |
| JP | 6114067 | 4/1994 |
| JP | 2002065685 | 3/2002 |
| JP | 04286844 | 7/2009 |
| WO | 8909578 | 10/1989 |
| WO | 9318716 | 9/1993 |
| WO | 0139671 | 6/2001 |
| WO | 0166021 | 9/2001 |
| WO | 0166022 | 9/2001 |
| WO | 02091959 | 11/2002 |
| WO | 03051210 | 6/2003 |
| WO | 03051211 | 6/2003 |
| WO | 2004062506 | 7/2004 |
| WO | 2006029127 | 3/2006 |
| WO | WO2009009617 | 1/2009 |
| WO | 2009049002 | 4/2009 |
| WO | 2011003002 | 1/2011 |

\* cited by examiner

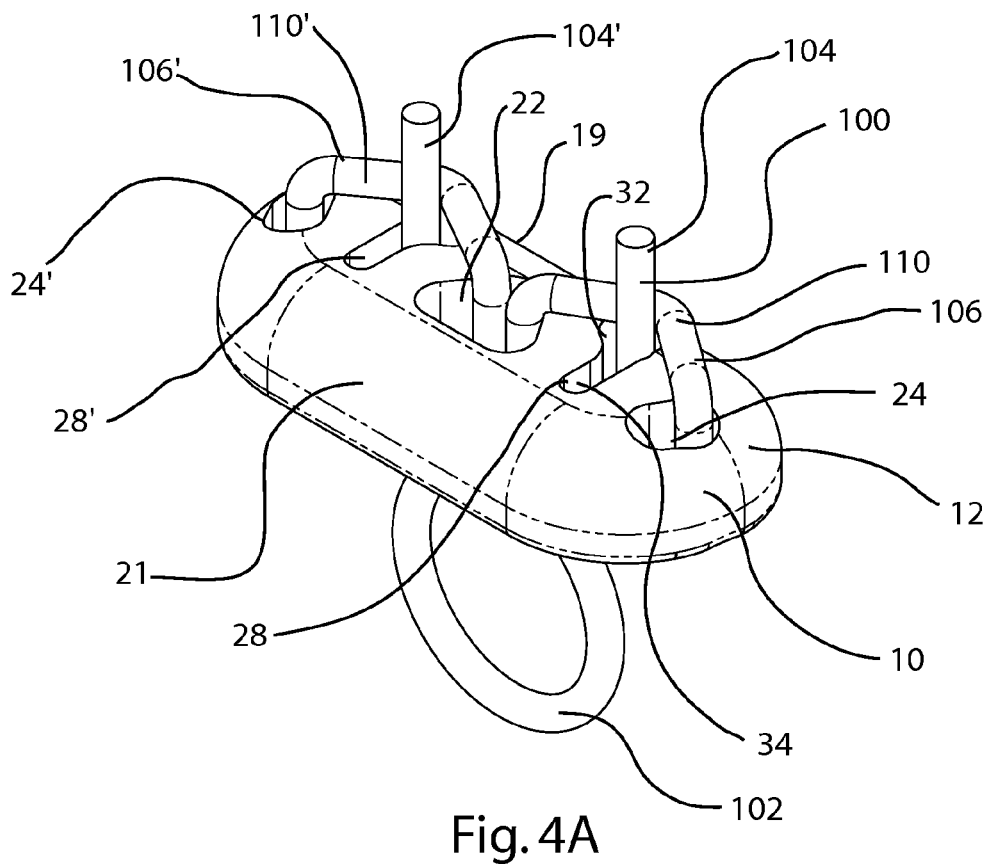
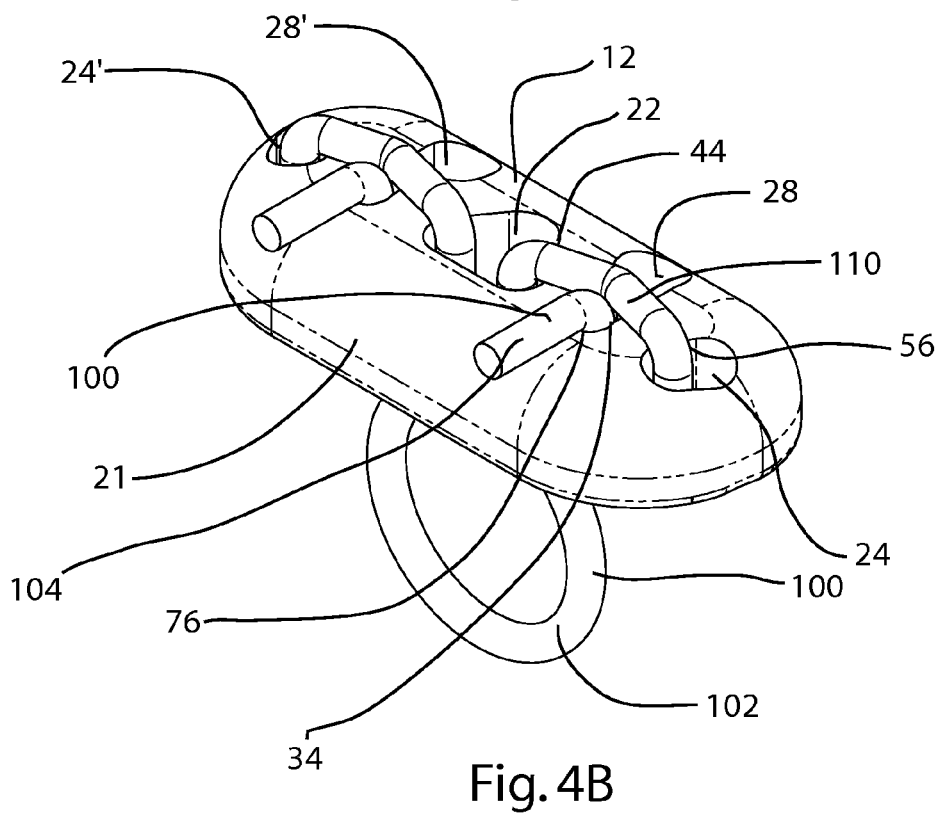

COMPACT LINE LOCKS AND METHODS

CROSS-REFERENCE TO RELATED APPLICATIONS

This application is a continuation of:

U.S. application Ser. No. 12/754,774, now U.S. Pat. No. 8,388,655, filed Apr. 6, 2010, and is entitled COMPACT LINE LOCKS AND METHODS.

U.S. patent application Ser. No. 12/754,774 is a continuation of:

U.S. application Ser. No. 11/125,885, now U.S. Pat. No. 7,722,644, filed May 9, 2005, and is entitled COMPACT LINE LOCKS AND METHODS.

U.S. patent application Ser. No. 11/125,885 is a continuation-in-part of the following:

U.S. application Ser. No. 10/459,375, now U.S. Pat. No. 7,150,757, filed Jun. 11, 2003, and is entitled LINE LOCK SUTURE ATTACHMENT SYSTEMS AND METHODS;

U.S. application Ser. No. 10/936,376, now U.S. Pat. No. 7,566,339, filed Sep. 7, 2004, and is entitled ADJUSTABLE LINE LOCKS AND METHODS;

U.S. application Ser. No. 10/942,275, now U.S. Pat. No. 7,806,909, filed Sep. 15, 2004, and is entitled LINE LOCK THREADING SYSTEMS AND METHODS; and U.S. application Ser. No. 11/001,866, now U.S. Pat. No. 7,594,923, filed Dec. 1, 2004, and is entitled LINE LOCK SUTURE ATTACHMENT SYSTEMS AND METHODS.

All of the above-named documents are hereby incorporated by reference in their entirety.

BACKGROUND OF THE INVENTION

1. The Field of the Invention

The present invention relates generally to devices to replace knots and more specifically to devices to replace surgical knots tied in open, arthroscopic, and endoscopic procedures.

2. The Relevant Technology

Numerous devices have been developed to eliminate the need to tie knots as a way of securing a line. The devices that accomplish the same function as a knot, which is in part to secure a line to retain tension in a portion of the line, are typically referred to as line locks.

Line locks generally operate in one of two ways. Some line locks are manually actuated to secure one or more lines so that tension is maintained in a portion of the line(s). Once actuated, the line lock resists sliding along the line(s) either toward or away from the tensioned portion of the line. Other line locks are continuously adjustable in one direction so that tension is increased in the portion of the line upon which the line lock is advanced. The continuously adjustable line locks resist movement away from the tensioned portion of the line, but can be further advanced toward the tensioned portion of the line with an appropriately applied force.

The portion of a line that is put under tension, typically to secure some object, is commonly referred to as the standing end. The portion of the line that extends toward the line handler is commonly referred to as the working end. A knot in a line, or a line lock attached to a line, is the demarcation between the standing end and the working end.

Continuously adjustable line locks offer several advantages. They are passive locking devices, meaning that no other operation is required to secure the line lock once it is moved along the line to its desired position. Furthermore, these line locks can be used to continuously increase the tension in the standing end until it reaches a desired level of tension.

The advantages of line locks over tied knots are very attractive in many varied applications, including the use of surgical sutures. However, the line locks developed to date have many deficiencies when considered for surgical suture applications.

Many known line locks for surgical applications are somewhat small, and as a result, they have small passageways that are positioned quite close to each other. This makes it somewhat difficult to thread the suture through the line lock in the proper pattern. Furthermore, the user must select and apply the correct suture because improper suture selection can impair the locking and/or strength of the attachment system. Additionally, the proper needle must be attached to the suture. Thus, there are multiple selection and assembly steps that must be performed prior to use of the attachment system.

Known line locks use line on line friction to create the locking effect, and this line on line friction makes it difficult to advance the line lock over suture. Known line locks rely on maintenance of tension in the standing end to prevent the line lock from migrating back along the working end.

In surgical suture applications, the working end is typically trimmed closely to the line lock. As a result, the line lock can easily disassociate from the suture once tension in the standing end is lost. In most, if not all, surgical applications, a free-floating device such as a line lock can potentially harm adjacent body tissues. Additionally, known line locks are susceptible to loosening during cyclic variations in the tension of the standing end. This cyclic variation in the standing end tension is common in surgical applications as tissues are stressed and then relaxed. Loosening of the line lock thus compromises the securing function for which it was intended.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 4A is a perspective view of the line lock shown in FIG. 1 with a line routed therethrough in a slack unlocked position.

FIG. 4B is a perspective view of the line lock shown in FIG. 4A with the line in a tensioned locked position.

DETAILED DESCRIPTION OF THE PREFERRED EMBODIMENTS

The present invention relates to line locks that can be used in part to replace surgical knots tied in sutures in open, arthroscopic, and endoscopic procedures. By increasing the size of the line locks, it is also appreciated that the line locks can be used outside of surgical procedures for any use where it is desired to selectively adjust and/or tie off a line such as a rope, cord, string, or other conventional type of line.

In this application, the term "couple" broadly refers to connection of two items to each other. Two items may be "coupled" if they are connected together in a manner that prevents relative motion on one direction, but not another. A "longitudinal length" of an object is the length of the object along its longest dimension. "Cooperation" of a plurality of passageways to receive multiple suture portions does not require that each suture portion pass through all of the cooperating passageways.

Figure 1:
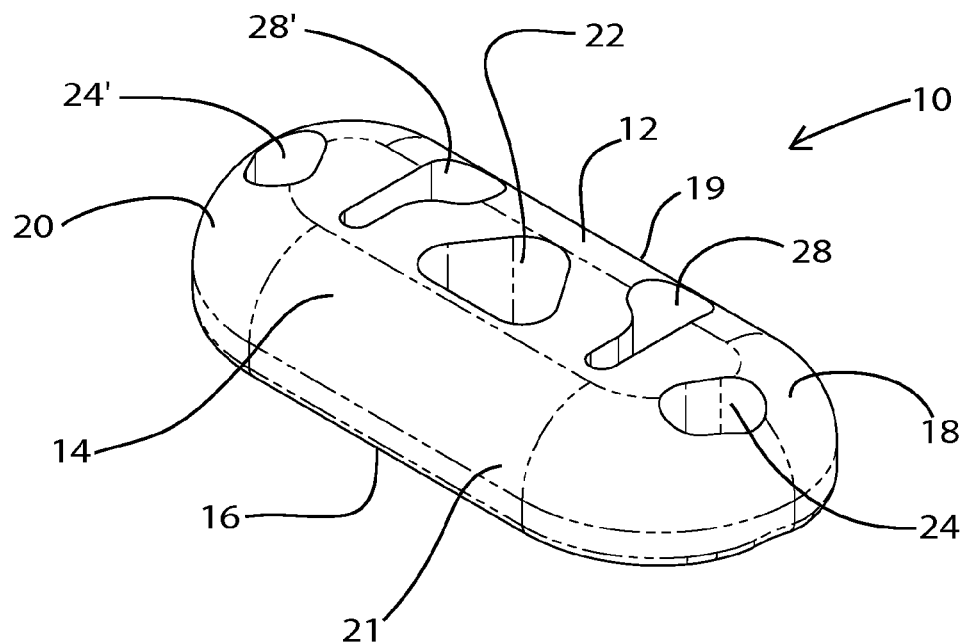
FIG. 1 is a perspective view of an adjustable line lock.

Depicted in FIG. 1 is one embodiment of a line lock 10 incorporating features of the present invention. Line lock 10 comprises an elongated body 12 having a top surface 14 and an opposing bottom surface 16 that each extend between a first end 18 and an opposing second end 20. Body 12 also has a first side 19 and an opposing second side 21 extending between first end 18 and second end 20. In the embodiment depicted, body 12 has a substantially rectangular configuration with rounded ends. As will be apparent from the following disclosure, however, body 12 can be any desired configuration such as triangular, circular, square or any other polygonal or irregular configuration.

In typical surgical applications, body 12 has a maximum dimension D along its length (FIG. 2) which is typically less than about 2 cm, more commonly less than about 1.5 cm, and even more commonly less than about 1 cm. Other dimensions can also be used. By way of example and not by limitation, in one embodiment body 12 has a height in a range between about 1 mm to about 1.5 mm, a width in a range between about 2 mm to about 3 mm, and length D in a range between about 5 mm to about 8 mm. In non-surgical applications, body 12 can be any desired dimension. For example, maximum dimension D can be in a range from about 5 cm to about 0.5 m. Again, other dimensions can also be used.

For use in surgical applications, body 12 can be comprised of any biocompatible material. The biocompatible material can be bioabsorbable or non-bioabsorbable. Examples of typical materials include non-bioabsorbable plastic, bioabsorbable plastic, synthetic tissue, and allograft tissue. In non-surgical applications, body 12 can be made of any desired material such as metal, plastic, wood, fiberglass, composite, or the like.

As depicted in FIG. 1, centrally extending through body 10 between top surface 14 and bottom surface 16 is a primary passageway 22. As used in the specification and appended claims, the term "passageway" is broadly intended to include closed apertures, such as depicted by primary passageway 22, partially bounded apertures, open channels, recesses, grooves, slots, and the like, that are capable of receiving a line and at least partially retaining the line therein. The term "line" as used in the specification and appended claims is broadly intended to include suture, cord, rope, filament, wire, cable, and any other form of line.

In this application, the phrase "substantially bounded aperture" refers to an aperture that is sufficiently encircled by material to prevent a line from exiting the aperture via motion transverse to the length or axis of the aperture. Thus, a substantially bounded aperture may be fully encircled by material, or may have one or more breaks, each of which is smaller than the diameter of the line that is to pass through the substantially bounded aperture.

Extending between surfaces 14 and 16 at first end 18 of body 12 is a first secondary passageway 24. A second secondary passageway 24' extends between surfaces 14 and 16 at second end 20. Extending through body 12 at a location between primary passageway 22 and first secondary passageway 24 is a first working passageway 28. In one embodiment, although not necessarily required, first working passageway 28 is disposed between primary passageway 22 and first secondary passageway 24 such that a geometric line segment 36 (FIG. 2) can be extended between primary passageway 22 and first secondary passageway 24 so that line segment 36 intersects with first working passageway 28. Similar to first working passageway 28, a second working passageway 28' extends through body 12 at a location between primary passageway 22 and second secondary passageway 24'.

Each working passageway 28 and 28' has an elongated transverse cross sectional area that extends between a first end 38 and an opposing second end 40. Each working passageway 28, 28' comprises an enlarged access region 32 at first end 38 which communicates with a constricted capture slot 34 at second end 40. Access region 32 is sized to enable easy feeding of a line into and through the corresponding working passageways 28, 28'. Accordingly, although access region 32 can be slightly smaller than the transverse cross sectional area of the line which is to be passed therethrough, access region 32 typically has a transverse cross sectional area that is equal to or slightly larger than the transverse cross sectional area of the line that is to be passed therethrough.

In contrast, capture slot 34 has a width W that is substantially equal to or less than the diameter of the line that is to be passed through working passageways 28, 28'. For example, in one embodiment width W is less than about 0.9 times the diameter of the line and more commonly less than about 0.75 times the diameter of the line. It is appreciated that working passageways 28, 28' can come in a variety of different configurations. For example, capture slot 34 can come in a variety of different constricted, tapered, or notched shaped configurations that are capable of securely retaining a line through wedged engagement. For line made of less compressible material, such as metal, the required difference between the width W and the diameter of the line may be less than the examples given above.

Figure 2:
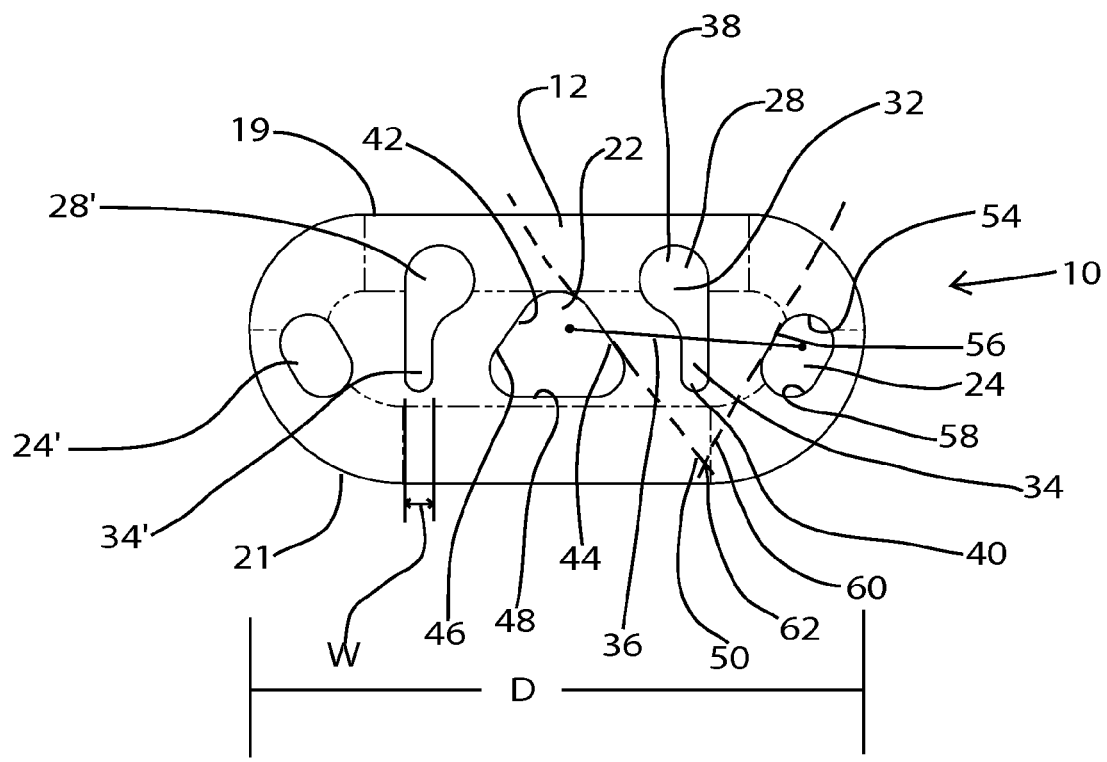
FIG. 2 is a top plan view of line lock shown in FIG. 1.

As depicted in FIG. 2, central passageway 22 is bounded by an interior surface 42 of body 12 having a substantially triangular transverse cross section. Interior surface 42 comprises a first side face 44 disposed toward first working passageway 28, a second side face 46 disposed toward second working passageway 28' and which intersects with first side face 44, and a third side face 48 extending between first side face 44 and second side face 46. Although side faces 44 and 46 are shown as being substantially flat, in alternative embodiments side faces 44 and 46 can be curved or irregular. In one embodiment, however, first side face 44 is substantially disposed in or tangent to a first plane illustrated by dashed line 50. With reference to FIG. 2, plane 50 slopes toward second end 40 of first working passageway 28 as plane 50 extends from first side 19 of body 12 to second side 21.

First secondary passageway 24 is bounded by an interior surface 54 of body 12 having an elongated transverse cross section. Interior surface 54 comprises a first side face 56 disposed toward first working passageway 28 and an opposing second side face 58. Although side faces 56 and 58 are shown as being substantially flat, in alternative embodiments side faces 56 and 58 can also be curved or irregular. Again, in one embodiment first side face 56 is substantially disposed in or tangent to a second plane illustrated by dashed line 60. With reference to FIG. 2, second plane 60 slopes toward second end 40 of first working passageway 28 as second plane 60 extends from first side 19 of body 12 to second side 21.

In the above discussed configuration, first plane 50 and second plane 60 are disposed so as to be converging as they extend from first side 19 of body 12 to second side 21. In the embodiment depicted, planes 50 and 60 intersect at a location 62 on body 12 that is at least substantially aligned with a central longitudinal axis of capture slot 34. In other embodiments, location 62 can be directly adjacent to body 12 or at a distance from body 12. Likewise, location 62 need not be aligned with the central longitudinal axis of capture slot 34. Although not required, in one embodiment planes 50 and 60 are disposed at equally opposing angles relative to the central longitudinal axis of capture slot 34. Furthermore, planes 50 and 60 can intersect so as to form an inside angle therebetween in a range between about 5° to about 85°.

Second secondary passageway 24' has substantially the same configuration as first secondary passageway 24. Likewise, second secondary passageway 24' has substantially the same relative position to second working passageway 28' and second side face 46 of primary passageway 22 as first secondary passageway 26 has to first working passageway 28 and first side face 44 of primary passageway 22. As such, the discussion with regard to planes 50 and 60 are also applicable to primary passageway 22 and second secondary passageway 24'.

By way of example of the passageways and not by limitation, for use with a size USP #2 braided suture, which has a diameter in a range between about 0.5 mm to about 0.6 mm, primary passageway 22 has a length in a range between about 1.3 mm to about 1.5 mm and a width in a range between about 1 mm to about 1.3 mm. Secondary passageways 24 and 24' have a width of about 0.8 mm and a length in a range between 1 mm to about 1.3 mm. Access region 32 of working passageways 28 and 28' have width in a range between about 0.7 mm to 1 mm while capture slots 17 have a width in a range between about 0.3 mm to 0.4 mm.

Figure 3:
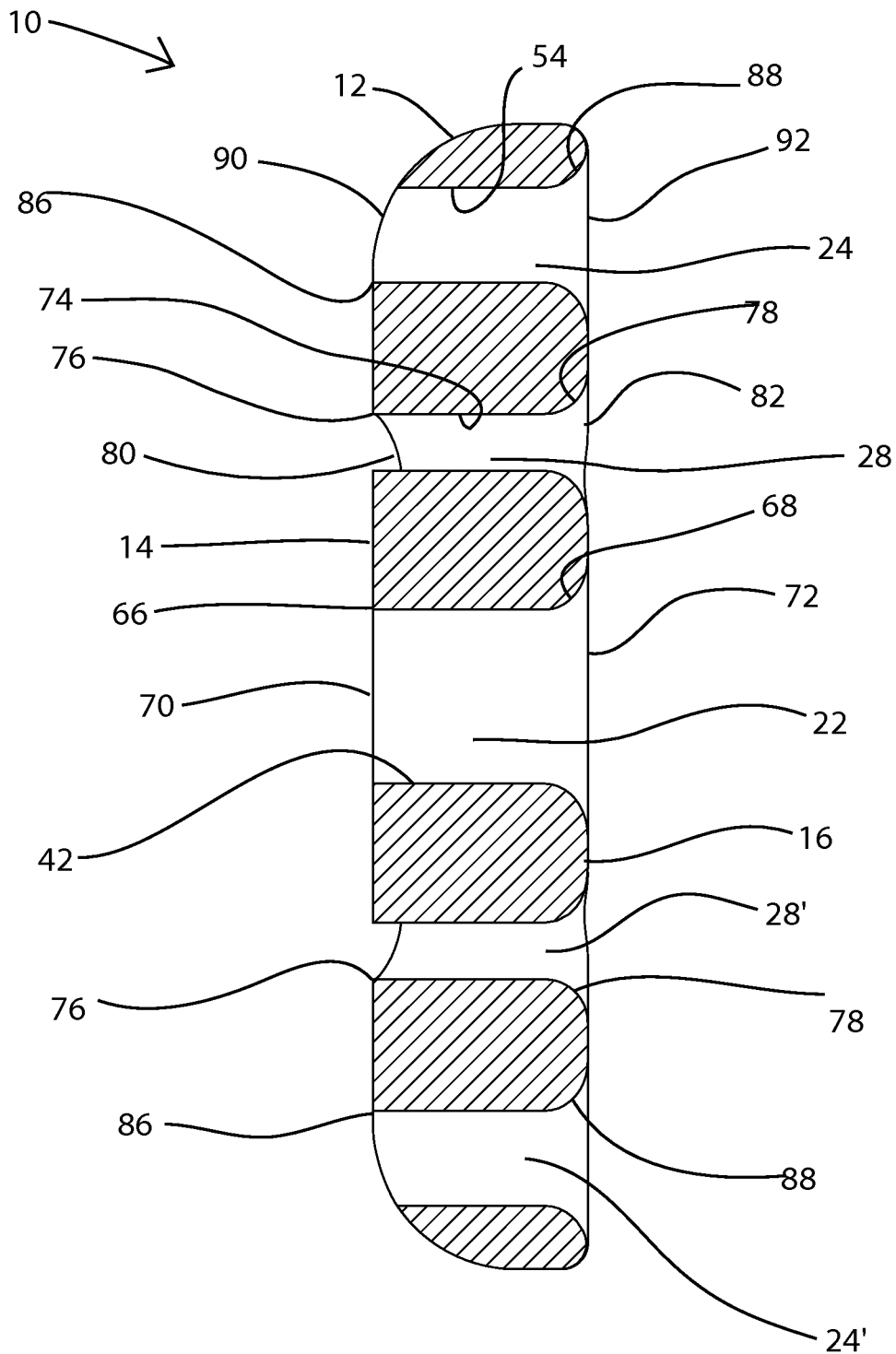
FIG. 3 is an elevated cross sectional side view of the line lock shown in FIG. 1.

Depicted in FIG. 3, interior surface 42 of primary passageway 22 extends to a top outside corner 66 and an opposing bottom outside corner 68. Top outside corner 66 bounds a top primary opening 70 while bottom outside corner 66 bounds a bottom primary opening 72. Similarly, first working passageway 28 has an interior surface 74 that extends to a top outside corner 76 and an opposing bottom outside corner 78. Top outside corner 76 bounds a top working opening 80 while bottom outside corner 76 bounds a bottom working opening 82. Likewise, interior surface 54 of first secondary passageway 24 extends to a top outside corner 86 and an opposing bottom outside corner 88. Top outside corner 86 bounds a top secondary opening 90 while bottom outside corner 86 bounds a bottom secondary opening 92.

For reasons as will be discussed below in greater detail, each of top outside corners 66, 76, and 86 has a radius of curvature that is smaller than the radius of curvature of the corresponding bottom outside corners 68, 78, 88. By way of example and not by limitation, in one embodiment top outside corners 66, 76, and 86 each have a radius of curvature in a range between about 0 mm to about 1 mm with about 0 mm to about 0.5 mm being more common. In contrast, bottom outside corners 68, 78, and 88 each have a radius of curvature in a range between about 0.25 mm to about 2 mm with about 0.5 mm to about 1.5 mm being more common. Other dimensions can also be used, particularly outside of the surgical area. In yet other embodiments it is appreciated that the top outside corners and the bottom outside corners can have the same radius of curvature or that only one or more of the top outside corners may be smaller than one or more of the bottom outside corners. In still other embodiments, it is appreciated that only a portion of one or more of the top outside corners may be smaller than a portion of one or more of the bottom outside corners.

It is again noted that second secondary passageway 24' and second working passageway 28' having substantially the same configuration as first secondary passageway 24 and first working passageway 28, respectively. As such, the same discussion with regard to the outside corners are also applicable thereto. Likewise, like elements are identified by like reference characters.

Depicted in FIG. 4A is a line 100 adjustably mounted on line lock 12. Line 100 comprises a standing portion 102 in the form of a loop which extends below primary passageway 22, a first working portion 104 which extends out of first working passageway 28, and a first locking portion 106 extending therebetween. It is appreciated that each of the sections 102, 104, and 106 of line 100 are relative to each other in that they change as line 100 is adjusted on line lock 10. Line 100 further includes a second working portion 104' which extends out of second working passageway 28' and a second locking portion 106' that extends between standing portion 102 and second working portion 104'.

First locking portion 106 extends up through primary passageway 22, down through first secondary passageway 24, and then up through first working passageway 28. The section of locking portion 106 extending between primary passageway 22 and first secondary passageway 24 is referred to as compression section 110. Line 100 passes up through first working passageway 28 so that first working portion 104 is disposed between compression section 110 and capture slot 34. Second locking portion 106' is similarly passed through passageways 22, 24', and 28'.

During use, standing portion 102 of line 100 is typically looped around, embedded within, or passed through tissue, or some other structure. To secure standing portion 102 to the structure, unwanted slack is removed from standing portion 102. This is accomplished by sliding line lock 10 over standing portion 102 and/or pulling on working portion 104 and/or 104' so that the unwanted slack is pulled through line lock 10. In either event, at least one of working portions 104 and 104' increases in length while standing portion 102 shortens.

In the configuration depicted in FIG. 4A, line 100 is passing through enlarged access regions 32 of working passageways 28 and 28'. In this position, relative locking portions 106 and 106' freely slide through corresponding passageways of line lock 10 as the unwanted slack from standing portion 102 is removed. A mild tension force is typically applied to working portions 104 and 104' as the unwanted slack is removed. The applied force pushes compression section 110 and 110' back toward first side 19 of body 12 and thus away from capture slots 34, 34'. In turn, the portion of line 100 passing through primary passageway 22 and secondary passageways 24 and 24' also naturally slides back within the passageways toward first side 19 of body 12. This movement of line 100 helps to decrease frictional resistance on line 100.

Once the slack is removed from standing portion 102, further force is applied to working portions 104, 104' and/or line lock 10 so as to tension locking portions 106, 106' on line lock 10. As depicted in FIG. 4B, as line 100 is tensioned, the diverging side face 44 of primary passageway 22 and side face 56 of first secondary passageway 24 cause the portions of line 100 passing therethrough, and thus compression portion 110 extending therebetween, to slide toward first side 21 of body 12.

Furthermore, as line 100 is tensioned, compression portions 110, 110' are shortened causing them to move into a more linear orientation. As a result of the above, tensioning of line 100 causes compression portions 110, 110' to force working portions 104, 104' toward corresponding capture slots 34, 34'. In turn, at least a portion of line 100 within working passageways 28 and 28' is forced into corresponding capture slots 34, 34' so that line 100 is secured therein by wedged frictional engagement. That is, line 100 is secured by compression within capture slots 34, 34' because line 100 has a diameter larger than the width of capture slots 34, 34'. Once line 100 is captured under compression in capture slots 34, 34', line 100 will remain captured even if there is a complete loss of tension in standing end 102. Thus, "locking" of line lock 10 to line 100 ensures that line lock 10 will not become separated from line 100, even under cyclic changes in line tension in standing end 102. Furthermore, line lock 10 is continuously adjustable in that further tension can be applied to standing portions 104 and/or 104' at any time to remove additional slack from standing portion 102 while retaining line 100 locked to line lock 10.

The passageways extending through line lock 10 are also configured such that as compression portions 110 and 110' force line 100 into capture slots 34 and 34', compression portions 110 and 110' also fold and/or bias working ends 104 and 104' over and/or against top outside corner 76 of capture slots 34 and 34'. In view of the relatively small radius of curvature of top outside corner 76, the engagement between the captured working ends 104 and 104' and top outside corner 76 creates a high degree of friction which forms a secondary locking mechanism between line 100 and line lock 10. As such, the engagement between capture working ends 104 and 104' and top outside corner 76 prevents backward movement of line lock 10 relative to line 100.

In the embodiment depicted in FIG. 4B, compression portion 110 is disposed above a portion of top outside corner 76 so as to directly bias working ends 104 against top outside corner 76. Compression portion 110 is also shown disposed directly above a portion of working end 104 that is biasing against top outside corner 76. In alternative embodiments, compression portion 110 when tensioned can extend between central passageway 22 and secondary passageways 24 without passing over working passageway 28. That is, compression portion 110 can pass at a location toward second side 21 of line lock 10 that is spaced apart from working passageway 28. In this embodiment, compression portion 110 still passes over working end 104, thereby remotely causing working end 104 to fold over and bias against top outside corner 76.

One of the unique features of the present embodiment is that as line lock 10 is advanced toward standing end 102 when standing end 102 is not under tension, i.e., when slack is being removed from standing end 102, working ends 104 and 104' tend to push away compression portions 110 and 110', as discussed above, thereby minimizing frictional engagement between working ends 104, 104', compression portions 110, 110' and line lock 10. As a result, line lock 10 can be easily advanced on line 100.

Furthermore, unlike some other continuously adjustable line locks known in the art that use a loop portion to draw in and wedge a portion of a line within a bore hole, compression portions 110 and 110' traverse a substantially straight path because they are constrained by secondary passageways 24 and 24' and primary passageway 22. This substantially straight path translates to a lower frictional resistance to sliding not possible with other adjustable line locks known in the art.

As previously discussed, line 100 is routed through passageways 22, 24, and 28 so as to pass over the outside corners of the passageways. When a tensioned section of line 100 passes around a first outside corner of line lock 10, friction produced between line 100 and the corresponding outside corner cause a decrease in tension on the portion of line 100 extending away from the outside corner on the side opposite the tensioned section. The friction produced at the outside corner must be overcome in order to cause line 100 to slide. Similarly, as the line passes around subsequent outside corners away from the tensioned section, each subsequent corner produces an incremental decrease in line tension and a corresponding incremental increase in friction that must be overcome to cause line 100 to slide. The loss in tension and increase in friction diminishes for each subsequent corner. Thus, the first corners are the most significant.

Figure 6:
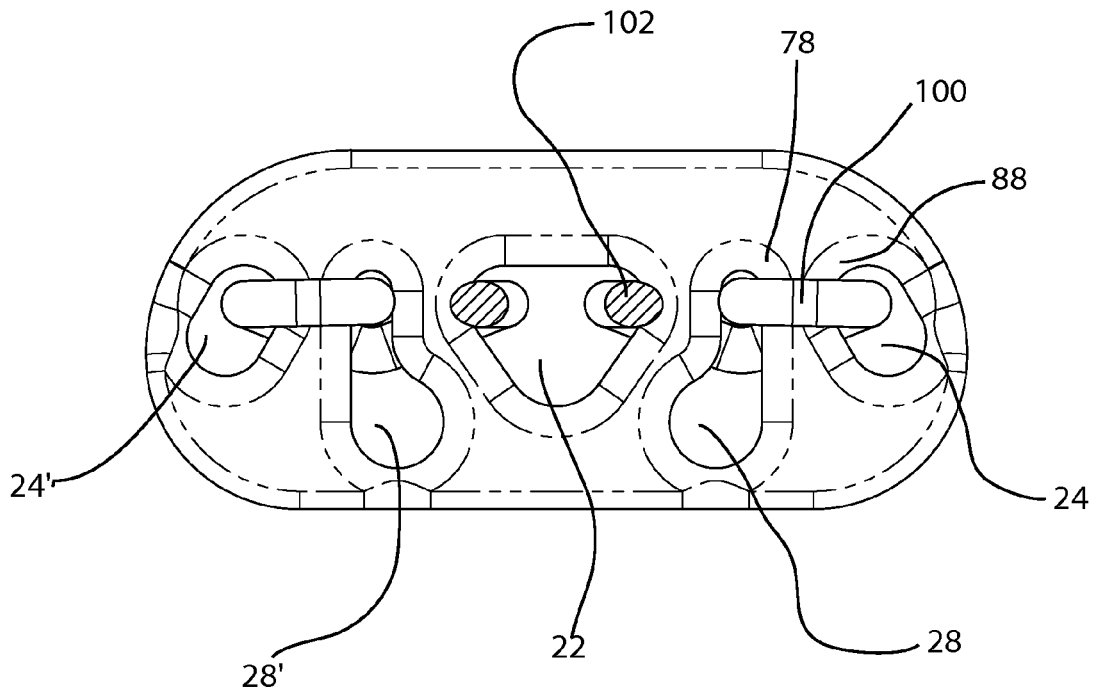
FIG. 6 is a bottom cross sectional view of the line lock shown in FIG. 4B.

As depicted in FIG. 6, in view of the above discussion, when working end 104 is tensioned and standing end 102 is slack, line 100 extending from working end 104 toward line lock 10 first turns on bottom outside corner 78 of working passageway 28 and bottom outside corner 88 of secondary passageway 24. As a result of the fact that these are the closest outside corners to tensioned working end 104, outside corners 78 and 88 will produce the highest frictional resistance. Accordingly, to minimize the frictional resistance produced by outside corners 78 and 88 and thereby ease the sliding of line lock 10 toward standing end 102, outside corners 78 and 88 are generously rounded as previously discussed.

Figure 5:
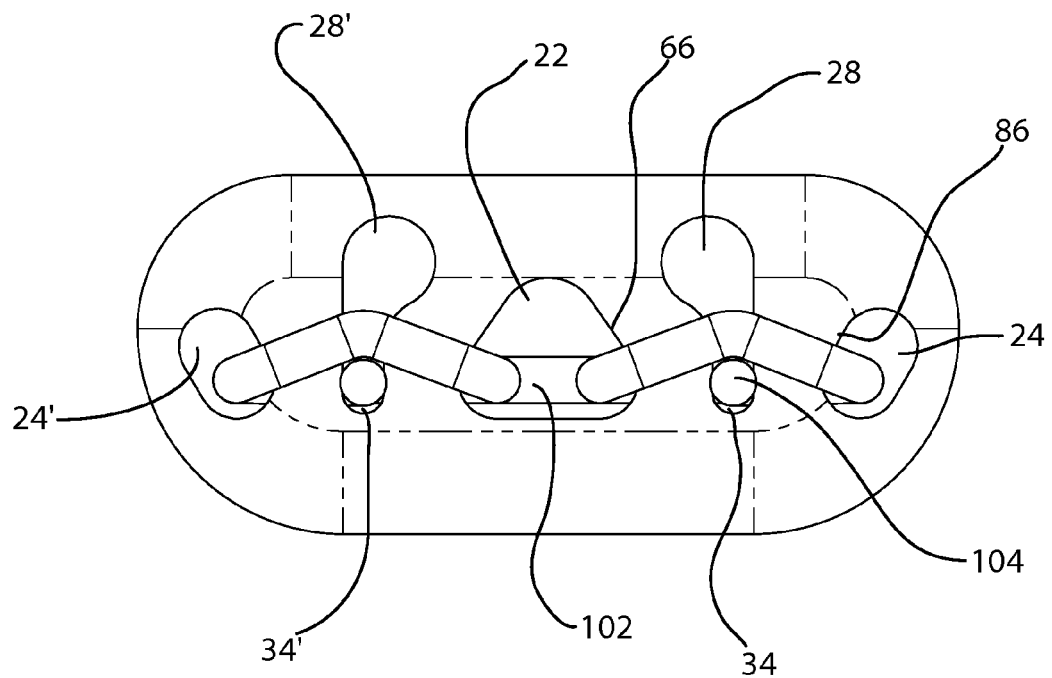
FIG. 5 is a top plan view of the line lock shown in FIG. 4B.

In contrast, as depicted in FIG. 5, when standing end 102 is tensioned and working end 104 is slack, line 100 extending from standing end 102 toward line lock 10 first turns on top outside corner 66 of primary passageway 22 and top outside corner 86 of secondary passageway 24. In view of the fact that these are the closest outside corners to tensioned standing end 102, outside corners 66 and 86 will produce the highest frictional resistance. Accordingly, to maximize the frictional resistance produced by outside corners 66 and 86 and thereby minimizing slipping of line 100 once tensioned, outside corners 66 and 86 are formed relative sharp as previously discussed. More specifically, top outside corners 66 and 86 have a smaller radius of curvature than bottom outside corners 78 and 88. It is noted that not all of each outside corner that bounds a corresponding opening has to have the same radius of curvature. For example, the portion of each outside corner that directly engages line 100 can have a radius of curvature that is different from the remainder of the corresponding outside corner.

Figure 7:
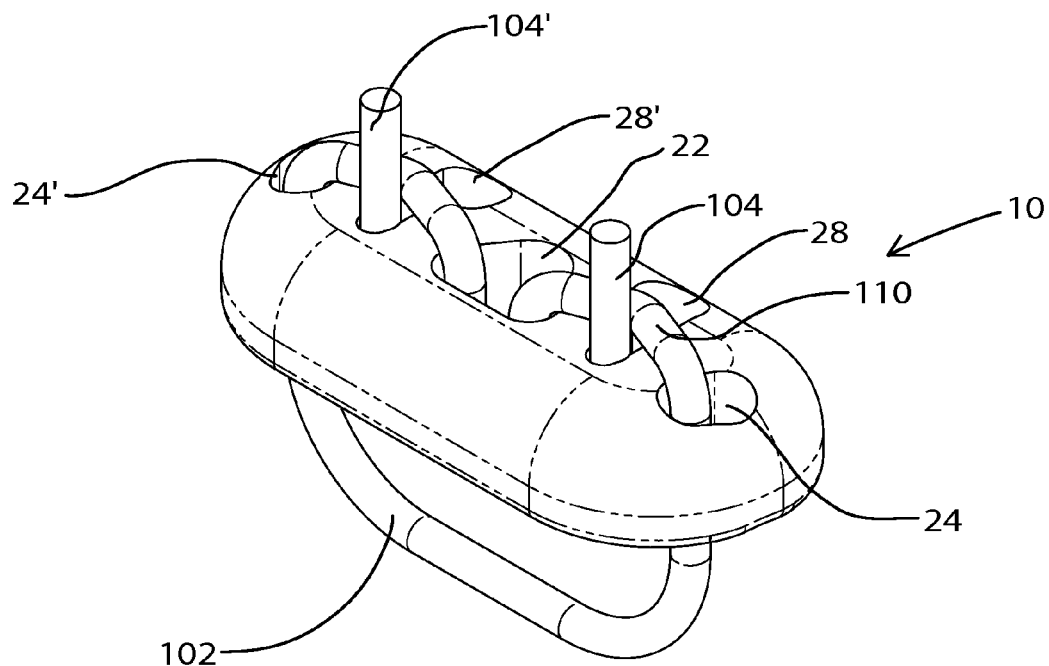
FIG. 7 is a perspective view of the line lock shown in FIG. 1 with a line routed in a different path.

Depicted in FIG. 7, line lock 10 is shown having an alternative routing of line 100. To achieve this routing, working ends 104 and 104' are passed up through secondary passageways 24 and 24', respectively, down through primary passageway 22, and then back up through working passageways 28 and 28', respectively. Again compression portions 110 and 110' are formed that selectively force working ends 104 and 104' toward capture slots 34 as discussed above. In yet another alternative, it is appreciated that one end of line 100 can be routed as shown in FIG. 4A while the opposing end of line 100 is routed as shown in FIG. 7.

Figure 8:
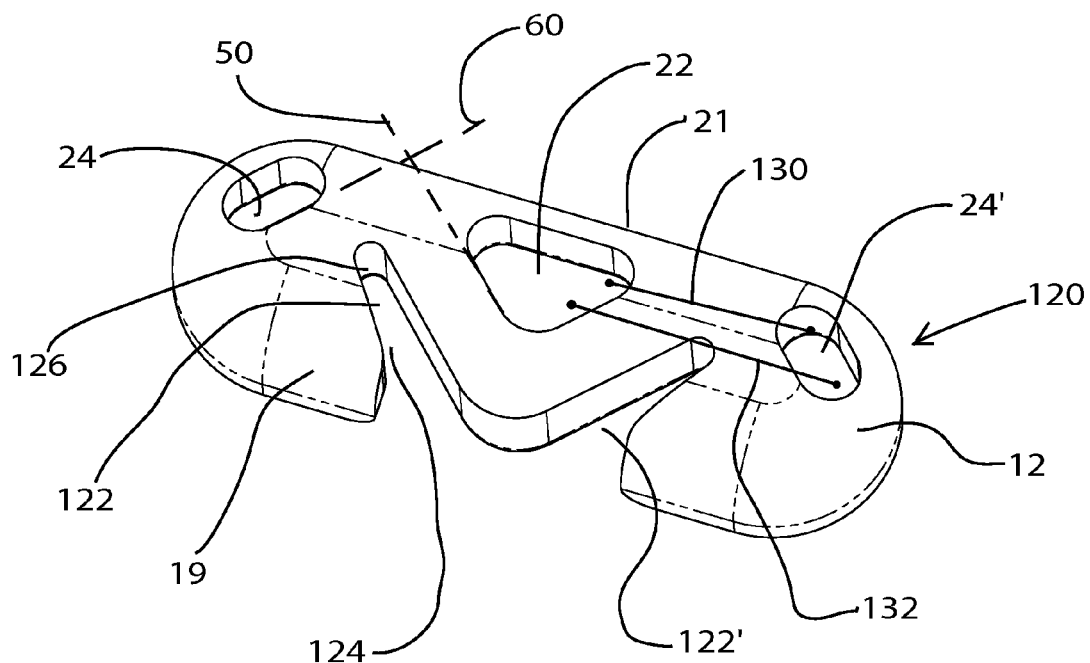
FIG. 8 is a perspective view of an alternative embodiment of the line lock shown in FIG. 1 with open working passageways.

Depicted in FIG. 8 is an alternative embodiment of a line lock 120. It is noted that all common elements of alternative embodiments of line locks disclosed herein are identified by like reference characters. Line lock 120 comprises body 12 having primary passageway 22 and secondary passageways 24 and 24' extending therethrough as discussed above with regard to FIG. 1. In contrast to the circumferentially closed working passageways 28, 28', however, line lock 120 comprises working passageways 122 and 122' that are circumferentially open. That is, each working passageway 122 and 122' comprises an elongated tapered slot having a first end 124 and an opposing second end 126. First end 124 is open along first side 19 of body 12 to facilitate convenient loading of line 100 therein. First end 124 also typically has a width greater than the diameter of line 100. Second end 126 extends to a location between primary passageway 22 and a corresponding one of secondary passageway 24, 24'.

In this embodiment it is noted that the passageways are positioned such that a geometric line segment 130 can be extended between primary passageway 22 and secondary passageway 24' such that line segment 130 does not intersect with working passageway 122'. However, a geometric line segment 132 can also be extended between primary passageway 22 and secondary passageway 24' such that line segment 132 intersects with working passageway 122'. Second end 126 of each working passageway 122, 122' typically has a width substantially equal to or smaller than the diameter of line 100.

Figure 9:
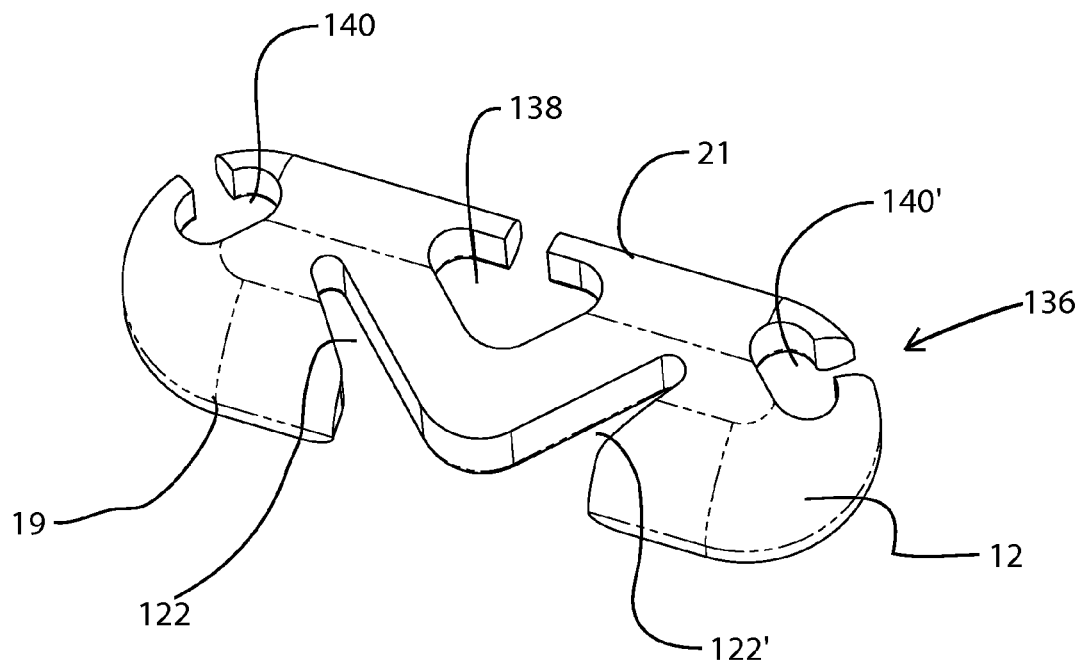
FIG. 9 is a perspective view of another alternative embodiment of the line lock shown in FIG. 1 with open passageways.

Depicted in FIG. 9 is another alternative embodiment of a line lock 136 having substantially the same configuration as line lock 120. In contrast to the circumferentially bounded primary passageway 22 and secondary passageways 24 and 24' of line lock 120 in FIG. 8, however, line lock 136 comprises a partially bounded primary passageway 138 which is open at second side 21 of body 12 and partially bounded secondary passageways 140 and 140' that are also each open at or adjacent to second side 21 of body 12.

Figure 10:
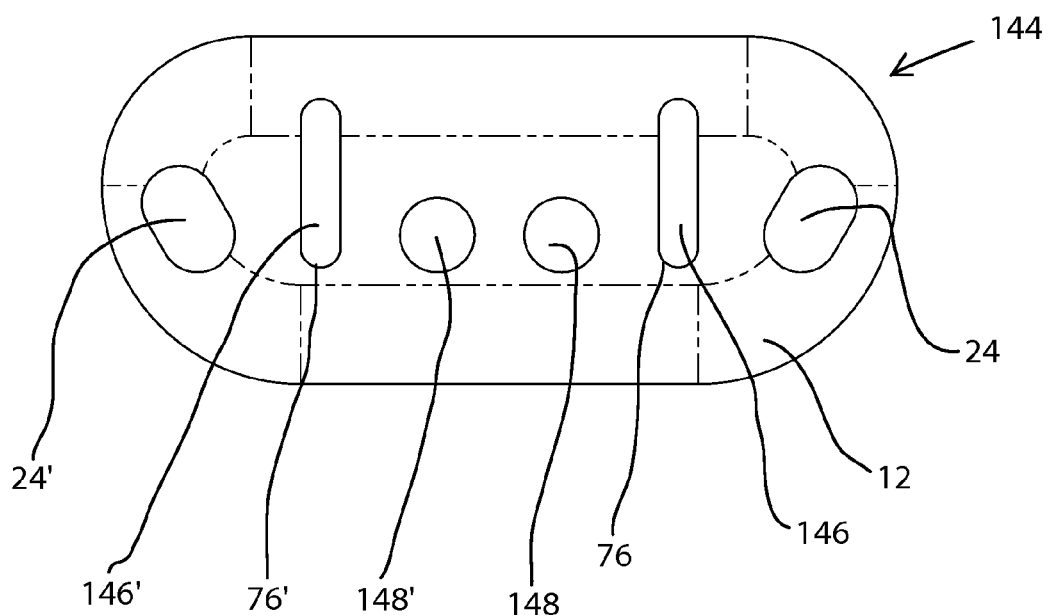
FIG. 10 is a perspective view of another alternative embodiment of the line lock shown in FIG. 1 with dual primary passageways and uniform working passageways.

Two separate locking features were previously discussed with regard to securing line 100 to line lock 10. Specifically, line 100 is secured by being wedged into capture slots 34 and 34' and by biasing working portions 104 and 104' against the top outside corner 76 of each working passageway 28, 28'. In alternative embodiments, it is appreciated that the locking features can be used independently. For example, depicted in FIG. 10 is a line lock 144 having body 12 with secondary passageways 24 and 24'. In contrast to line lock 10, however, line lock 144 comprises working passageways 146 and 146' wherein capture slots 34 have been eliminated. Working passageways 146 and 146' merely comprise elongated channels having a width substantially the same size or larger than the diameter of the line 100 to be passed therethrough. Line 100 is thus primarily secured to line lock 144 as a result of compression portions 110, 110' biasing line 100 against top outside corner 76 of each working passageways 146 and 146' as previously discussed.

Line lock 144 is also distinguished over line lock 10 in that primary passageway 22 has been replaced with a first primary passageway 148 and a spaced apart second primary passageway 148'. Primary passageways 148 and 148' operate with opposing ends of line 100. It is also noted that in alternative embodiments primary passageway(s) and/or the secondary passageways need not be elongated to allow the line passing therethrough to slide toward opposing sides 19 and 21 of body 12 as previously discussed with regard to line lock 10.

Figure 11:
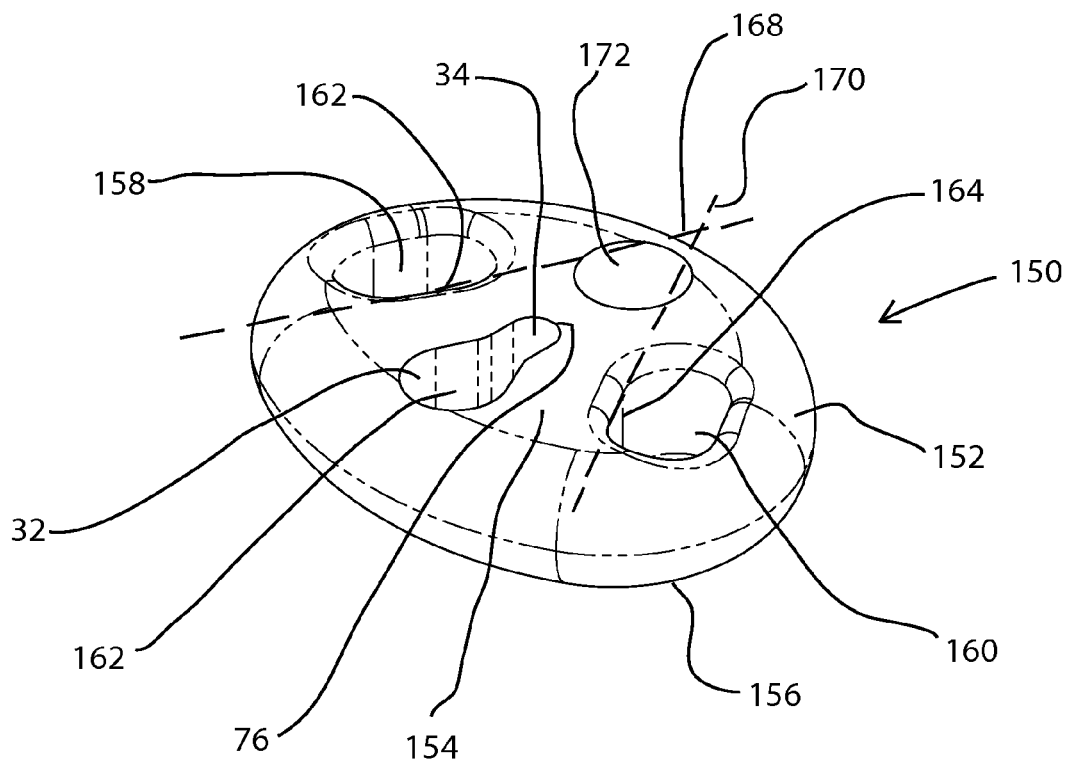
FIG. 11 is a perspective view of a line lock for use with a single strand of line.

Depicted in FIG. 11 is an alternative embodiment of a line lock 150 that is designed to slide along a single strand of line 100. Line lock 150 comprises a substantially disk shaped body 152 having a top surface 154 and an opposing bottom surface 156. Extending through body 152 between surfaces 154 and 156 is a primary passageway 158 and a spaced apart secondary passageway 160. Disposed between passageways 158 and 160 is a working passageway 162. Similar to line lock 10, working passageway 162 of line lock 150 has a first end with enlarged access region 32 and an opposing second end with constricted capture slot 34 thereat.

Primary passageway 158 and secondary passageway 160 have substantially the same elongated circular configuration which is similar to previously discussed secondary passageway 24. Each of passageways 158 and 160 has an inside face 162 and 164, respectively, that is disposed toward working passageway 162. Each inside face 162 and 164 is substantially disposed in or is tangent to a corresponding plane 168 and 170, respectively. Planes 168 and 170 converge toward capture slot 34 of working passageway 162 and diverge away from access region 32.

Also extending through body 152 between top surface 154 and bottom surface 156 is an end passageway 172. Although end passageway 172 can be positioned at a variety of different locations, end passageway 172 is shown aligned with working passageway 162 such that a plane extending between working passageway 162 and end passageway 172 separates primary passageway 158 from secondary passageway 160.

Figure 12A:
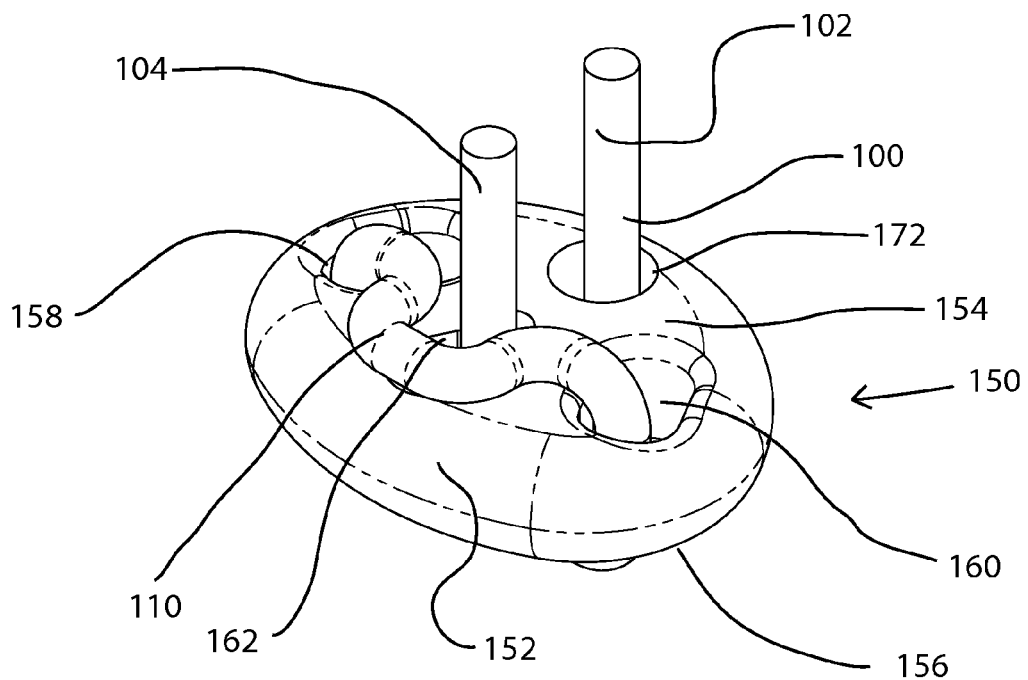
FIG. 12A is a perspective view of the line lock shown in FIG. 11 with a line routed therethrough.
Figure 12B:
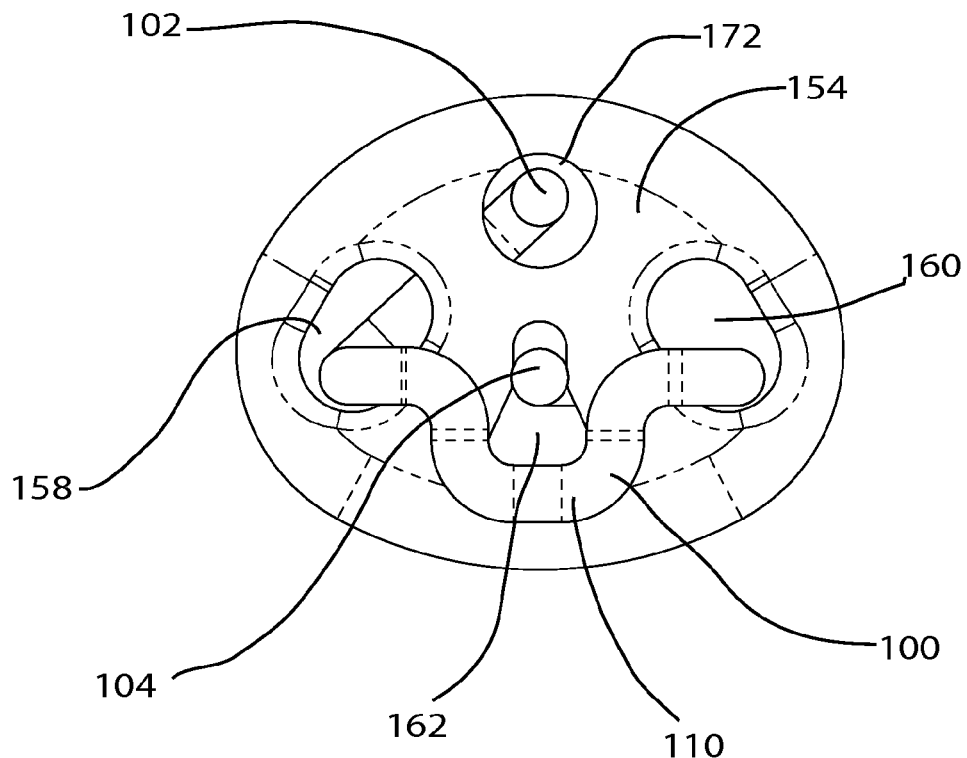
FIG. 12B is a top plan view of the line lock shown in FIG. 12A.
Figure 12C:
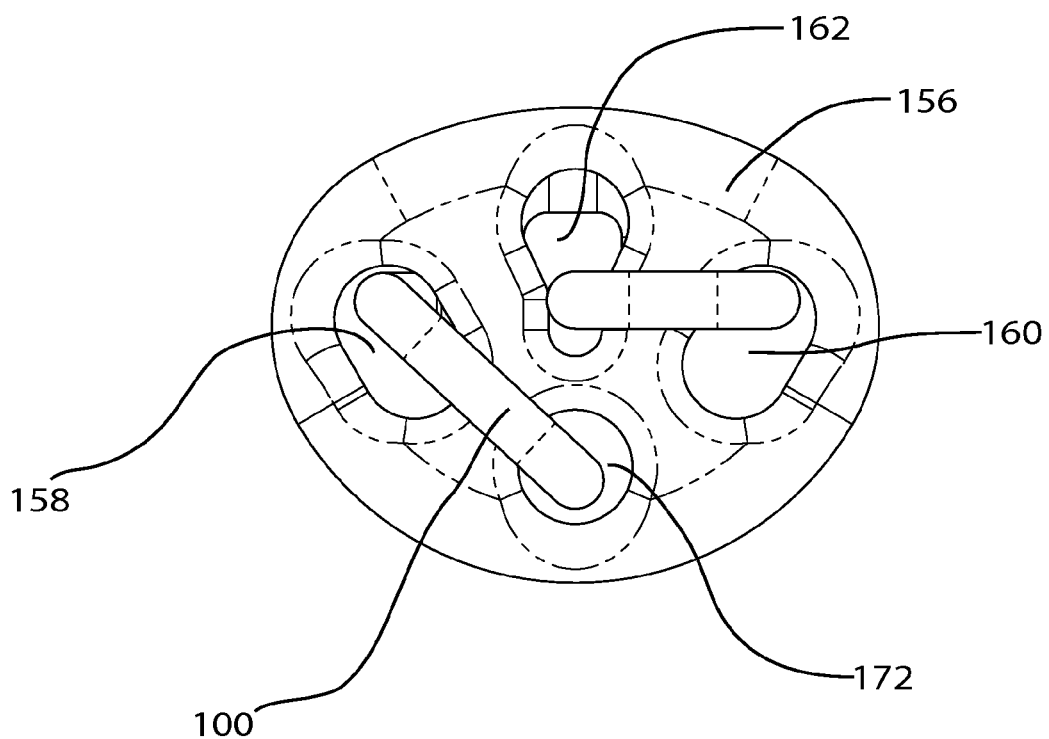
FIG. 12C is a bottom plan view of the line lock shown in FIG. 12A.

During use, as depicted in FIGS. 12A-12C, line 100 is routed through line lock 150 by passing working portion 104 from top surface 154 to bottom surface 156 through end passageway 172, up through primary passageway 158, down through secondary passageway 160, and finally up through working passageway 162. Compression portion 110 of line 100 extends between primary passageway 158 and secondary passageway 160 and is positioned to act upon working portion 104. Line lock 150 can be selectively advanced by pulling working portion 104 away from top surface 154 so that line 100 travels through line lock 150. Alternatively, line lock 150 can be manually slid toward standing portion 102. In either event, the length of standing portion 102 is decreased.

As line 100 is tensioned on line lock 150, line 100 locks on line lock 150 in substantially the same manner that line 100 locks with working passageway 28 as previously discussed with regard to line lock 10. That is, compression portion 110 forces working end 104 toward capture slot 34 so that the portion of line 100 within working passageway 162 is captured by wedged frictional engagement within capture slot 34. Furthermore, compression portion 110 either directly or indirectly biases working portion 104 against the top outside corner 76 of working passageway 162 at the second end thereof so as to increase the frictional engagement between line 100 and line lock 150. Line lock 150 thus provides a continuously adjustable line lock or a one way sliding stop. In alternative embodiments, it is appreciated that line lock 150 can be modified in at least the same ways as discussed with the other line locks disclosed herein.

The embodiment shown in FIGS. 12A-12C is advantageous in certain applications where line lock 150 is positioned behind a first object and working portion 104 and standing portion 102 pass through the first object. In this situation, standing portion 102 is fixed to a second object. By pulling on working portion 104, the first object is drawn irreversibly toward the second object. This is an advantage with surgical sutures where standing end 102 of a suture is attached to normal tissues and line lock 150 is placed behind tissue that has torn away. Standing portion 102 and working portion 104 pass through the torn tissue toward the normal tissue. By pulling on working portion 104 of suture, the torn tissue is pulled into apposition with the normal tissues and line lock 150 maintains the torn tissue adjacent to the normal tissue to facilitate healing of the tissue.

Figure 13A:
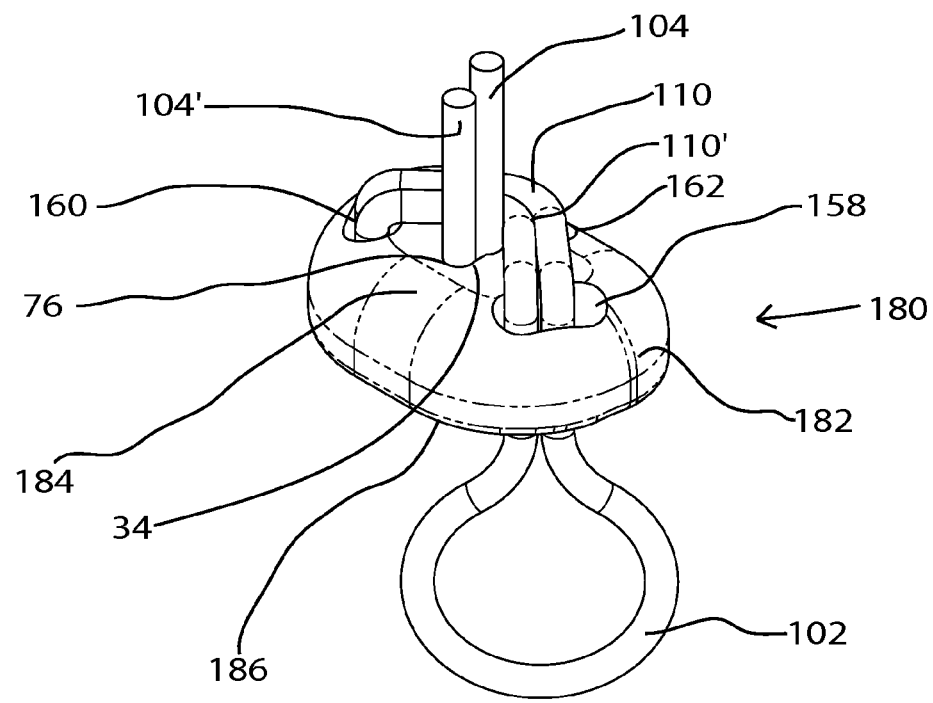
FIG. 13A is a top perspective view of a line lock having dual strands of line routed therethrough.
Figure 13B:
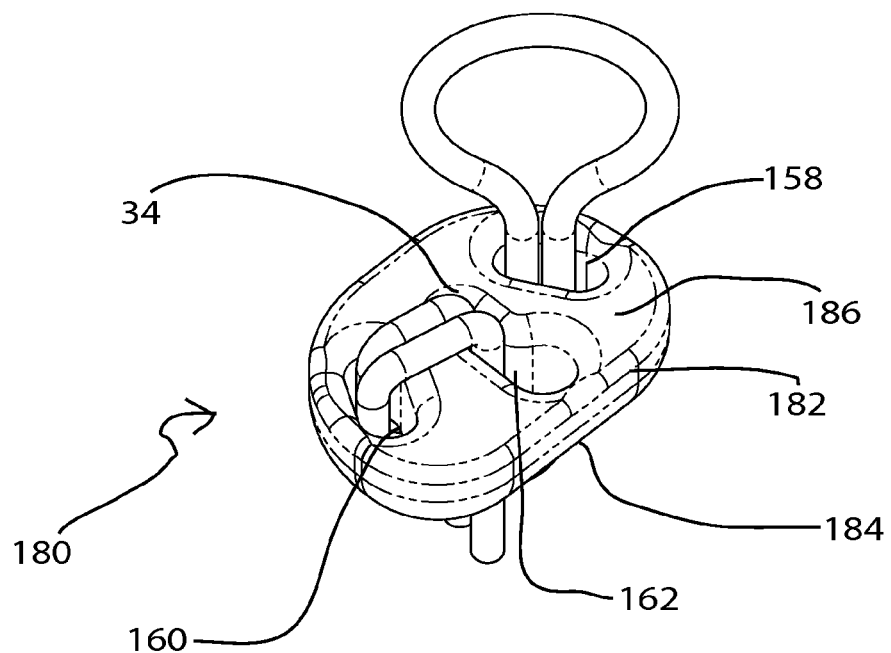
FIG. 13B is a bottom perspective view of the line lock shown in FIG. 13A.

Depicted in FIGS. 13A and 13B is another embodiment of a line lock 180 incorporating features of the present invention. Line lock 180 also comprises a substantially disk shaped body 182 having a top surface 184 and an opposing bottom surface 186. As with line lock 150, line lock 180 includes primary passageway 158, secondary passageway 160, and working passageway 162. Again, although not required, working passageway 162 is disposed such that a geometric line segment can be extended between primary passageway 158 and secondary passageway 160 so that the line segment intersects with working passageway 162. In contrast to line lock 150, line lock 180 does not include end passageway 172.

Each of passageways 158, 160, and 162 is configured to receive a double strand of line 100. Specifically, during use both working end 104 and 104' are passed up through primary passageway 158, down through secondary passageway 160 and then back up through working passageway 162. As a result, standing portion 102 is again formed in a loop that can be looped around, passed through, or otherwise secured to tissue or other structure. Unwanted slack is removed from standing portion 102 by again sliding line lock 180 on line 100 toward standing portion 102 and/or by pulling on one or both of working portions 104 and 104' so that line 100 passes through line lock 180.

When line 100 is tensioned on line lock 180, compression portions 110 and 110' force working portions 104, 104' toward capture slot 34 so that a portion of each line section passing through working passageway 162 is captured by wedged frictional engagement within capture slot 34. Compression portions 110 and 110' also bias working portions 104 and 104' toward and/or against top outsider corner 76 of working passageway 162 so as to increase the frictional engagement between line 100 and line lock 180. As previously discussed with passageways 22, 24, and 28 of line lock 10 in FIGS. 1-6, the radius of curvature of the top outside corner and bottom outside corner of each passageway 158, 160, and 162 can be set so as to further control the ability of line 100 to slide or not slide through the passageway. Other alternatives as discussed with the line locks herein are also applicable to line lock 180. In particular each of the passageways 158, 160, and 162 can also be configured to receive a single strand of line 100. In this configuration the single strand of line 100 is routed in a manner as described above for the double strand of line 100. Instead of the standing portion 102 forming a loop when a double strand of line 100 is used, in this case the standing portion 102 consists of a free end which can be attached to tissue or other structures.

Figure 14A:
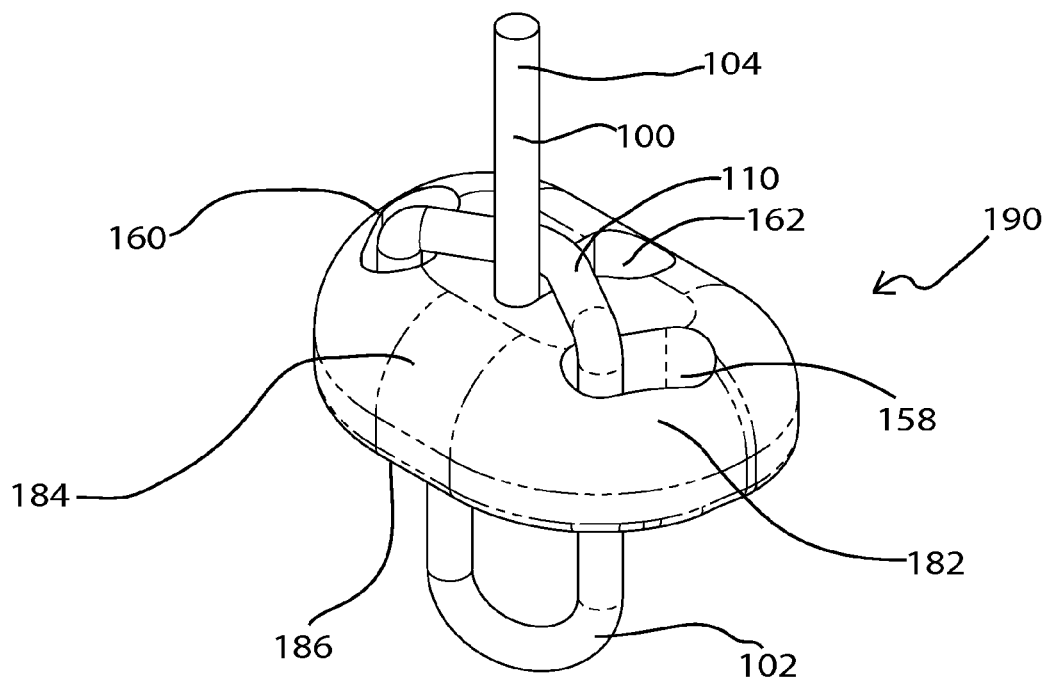
FIG. 14A is a top perspective view of a line lock having a line secured thereto.
Figure 14B:
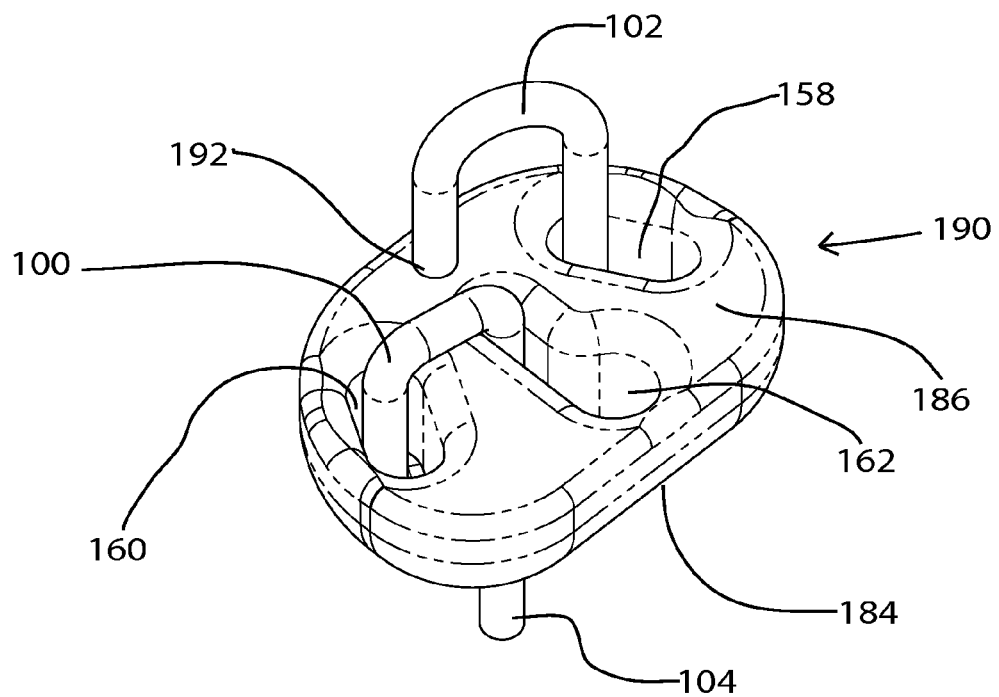
FIG. 14B is a bottom perspective view of the line lock shown in FIG. 14A.

Depicted in FIGS. 14A and 14B is still another embodiment of a line lock 190 incorporating features of the present invention. Line lock 190 has substantially the same configuration as line lock 180 with like elements being referenced with like reference characters. The primary distinction between line locks 180 and 190 is that in line lock 190, an end 192 of line 100 adjacent to standing portion 102 is secured to bottom surface 186 of body 182. End 192 can be secured to body 182 by being integrally molded into body 182 or can be otherwise secured such as by welding or mechanical attachment.

Line lock 190 is also distinguished from line lock 180 in that passageways 158, 160, and 162 need only be configured to receive a single strand of line 100. That is, working end 104 passes up through primary passageway 158, down through secondary passageway 160, and then back up through working passageway 162. Standing portion 102 is again substantially formed into a loop extending from end 192 of line 100 to primary passageway 158. Because end 192 of line 100 is secured to body 182, unwanted slack can be removed from standing portion 102 by pulling line 100 through line lock 190 and/or sliding line lock 190 down line 100. Line 100 is locked to line lock 190 in substantially the same manner as discussed above with regard to the other line locks when line 100 is tensioned on line lock 190.

And as previously described in U.S. application Ser. No. 11/001,866, after the working portion 104 has been inserted through or wrapped around the tissue to be retained, the line lock 190 may be advanced while holding the working portion 104 of the line 100 to tighten the standing portion 102. Alternatively, the line lock 190 may be held in place while pulling on the working portion 104. An insertion device (not shown) may be used to hold or advance the line lock 190.

As tension in the standing portion 102 increases, the compression section 110 tightens and presses the underlying working portion 104 against the body 182. The pressure on the working portion 104 keeps the working portion 104 from moving back into the working passageway 162, thereby keeping the standing portion 102 from loosening. Thus, the tissue will be securely retained by the standing portion 102, even after the working portion 104 has been cut short.

Pre-attachment of one end of a suture to a line lock, i.e., attachment of the suture prior to the surgical use, has a number of benefits. More specifically, it expedites installation of the suture and the line lock because separate sutures and line locks need not be located and assembled. As will be illustrated subsequently, a needle may also be pre-attached to the working end 104 of the line 100 so that all items needed for the suturing portion of the operation are ready for use. The line lock 190 may even be contained in a threader cartridge designed to facilitate insertion of the line 100 through the passageways 158, 160, 162 along the pattern illustrated. The configuration and use of such an assembly will be shown subsequently, in connection with FIG. 61.

In the embodiment of FIGS. 14A and 14B, the end 192 may advantageously be attached to the line lock 190 via insert molding. According to one manufacturing method, the end 192 is positioned within an injection mold (not shown) used to form the line lock 190. As the selected polymer fills the mold, it surrounds the end 192. Then, as the selected polymer cools and hardens, it captures the end 192 in a substantially permanent manner.

The present invention contemplates the use of any known attachment method, including but not limited to insert molding, adhesive bonding, knotting, ultrasonic welding, looping, swaging, and fastening via mechanical fasteners such as bolts and clips, and the like. FIGS. 54 through 59 provide examples of embodiments in which such alternative attachment methods are used.

Figure 15:
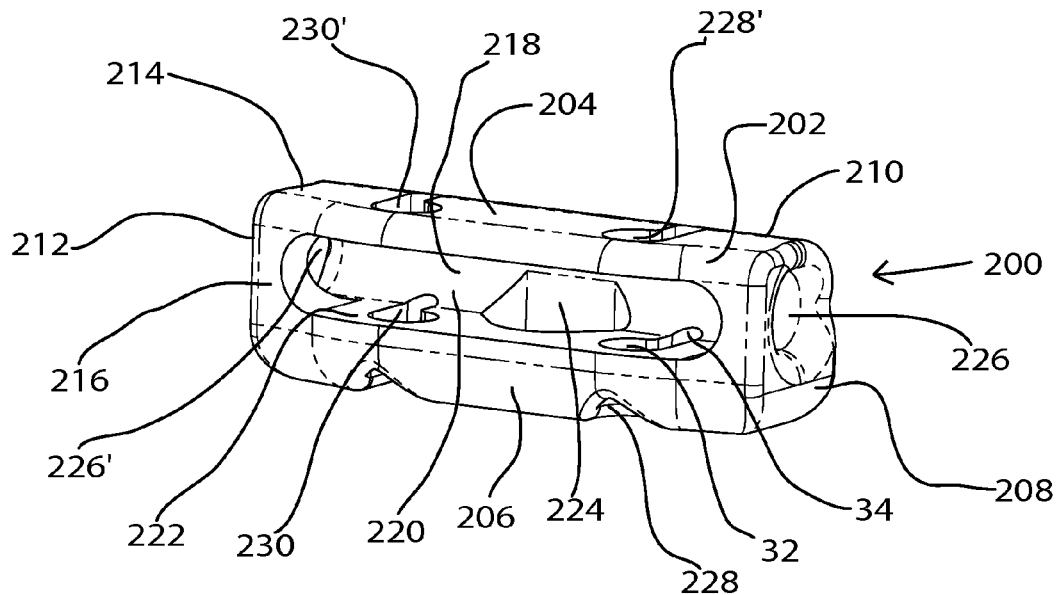
FIG. 15 is a perspective view of an alternative embodiment of a line lock.

Depicted in FIG. 15 is still another embodiment of a line lock 200 incorporating features of the present invention. Line lock 200 comprises an elongated substantially box shaped body 202 comprising a top wall 204 and an opposing bottom wall 206 each extending between a first side wall 208 and a first end 210 and an opposing second side wall 212 and an opposing second end 214. Also extending between top wall 204 and bottom wall 206 is a front wall 216 and an opposing back wall 218.

Partially bounded within body 202 is a hollow chamber 220. An access channel 222 is formed on front wall 216 so as to communicate with chamber 220. Also communicating with chamber 220 is a primary passageway 224. Primary passageway centrally extends through bottom wall 206 to chamber 220. A first secondary passageway 226 extends through first side wall 208 so as to communicate with chamber 220 while a second secondary passageway 226' extends through second side wall 212 so as to communicate with chamber 220. A pair of first working passageways 228 and 228' extend through bottom wall 206 and top wall 204, respectively, in vertical alignment between primary passageway 224 and first secondary passageway 226.

Similarly, a pair of second working passageways 230 and 230' extend through bottom wall 206 and top wall 204 in vertical alignment between primary passageway 224 and second secondary passageway 226'. As with the prior working passageways, each of working passageways 228, 228' and 230, 230' has a first end towards front wall 226 with an enlarged axis region 32 and an opposing second end toward back wall 218 with a capture slot 34 formed thereat.

Figure 16A:
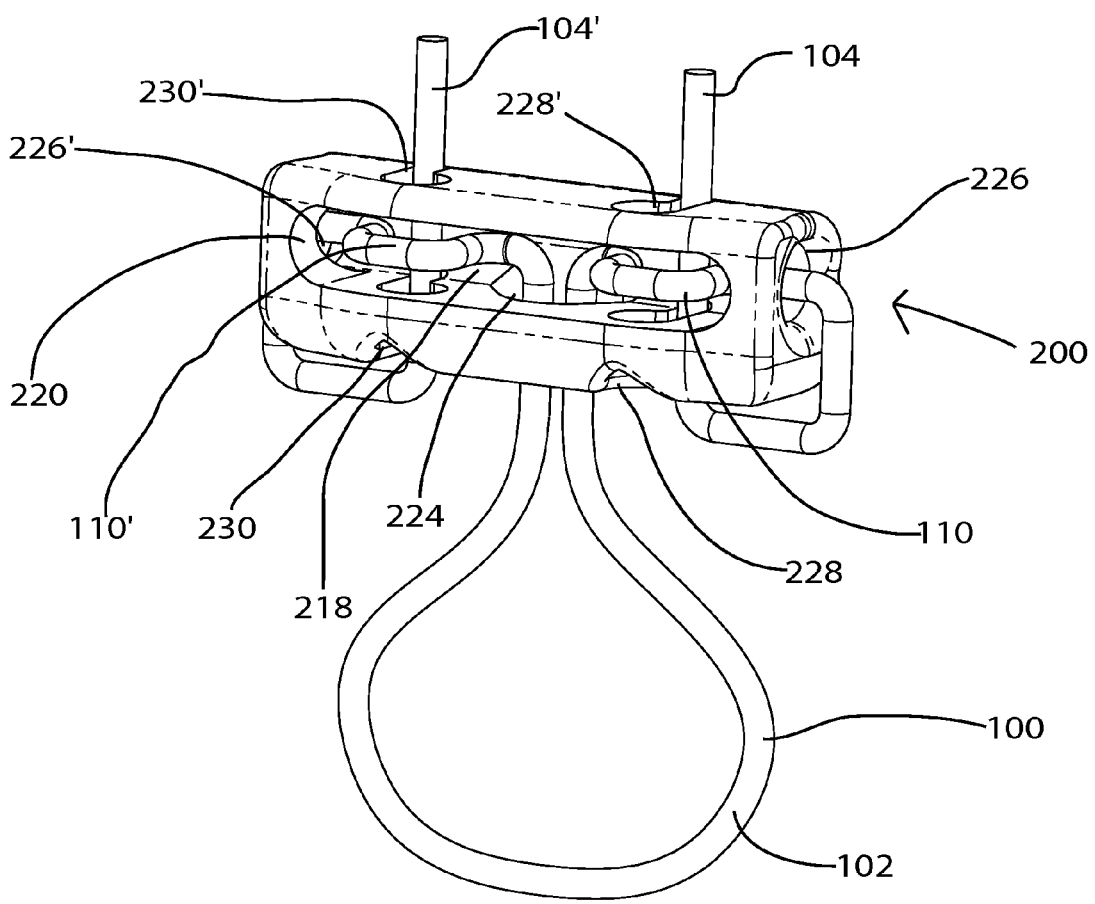
FIG. 16A is a perspective view of the line lock shown in FIG. 15 with a line routed therethrough.
Figure 16B:
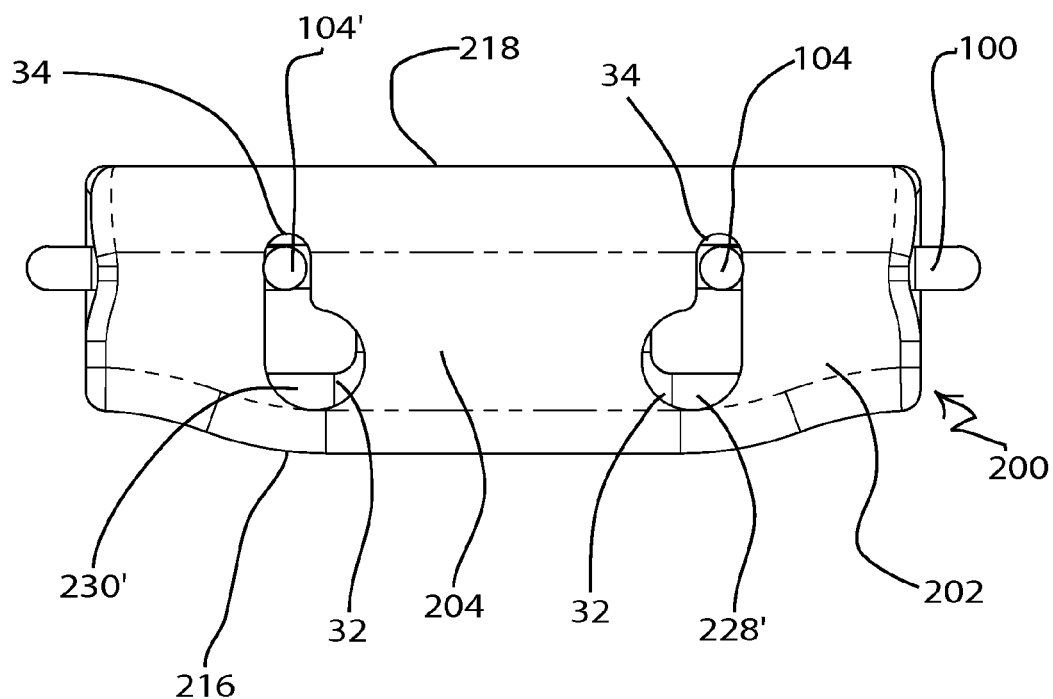
FIG. 16B is a top plan view of the line lock shown in FIG. 16A.
Figure 16C:
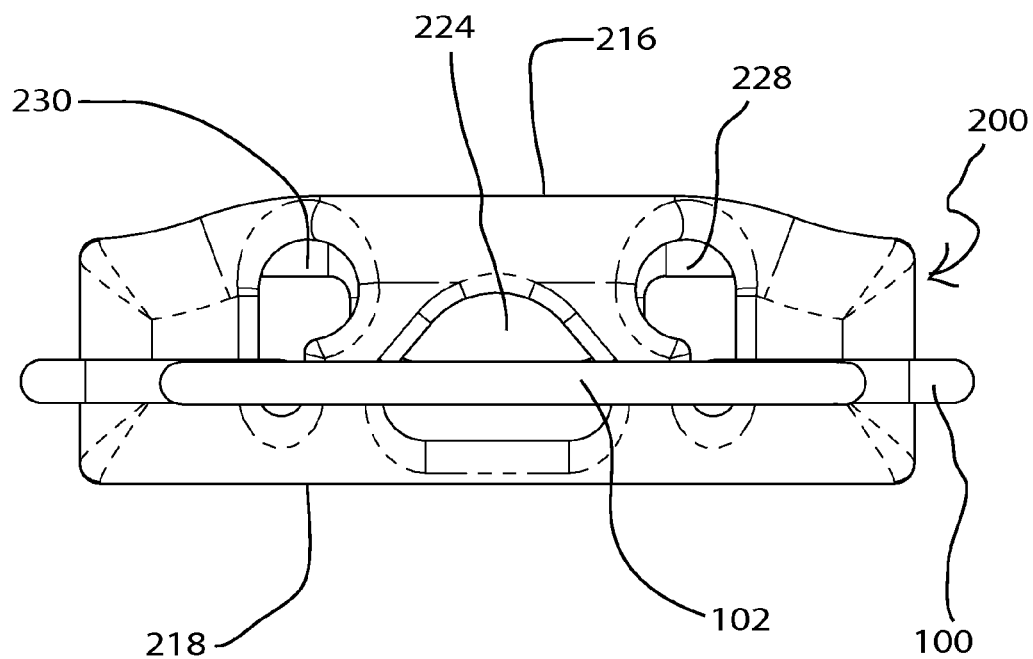
FIG. 16C is a bottom plan view of the line lock shown in FIG. 16A.

During use, as depicted in FIG. 16A-16C, working portions 104 of line 100 are passed up through primary passageway 224 into chamber 220. Working portion 104 then passes out of chamber 220 through first secondary passageway 226. Finally, working portion 104 passes up through first working passageway 228, through chamber 220, and then out through first working passageway 228'. Compression portion 110 of line 100 extends from primary passageway 224 to first secondary passageway 226. Working portion 104 is routed such that line 100 passes between compression portion 110 and back wall 218.

In like manner, working portion 104' extends from chamber 220 out through second secondary passageway 226'. Working portion 104' then extends up through second working passageway 230, through chamber 220, and then out through second working passageway 230'. Again, line 100 extends between compression portion 110' and back wall 218.

As with the other embodiments, line lock 200 can be slid along line 100 and/or line 100 can be pulled therethrough so as to remove all unwanted slack from standing portion 102. As line 100 is tension on line lock 200, compression portions 110 and 110' force the portion of line 100 extending between first working passageways 228 and 228' and between second working passageways 230 and 230', respectively, toward corresponding capture slots 34. As a result, at least a portion of line 100 extending through each of the working passageways is captured by frictional wedge engagement within each of the corresponding capture slots 34. Line 100 is thus locked with line lock 200.

Line lock 200 offers several advantages. When standing end 102 is slack and working ends 104 and 104' are tensioned, the sections of line 100 extending between working passageways 228 and 228' and between working passageways 230 and 230' force compression portions 110 and 110', respectively, back toward front wall 216 so as to allow the free travel of line 100 through line lock 200. In contrast, as discussed above, when tension is created in standing end 102 and slack is created in working ends 104 and 104', compression portions 110 and 110' force the sections of line 100 extending between working passageways 228 and 228' and between working passageways 230 and 230' toward back wall 218 so as to secure line 100 within the capture slots 34. This back and forth movement of compression portions 110 and 110' creates "backlash," or a finite distance that line lock 200 can move away from standing end 102 until locking of line 100 is achieved.

Top wall 204 of line lock 200 provides a physical constraint to the amount of movement seen in compression portions 110 and 110', thereby minimizing the amount of backlash. Furthermore, top wall 204 provides an additional friction point when compression portions 110 and 110' compress against line 100, thereby increasing the strength of the locking of line 100. That is, one friction point is located at working passageways 228 and 230 on bottom wall 206 and the second friction point is located at working passageways 228' and 230' on top wall 204.

It is again appreciated that the alternatives as discussed with the other embodiments are also applicable to line lock 200. By way of example and not by limitation, line 100 can be routed through line lock 200 in a manner analogous to the routing in FIG. 7. The various passageways can be open or closed as depicted in FIGS. 8 and 9. Similarly, line lock 200 can be divided in half and modified to function similar to the line locks shown in FIGS. 11-14.

Figure 17:
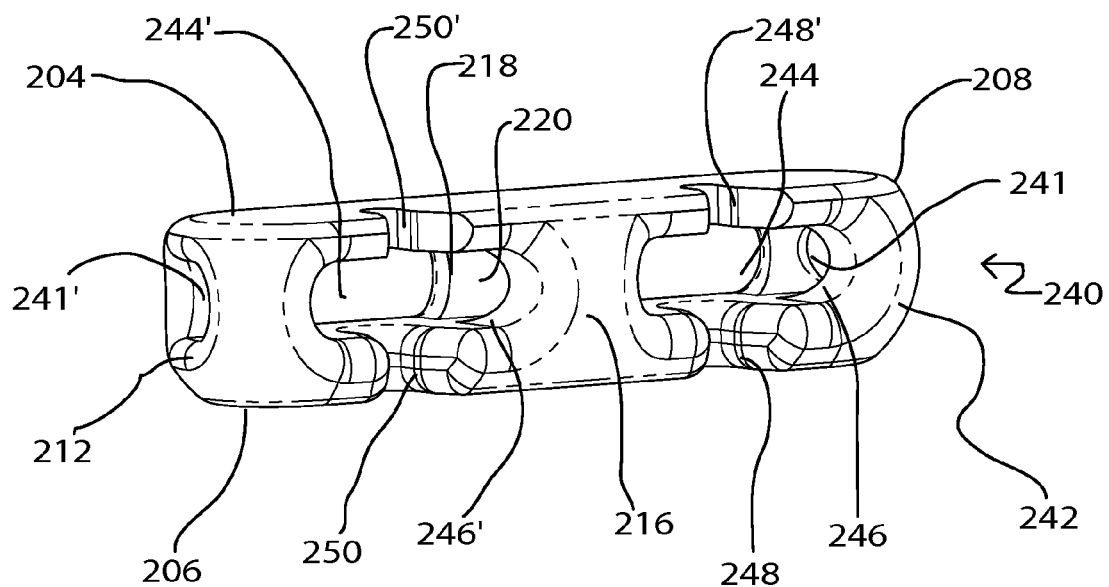
FIG. 17 is a perspective view of another alternative embodiment of a line lock.

Depicted in FIG. 17 is another alternative embodiment of a line lock 240 incorporating features of the present invention. Line lock 240 has a configuration similar to line lock 200 and thus like elements are identified by like reference characters. Line lock 240 comprises an elongated substantially box shaped body 242. Similar to line lock 200, body 242 comprises top wall 204 and bottom wall 206 extending between side wall 208 and side wall 212. Body 242 also includes front wall 216 and back wall 218 which partially bound chamber 220.

In contrast to line lock 200, a first primary passageway 241 extends through first side wall 208 while second primary passageway 241' extends through second side wall 212. Primary passageways 241 and 241' each communicate with chamber 220. Body 242 of line lock 240 further comprises a first secondary passageway 244 extending through back wall 218 in communication with chamber 220 and a spaced apart second secondary passageway 244' in communication with chamber 220. A first access port 246 extends through front wall 216 in alignment with first secondary passageway 244' so as to communicate with chamber 220. Similarly, a second access port 246' extends through front wall 216 in alignment with second secondary passageway 244 so as to also communicate with chamber 220.

Furthermore, in contrast to the bounded working passageways of line lock 200, line lock 240 comprises a pair of first working passageways 248 and 248'. Working passageway 248 comprises a constricting slot that is formed on bottom wall 206 and is open along intersecting front wall 216. First working passageway 248' is aligned with first working passageway 248 and is formed on top wall 204 so as to also be open along intersecting front wall 216. A pair of second working passageways 250 and 250' are similarly formed on bottom wall 206 and top wall 204 so as to be aligned with second secondary passageway 244'. Each of the working passageways terminates at capture slot having a width substantially equal to or smaller than the diameter of line 100.

Figure 18A:
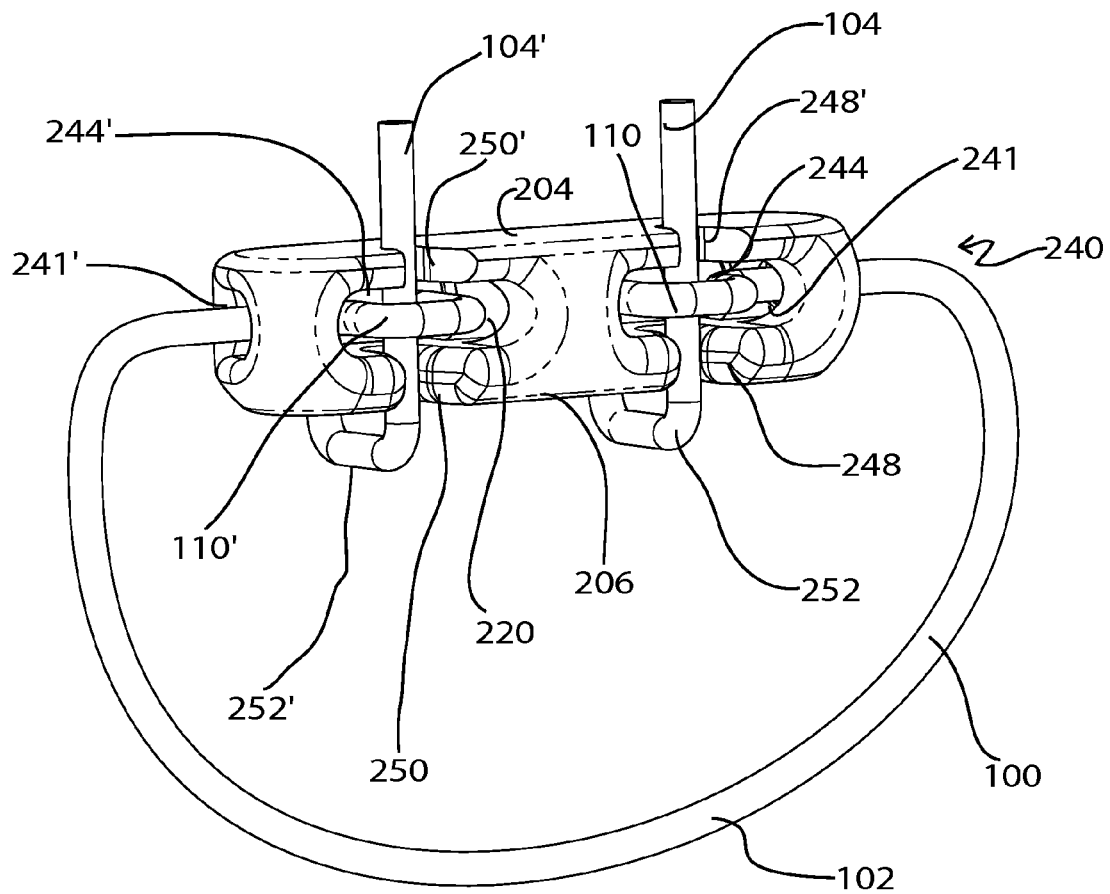
FIG. 18A is a perspective view of the line lock shown in FIG. 17 with a line routed therethrough.
Figure 18B:
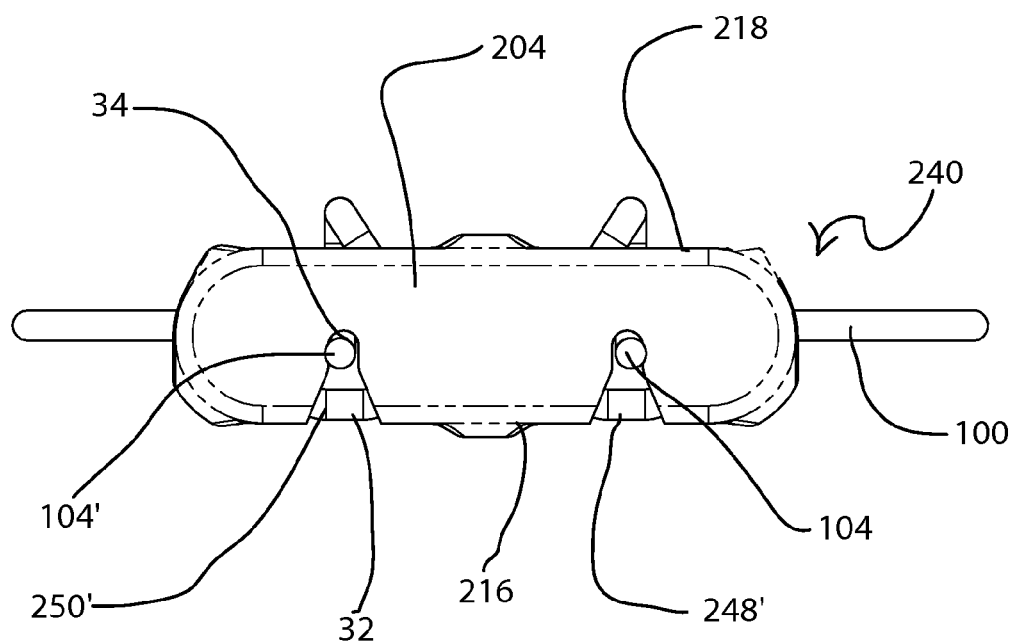
FIG. 18B is a top plan view of the line lock shown in FIG. 18A.
Figure 18C:
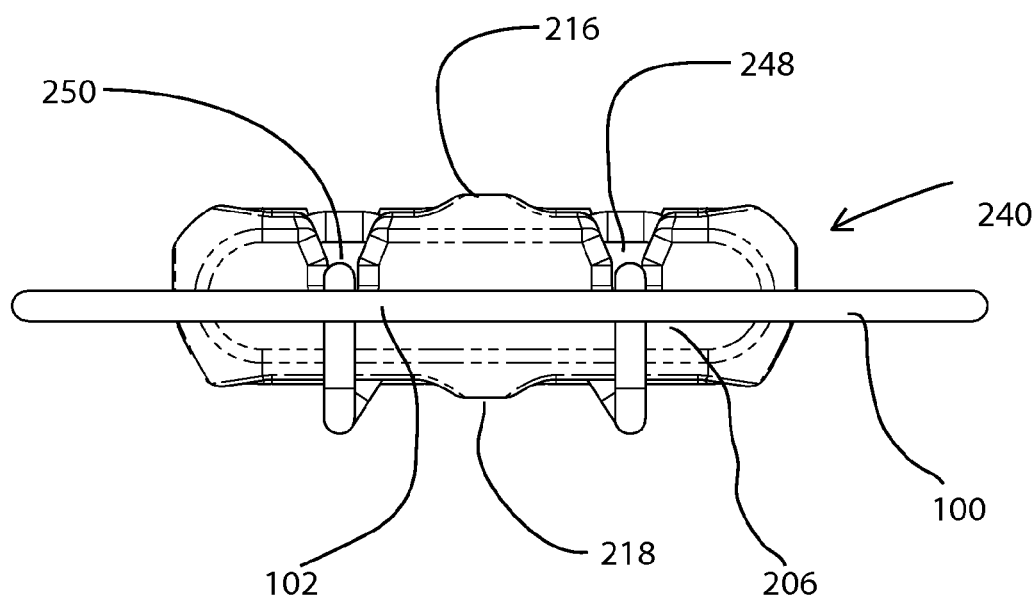
FIG. 18C is a bottom plan view of the line lock shown in FIG. 18A.

During use, as depicted in FIGS. 18A-18C, working end 104 of line 100 is passed through first primary passageway 242 into chamber 220 and then out through first secondary passageway 244. Working end 104 then passes down around bottom wall 206 and is then fed up through first working passageways 248 and 248'. A compression portion 110 of line 100 extends between primary passageway 241 and secondary passageway 244. Working portion 104 is passed between working passageways 248, 248' so that line 100 passes between compression portion 110 and first secondary passageway 244.

Working portion 104' is similarly passed through the passageways on the opposing side of line lock 240. That is, working portion 104' passes through primary passageway 241' and into chamber 220. Working portion 104' then travels out through secondary passageway 244', bends around bottom wall 206, and then travels up through working passageways 250 and 250'.

In the above configuration, slack can be removed from standing portion 102 by pulling line 100 through line lock 240 and/or sliding line lock 240 toward standing portion 102. As line 100 tensions on line lock 240, compression portions 110 and 110' again force portions of line 100 into capture slots 34 of the working passageways so as to secure line 100 to line lock 240 by wedged frictional engagement.

Like line lock 200, line lock 240 provides containment of compression portions 110 and 110' to minimize backlash. Unlike the other embodiments, line 100 is routed through line lock 240 such that at least one line turn exceeds 90 degrees. For example, the transition between compression portions 110 and 110' and looping portions, designated as 252 and 252', respectively, create 180 degree turns in line 100. These sharp bends in line 100 increase the friction that must be overcome in order to advance line lock 240 toward standing end 102. However, the sharp bends also contribute to greater locking strength of line lock 240 to line 100. This embodiment is beneficial when line 100 is monofilament or single strand line, due to the commonly lower line on line friction and greater flexural stiffness of monofilament line when compared to braided or twisted strand line.

Figure 19:
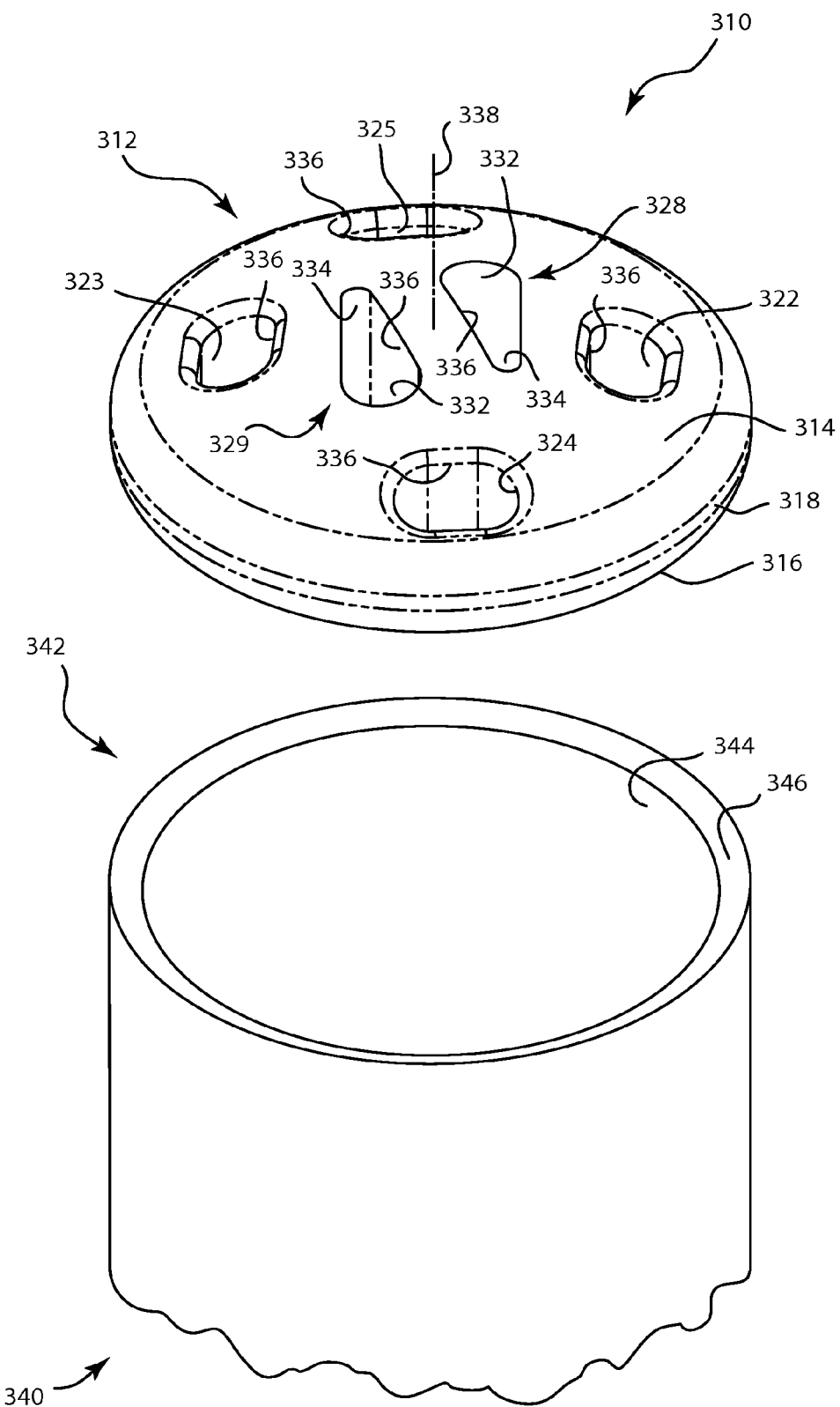
FIG. 19 is a perspective view of a line lock according to another alternative embodiment of the invention, with an associated insertion tool.

Referring to FIG. 19, a perspective view illustrates a line lock 310 according to one alternative embodiment of the invention. As shown, the line lock 310 has a body 312 that is generally disc-shaped. The body 312 has a top surface 314, a bottom surface 316, and a periphery 318 that extends between the top surface 314 and the bottom surface 316 to define a generally circular profile. In this application, a shape having a "generally circular profile" is any shape in which the outside boundary of any cross section passing through the main portion of the shape is substantially circular.

The body 312 bounds a plurality of passageways designed to cooperate receive a line such as a suture. In this application, passageways that "cooperate to receive" a line such as a suture receive the line such that the line passes through all of the cooperating passageways. The passageways of the body 312 include a first primary passageway 322 and a second primary passageway 323, each of which may be positioned adjacent to the periphery 318. The primary passageways 322, 323 are positioned on opposite sides of the body 312.

Furthermore, in the line lock 310 of FIG. 19, the passageways include a first secondary passageway 324 and a second secondary passageway 325, which are also positioned on opposite sides of the body 312, adjacent to the periphery 318. The secondary passageways 324, 325 may be positioned slightly closer to the periphery 318 than the primary passageways 322, 323. Yet further, the passageways also include a first working passageway 328 and a second working passageway 329. The working passageways 328, 329 are relatively centrally located with respect to the body 312.

Each of the primary and secondary passageways 322, 323, 324, 325 may be generally rounded, and may optionally be somewhat elongated to provide an oval cross-section capable of receiving a doubled-over suture end, as when a suture end (not shown) is inserted through a loop (not shown) and drawn through the primary and secondary passageways 322, 323, 324, 325 via the loop. Each of the working passageways 328, 329 may also have a cross-section broad enough to receive a doubled-over suture end.

The passageways 322, 323, 324, 325, 328, 329 intersect the top surface 314 to form corresponding openings, each of which is bounded by one of a plurality of top outside corners 336. The passageways 322, 323, 324, 324, 328, 329 also intersect the bottom surface 316 to form corresponding openings, each of which is bounded by one of a plurality of bottom outside corners (not shown).

As in the description previously set forth, some or all of the top outside corners 336 may have a smaller (i.e., sharper) radius than the corresponding bottom outside corners. More particularly, the top outside corners 336 of the working passageways 328, 329 may have comparatively small radii when compared to the bottom outside corners. In fact, in the embodiment of FIG. 19, the radii of the top outside corners 336 of the working passageways 328, 329 are considerably sharper than those of the top outside corners 336 of the primary and secondary passageways 322, 323, 324, 325. The sharp radii of the top outside corners 336 of the working passageways 328, 329 enhances locking of the suture by the line lock 310.

Each of the working passageways 328, 329 may have a shape that also facilitates locking of the suture, such as the teardrop-shaped cross-section illustrated in FIG. 19. More precisely, each of the working passageways 328 may have an access region 332 and a capture slot 334. The access region 332 is large enough to permit the suture to pass therethrough with clearance. However, the capture slot 334 may be somewhat narrower such that, when the suture is drawn into the capture slot 334, the walls of the capture slot 334 press against the suture to restrict further motion of the suture through the slot 334. The operation of the capture slot 334 will be further shown and described in connection with FIGS. 20 and 21.

In the embodiment of FIG. 19, the first primary, secondary, and working passageways 322, 324, 328 are symmetrically arranged about the center of the body 312 with respect to the second primary, secondary, and working passageways 323, 325, 329. In other words, the first primary, secondary, and working passageways 322, 324, 328 possess radial symmetry with respect to the second primary, secondary, and working passageways 323, 325, 329. Accordingly, if the first primary, secondary, and working passageways 322, 324, 328 were rotated 180° about a central axis 338 of the body 312, they would be substantially superimposed on the second primary, secondary, and working passageways 323, 325, 329.

According to one alternative embodiment, the capture slots 334 may extend at angles with respect to the access regions 332 so that the working passageways 328, 329 may be more compactly arranged, while keeping the capture slots 334 at the desired position and orientation with respect to the first primary and secondary passageways 322, 324 and with respect to the second primary and secondary passageways 323, 325. Such a configuration may potentially provide a more compact line lock (not shown) without losing suture locking capability.

In addition to the line lock 310, FIG. 19 also illustrates an insertion tool 340 that may be used to insert a line lock such as the line lock 310 of FIG. 19 into a relatively constricted space, such as a space within the body accessed via a cannula or the like. The insertion tool 340 has a proximal end (not shown), which may have handle or other structure to facilitate grasping by hand. The insertion tool 340 also has a distal end 342 and a hollow bore 344 that may extend along the entire displacement between the proximal end and the distal end 342 so that sutures or other items can be inserted into one end of the hollow bore 344 and retrieved from the opposite end. The distal end 342 has a rim 346, which may have an annular shape, a frustoconical shape, or the like, such that the body 312 is able to seat against the rim 346. The insertion tool 340 can thus be used to advance the line lock 310. The insertion tool 340 is illustrated proximate the bottom side 316 of the body 312 for clarity in FIG. 19; however, in use, the insertion tool 340 generally abuts the top side 314 and the periphery 318. The manner in which the insertion tool 340 is used to advance the line lock 310 will be more fully set forth in the description of FIG. 20.

Figure 20:
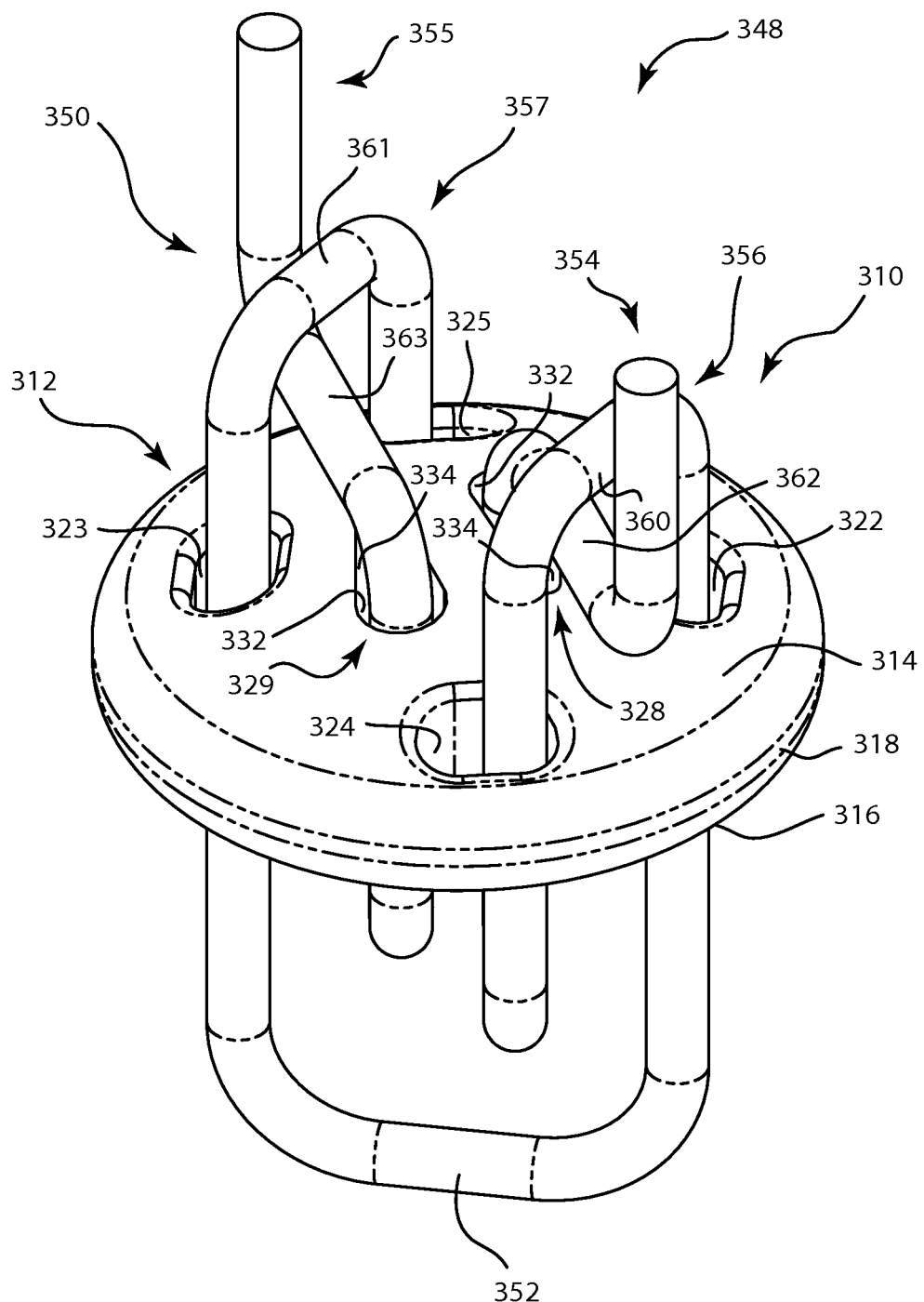
FIG. 20 is a perspective view of the line lock of FIG. 19, with a suture passing loosely through the passageways of the line lock.

Referring to FIG. 20, a perspective view illustrates a system 348 including the line lock 310 of FIG. 19 and a suture 350 relatively loosely passing through the passageways 322, 323, 324, 325, 328, 329 of the body 312. The suture 350 may be similar or identical to that described previously. Accordingly, the suture 350 may have a standing portion 352, which is the portion of the suture 350 that is placed under tension and constrained by advancement of the line lock 310, first and second working portions 354, 355, which are handled by a user, and first and second locking portions 356, 357 that are positioned between the standing portion 352 and the first and second working portions 354, 355, respectively.

The suture 350 may be inserted through the passageways 322, 323, 324, 325, 328, 329 according to a wide variety of methods. For example, the suture 350 may be inserted by hand. Alternatively, the suture 350 may be inserted through the use of threaders (not shown) that are initially routed through the passageways 322, 323, 324, 325, 328, 329 along the proper pathways. The threaders may have leading ends designed to be drawn by hand, and trailing ends with loops or other features capable of capturing and drawing the suture ends.

Thus, a user may simply attach the ends of the suture 350 to the trailing ends of the threaders, and then pull the threaders until the suture 350 passes through the passageways 322, 323, 324, 325, 328, 329 along the desired pathways. The ends of the suture 350 may then be removed from the trailing ends of the threaders. In addition to or in the alternative to the use of threaders, a cartridge (not shown) may be used to retain the line lock 310 and guide the suture 350 through the passageways 322, 323, 324, 325, 328, 329 along the desired pathways.

As illustrated in FIG. 20, the first locking portion 356 extends from the standing portion 352 through the first primary passageway 322, then through the first secondary passageway 324, and then through the first working passageway 328. From the first working passageway 328, the first working portion 354 extends between the top surface 314 and the section of the first locking portion 356 that passes from the first primary passageway 322 to the first secondary passageway 324. This section of the first locking portion 356 is a first compression section 360 of the suture 350.

Similarly, the second locking portion 357 extends from the standing portion 352 through the second primary passageway 323, then through the second secondary passageway 325, and then through the second working passageway 329. From the second working passageway 329, the second working portion 355 extends between the top surface 314 and the section of the second locking portion 357 that passes from the second primary passageway 323 to the second secondary passageway 325. This section of the second locking portion 357 is a second compression section 361 of the suture 350.

As shown in FIG. 20, the first and second working portions 354, 355 have first and second compressed sections 362, 363, respectively. The compressed sections 362, 363 underlie the corresponding compression sections 360, 361 of the first and second locking portions 356, 357, respectively. When the compression sections 360, 361 become taught, they press the compressed sections 362, 363 against the top surface 314 of the body 312. This will be explained in further detail subsequently.

The standing portion 352 may be inserted through and/or around some feature (not shown), such as bodily tissue, that is to be retained by the system 348. The standing portion 352 may additionally or alternatively pass through an opening of a bone anchor or the like to enable tissues to be anchored to the bone, as in rotator cuff repair. From the configuration of FIG. 20, the suture 350 may be tightened by advancing the line lock 310 along the standing portion 352. The line lock 310 may be advanced by holding the working portions 354, 355 and pressing the body 312 toward the standing portion 352.

According to one method, the line lock 310 may be advanced along the standing portion 352 through the use of a tool such as the insertion tool 340 of FIG. 19. More precisely, the working portions 354, 355 may first be inserted into the hollow bore 344 at the distal end 342. The working portions 354, 355 are inserted through the hollow bore 344 such that they protrude from the hollow bore 344 at the proximal end. A user may then grasp the working portions 354, 355 and draw them proximally, while holding the insertion tool stationary or advancing it distally, until there remains no slack in the working portions 354, 355, and the body 312 is seated against the rim 346 of the distal end 342. The shape of the rim 346 may tend to draw the body 312 into a position and orientation coaxial with the insertion tool 340 to facilitate insertion of the line lock 310 into a relatively narrow space.

Once the slack has been removed from the working portions 354, 355, further tension on the working portions 354, 355 tends to cause the locking portions 356, 357 to advance through the passageways 322, 323, 324, 325, 328, 329, moving from the primary passageways 322, 323 toward the working passageways 328, 329. Motion of the locking portions 356, 357 in this direction is relatively unrestricted since the compression sections 360, 361 remain slack, thereby allowing the locking portions 356, 357 to move through the access regions 332 of the working passageways 328, 329. Consequently, the line lock 310 is able to advance along the standing portion 352, thereby causing the standing portion 352 to tighten.

In alternative to use of a tool such as the insertion tool 340 of FIG. 19, the line lock 310 may be advanced along the standing portion 352 without any tooling. For example, the line lock 310 may be pressed and moved along the standing portion 352 by direct pressure from a finger. Alternatively, grasping the working portions 354, 355 and pulling them in substantially opposite and/or co-linear directions may cause the line lock 310 to advance along the standing portion 352. Each of the working portions 354, 355 may then lie along the top surface 314, but may not pass through the corresponding capture slot 334 until locking is performed. Such a technique may be particularly useful for retaining tissues in more readily accessible areas, where the working portions 354, 355 can be oriented and drawn in opposite directions. Use of insertion tooling may be more appropriate for more confined spaces.

Figure 21:
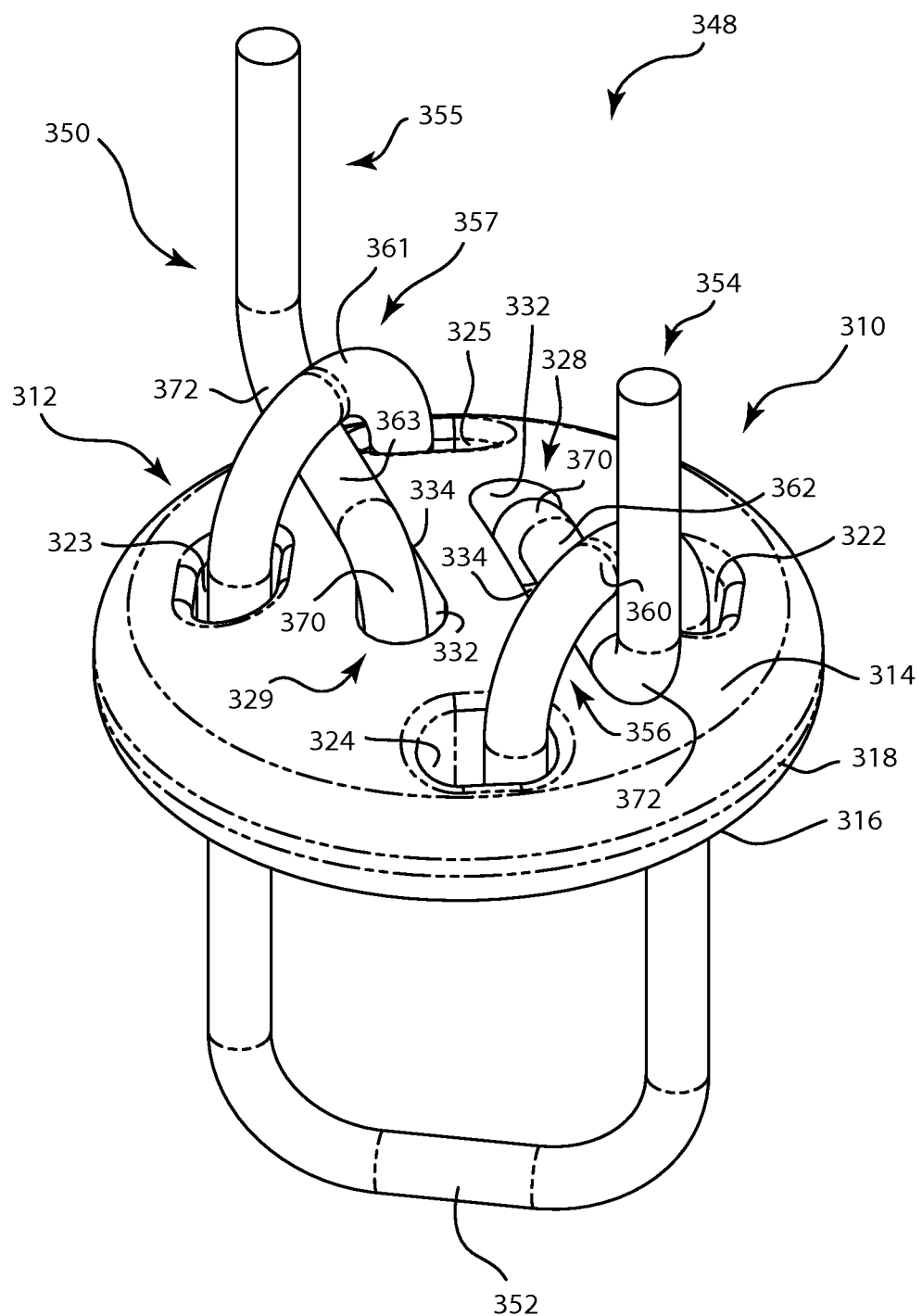
FIG. 21 is a perspective view of the line lock of FIG. 19, with the suture passing tightly through the passageways of the line lock.

Referring to FIG. 21, a perspective view illustrates the system 348 of FIG. 20, with the suture 350 routed relatively tightly through the passageways 322, 323, 324, 325, 328, 329. As the standing portion 352 tightens, tension in the standing portion 352 causes the compression sections 360, 361 to become taught. The compression sections 360, 361 straighten, thereby drawing the portions of the suture 350 within the working passageways 328, 329 outward, into the capture slots 334. The compressed sections 362, 363 of the working portions 354, 355 adjacent to the working passageways 328, 329 are pinned against the top surface 314 by the compression sections 360, 361.

Accordingly, each of the working portions 354, 355 is bent twice, with each bend having an angle of about ninety degrees. A first bend 370 is about the top outside corner 336 (as labeled in FIG. 19) of each corresponding working passageway 328, 329, and a second bend 372 is about the corresponding compression section 360, 361. As mentioned previously, the top outside corners 336 of the working passageways 328, 329 have tight radii. Accordingly, the top outside corners 336 of the working passageways 328, 329 provide relatively high friction surfaces, particularly when the working portions 354, 355 are pressed against them via tension, like that applied by the compression sections 360, 361. The compression sections 360, 361 may also provide considerable friction directly against the compressed sections 362, 363, depending on the structure and material of the suture 350.

Due to the friction applied to the bends 370, 372 of each of the working portions 354, 355 by the tensioned standing portion 352, the working portions 354, 355 are generally unable to retract back into the working passageways 328, 329. However, the standing portion 352 may still be tightened by further drawing on the working portions 354, 355. Tension in the working portions 354, 355 tends to pull the compression sections 360, 361 inward, thereby removing the bends 370, 372 and relieving the associated sources of friction. Further advancement of the body 312 along the standing portion 352 only increases the level of tension in the standing portion 352 so that, when tension on the working portions 328, 329 is relieved, the working portions 328, 329 are again drawn to the locked configuration.

After the locking portions 356, 357 have been locked via tension in the standing portion 352, the working portions 354, 355 may be cut short, for example, just outside the second bends 372. The friction on the bends 370, 372 keeps slippage to a level low enough that cutting the working portions 354, 355 in such a manner does not impair the operation of the line lock 310. The second bends 372 may disappear because there is no longer tension drawing the working portions 354, 355 to the orientation illustrated in FIG. 21. However, the second bends 372 are not required for locking; rather, the compression sections 360, 361 continue to press the compressed sections 362, 363 against the top surface 314, adjacent to the first bends 370. The friction of this compression interface, in addition to that of the first bends 370, is sufficient to keep the suture 350 from slipping back through the passageways 322, 323, 324, 325, 328, 329.

If desired, the line lock 310 and/or the suture 350 may be formed of bioabsorbable or biodegradable materials. Alternatively, the line lock 310 and the suture 350 may be small and compact enough that they can remain in the body indefinitely without causing any discomfort or significant health risks.

Figure 22:
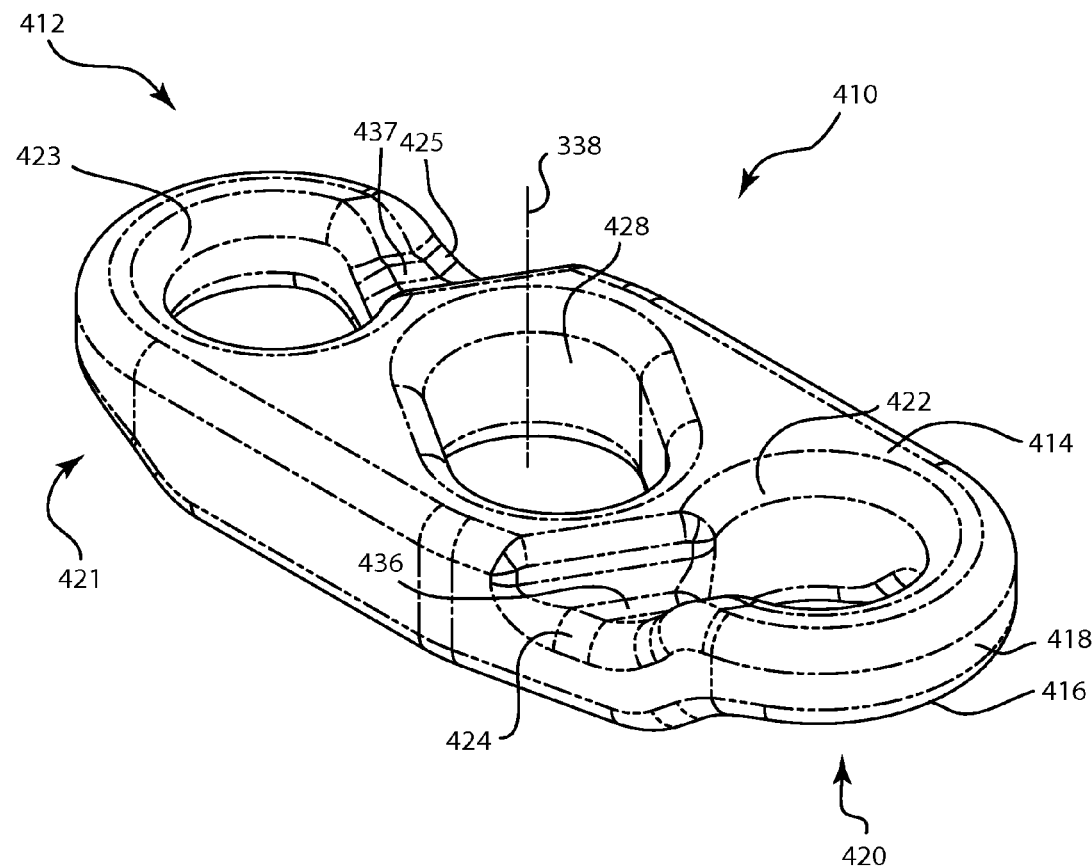
FIG. 22 is a perspective view of a line lock according to another alternative embodiment of the invention.

Referring to FIG. 22, a perspective view illustrates a line lock 410 according to another alternative embodiment of the invention. The line lock 410 has a body 412 that is generally elongated, and is compactly designed for less intrusive insertion into the body, and for more rapid bioabsorption. The body 412 has a top surface 414, a bottom surface 416, and a periphery 418 extending between the top surface 414 and the bottom surface 416 to provide the elongated profile of the body 412.

Furthermore, the body 412 is shaped to define a first primary passageway 422, a second primary passageway 423, a first secondary passageway 424, a second secondary passageway 425, and a first working passageway 428. The first and second primary passageways 422, 423 and the first working passageway 428 are all fully bounded. The first and second secondary passageways 424, 425 are each only partially bounded.

As mentioned previously, the term "passageway," as used in this application, is broadly interpreted to include partially bounded apertures, open channels, recesses, grooves, slots, and the like, that are capable of receiving a line and at least partially retaining the line therein. Accordingly, the structures labeled by reference numbers 424, 425 of FIG. 22 are, indeed, passageways. The secondary passageways 424, 425 are contiguous with the periphery 418 because the bore of each of the secondary passageways 424, 425 transitions directly into the periphery 418, with no significant intervening surface.

The first and second primary passageways 422, 423 are each generally circular in shape. The first working passageway 428 is designed to accommodate both locking portions 356, 357 of the suture 350 (not shown in FIG. 22), and is thus elongated in shape. The first working passageway is positioned between the first and second primary passageways 422, 423 such that the passageways 422, 423, 428 are arrayed in a generally straight line along the length of the body 412.

In FIG. 22, the first working passageway 428 has a generally rectangular shape, with semicircular arcs at the short ends. In alternative embodiments, any of a wide variety of shapes may be used, including trapezoidal, rectangular, square, triangular, circular, and oval shapes. If desired, alternative shapes may include one or more access regions and one or more capture slots, like those of the previous embodiment, that enhance suture locking.

The body 412 also defines a first groove 436 and a second groove 437, both of which are formed in the top surface 414. The first groove 436 extends along a generally straight path between the first primary and secondary passageways 422, 424. Similarly, the second groove 437 extends along a generally straight path between the second primary and secondary passageways 423, 425. The first and second grooves 436, 437 serve to enhance suture locking by the line lock 410 in a manner that will be set forth subsequently.

As shown in FIG. 22, the passageways 422, 423, 424, 425, 428 are symmetrical to each other about a central axis 338 of the body 412. This is because, if rotated 180° about the central axis 338, the first primary and secondary passageways 422, 424 would be superimposed on the second primary and secondary passageways 423, 425, and the first working passageway 428 would be superimposed on itself.

Figure 23:
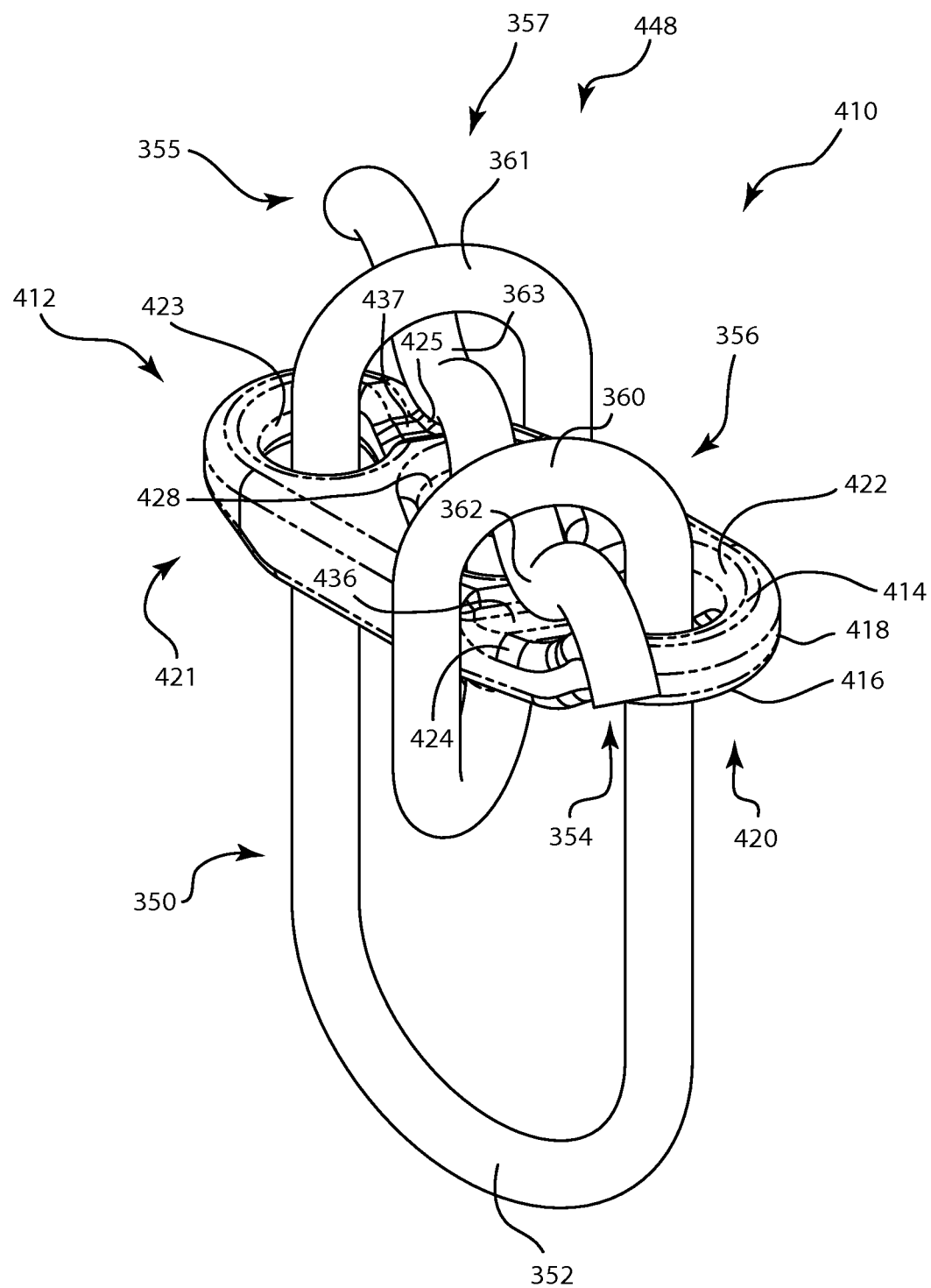
FIG. 23 is a perspective view of the line lock of FIG. 22, with a suture passing loosely through the passageways of the line lock.

Referring to FIG. 23, a perspective view illustrates a system 448 including the line lock 410 of FIG. 22 and a suture 350, like that illustrated in FIGS. 20 and 21. The suture 350 is shown routed relatively loosely through the passageways 422, 423, 424, 425, 428 of the line lock 410.

The suture 350 may be routed through the passageways 422, 423, 424, 425, 428 of the line lock 410 in a manner similar to that of the line lock 310. However, rather than being routed through two different working passageways 328, 329, the locking portions 356, 357 are both routed through the first working passageway 428. From the working passageway 428, the first compressed section 362 of the first working portion 354 extends between the first compression section 360 and the first groove 436, and the second compressed section 363 of the second working portion 355 extends between the second compression section 361 and the second groove 437.

Figure 24:
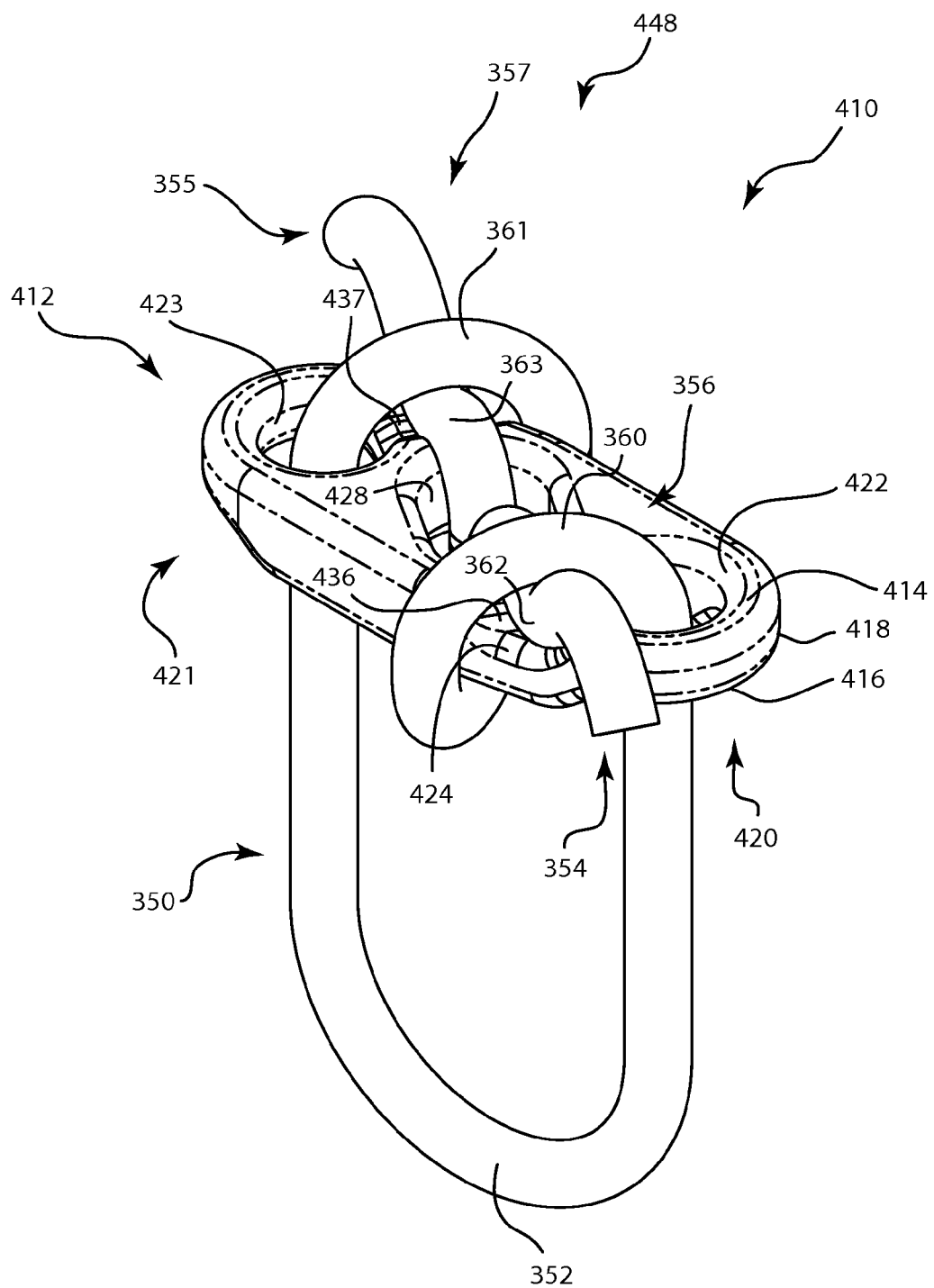
FIG. 24 is a perspective view of the line lock of FIG. 22, with the suture passing tightly through the passageways of the line lock.

Referring to FIG. 24, a perspective view illustrates the system 448 of FIG. 23, with the suture 350 routed relatively tightly through the passageways 422, 423, 424, 425, 428 of the line lock 410. The line lock 410 provides locking in a manner somewhat similar to that of the previous embodiment. More precisely, as the standing portion 352 of the suture 350 is tightened, tension is exerted on the compression sections 360, 361. The compression sections 360, 361 then press the compressed sections 362, 363, respectively, against the top surface 414 to cause the compressed sections 362, 363 to frictionally engage the grooves 436, 437, respectively. As shown, the compression sections 360, 361 may extend generally parallel to the grooves 436, 437 and the compressed sections 362, 363 may extend generally perpendicular to the grooves 436, 437. Accordingly, the working portions 354, 355 form bends where they extend across the grooves 436, 437. The bends enhance locking by adding to the frictional resistance to motion of the working portions 354, 355.

Other aspects of the operation of the line lock 410 are similar to those of the line lock 310 of the previous embodiment. The suture 350 may be inserted into the passageways 422, 423, 424, 425, 428, tightened, and locked within the line lock 410 in any of the ways set forth in connection with the previous embodiment. An insertion tool (not shown) similar to the insertion tool 340 of FIG. 19 may optionally be used to position the line lock 410 and/or move the line lock 410 along the locking portions 356, 357 of the suture 350. Such an insertion tool may have a distal end with an elongated shape that corresponds to that of the body 412 in order to facilitate secure retention of the body 412 against the distal end during the implantation procedure.

As described in connection with the previous embodiment, the working portions 354, 355 may be cut short after the suture 350 has been tightened and locked by the line lock 410. The line lock 410 may also be formed of a variety of bioabsorbable or non-bioabsorbable materials. The text setting forth potential suture threading methods, line lock advancement methods, materials, and the like for the line lock 310 may also apply to the line lock 410 and/or any other embodiment of the invention.

The line lock 410 has the advantage of being relatively compact. The overall dimensions of the body 412 are relatively small, and the volume occupied by the body 412 is also minimal. Accordingly, the line lock 410 may be easily implanted into relatively tight spaces, and if formed of a bioabsorbable material, may be readily absorbed by the body. The linear arrangement of the passageways 422, 423, 428 also keeps the line lock 410 from extending excessively along a direction transverse to that of the pathway followed by the suture 350. In alternative embodiments, only two substantially bounded passageways may be used instead of three. One such embodiment will be shown and described connection with FIGS. 25 through 27.

Figure 25:
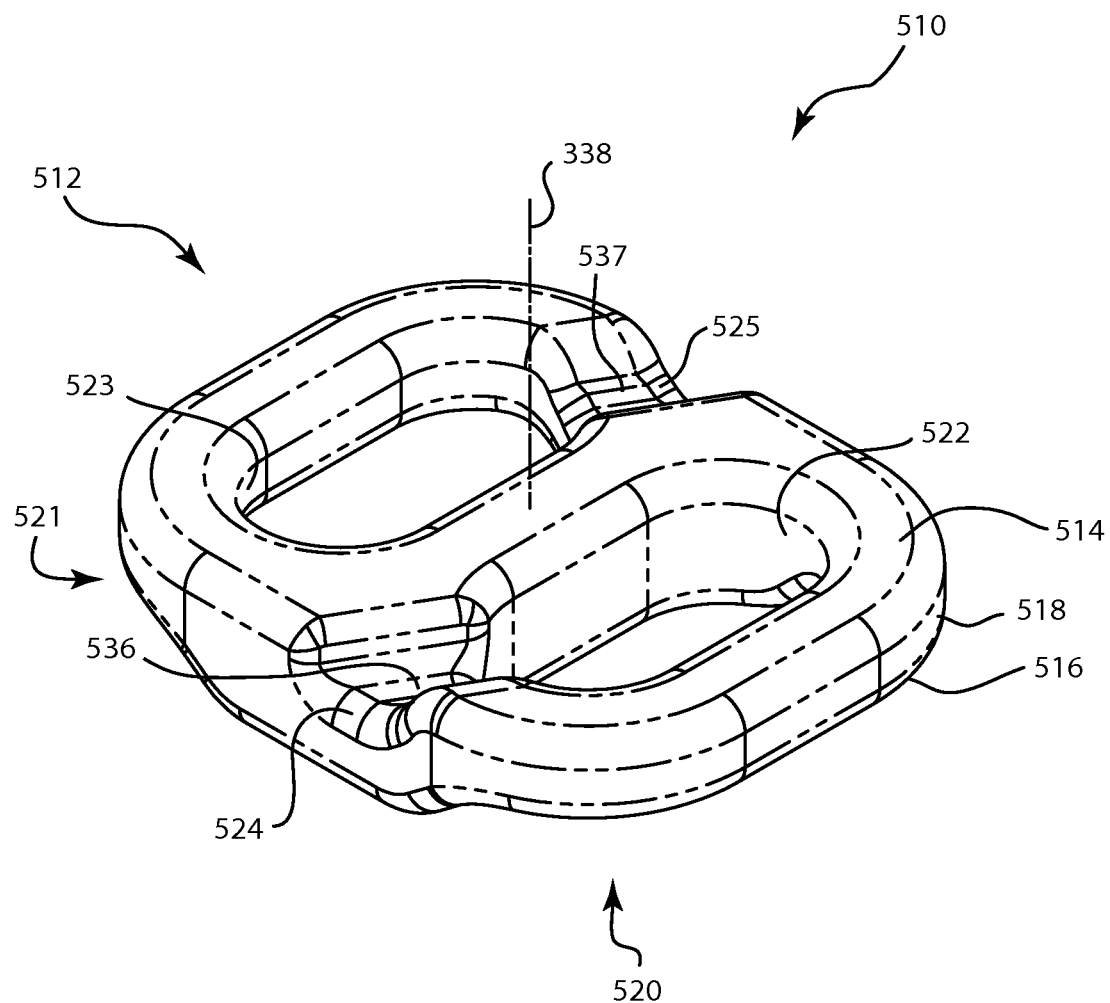
FIG. 25 is a perspective view of a line lock according to yet another alternative embodiment of the invention.

Referring to FIG. 25, a perspective view illustrates a line lock 510 according to another embodiment of the invention. As in the previous embodiment, the line lock 510 has a body 512 with an elongated shape. The body 512 has a top surface 514, a bottom surface 516, and a periphery 518 arranged between the top surface 514 and the bottom surface 516 to define the elongated profile of the body 512. The body 512 bounds a first primary passageway 522, a second primary passageway 523, a first secondary passageway 524, and a second secondary passageway 525. The first and second primary passageways 522, 523 are fully bounded, and the first and second secondary passageways 524, 525 are only partially bounded. No separate working passageway is needed.

The first and second primary passageways 522, 523 are each generally elongated in shape. Accordingly, each of the first and second primary passageways 522, 523 may receive both of the first or second locking portions 356, 357 of the suture 350 (not shown in FIG. 25). This enables the first and second primary passageways 522, 523 to perform the function carried out by the working passageway 428 of the previous embodiment, as will be shown in greater detail in connection with FIGS. 26 and 27.

The body 512 also defines a first groove 536 and a second groove 537, both of which are formed in the top surface 514. The first groove 536 extends along a generally straight path between the first primary and secondary passageways 522, 524. Similarly, the second groove 537 extends along a generally straight path between the second primary and secondary passageways 523, 525. The first and second grooves 536, 537 serve to enhance suture locking by the line lock 510 in a manner similar to the grooves 436, 437 of the previous embodiment.

As shown in FIG. 25, the passageways 522, 523, 524, 525 are symmetrical to each other about a central axis 338 of the body 512. This is because, if rotated 180° about the central axis 338, the first primary and secondary passageways 522, 524 would be superimposed on the second primary and secondary passageways 523, 525.

Figure 26:
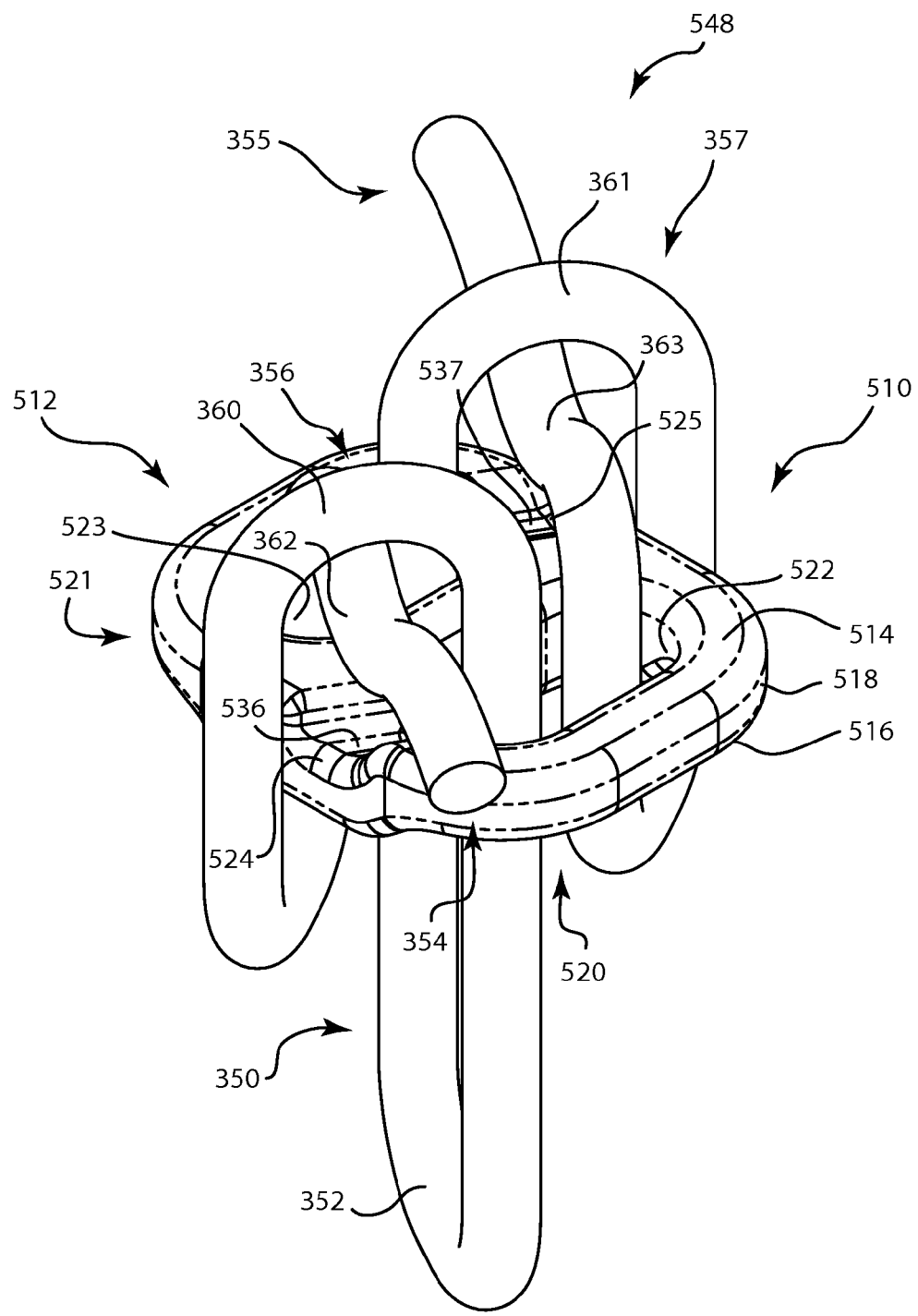
FIG. 26 is a perspective view of the line lock of FIG. 25, with a suture passing loosely through the passageways of the line lock.

Referring to FIG. 26, a perspective view illustrates a system 548 including the line lock 510 of FIG. 25 and a suture 350, like that illustrated in FIGS. 20, 21, 23, and 24. The suture 350 is shown routed relatively loosely through the passageways 522, 523, 524, 525 of the line lock 510.

The suture 350 may be routed through the passageways 522, 523, 524, 525 of the line lock 510 in a manner similar to that of the line lock 410. The first locking portion 356 passes through the first primary passageway 522, then the first secondary passageway 524. The second locking portion 357 passes through the second primary passageway 523, and then the second secondary passageway 525. Then, rather than passing through a working passageway 428, the locking portions 356, 357 are again routed through the first and second primary passageways 522, 523. More precisely, the first locking portion 356 passes through the second primary passageway 523, and the second locking portion 357 passes through the first primary passageway 522. From the second primary passageway 523, the first compressed section 362 of the first working portion 354 extends between the first compression section 360 and the first groove 536, and the second compressed section 363 of the second working portion 355 extends between the second compression section 361 and the second groove 537.

Figure 27:
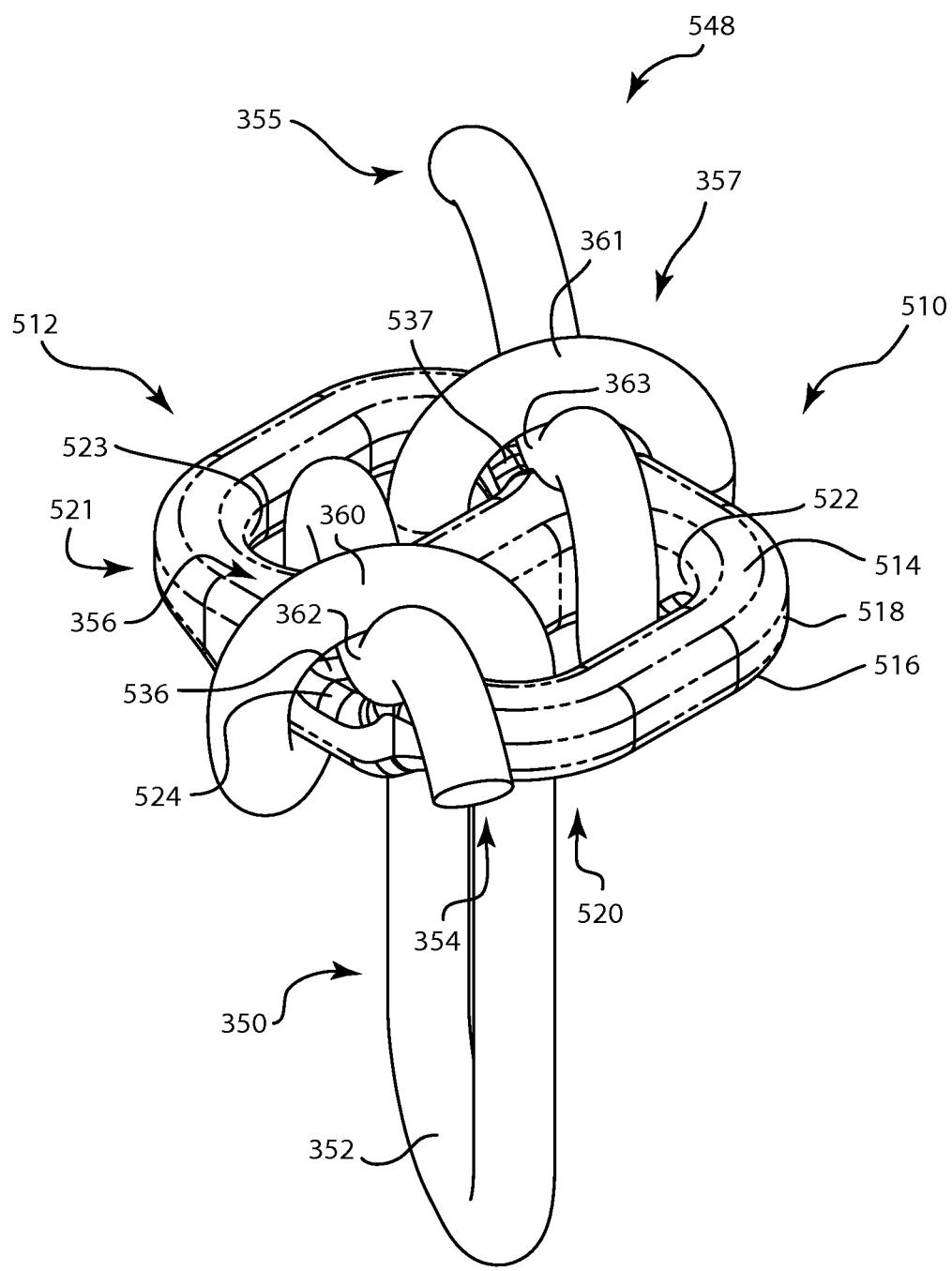
FIG. 27 is a perspective view of the line lock of FIG. 25, with the suture passing tightly through the passageways of the line lock.

Referring to FIG. 27, a perspective view illustrates the system 548 of FIG. 26, with the suture 350 routed relatively tightly through the passageways 522, 523, 524, and 525 of the line lock 510. The line lock 510 provides locking in a manner somewhat similar to that of the previous embodiment. More precisely, as the standing portion 352 of the suture 350 is tightened, tension is exerted on the compression sections 360, 361. The compression sections 360, 361 then press the compressed sections 362, 363, respectively, against the top surface 514 to cause the compressed sections 362, 363 to frictionally engage the grooves 536, 537, respectively. As shown, the compression sections 360, 361 may extend generally parallel to the grooves 536, 537 and the compressed sections 362, 363 may extend generally perpendicular to the grooves 536, 537. Accordingly, the working portions 354, 355 form bends where they extend across the grooves 536, 537. The bends enhance locking by adding to the frictional resistance to motion of the working portions 354, 355.

Other aspects of the operation of the line lock 510 are similar to those of the line locks 310, 410 of the previous two embodiments. The suture 350 may be inserted into the passageways 522, 523, 524, 525, tightened, and locked within the line lock 510 in any of the ways set forth in connection with the previous embodiment. An insertion tool (not shown) similar to the insertion tool 340 of FIG. 19 may optionally be used to position the line lock 510 and/or move the line lock 510 along the locking portions 356, 357 of the suture 350. Such an insertion tool may have a distal end with an elongated shape that corresponds to that of the body 512 in order to facilitate secure retention of the body 512 against the distal end during the implantation procedure.

As described in connection with the embodiment of FIGS. 19 through 21, the working portions 354, 355 may be cut short after the suture 350 has been tightened and locked by the line lock 510. The line lock 510 may also be formed of a variety of bioabsorbable or non-bioabsorbable materials. The text setting forth potential suture threading methods, line lock advancement methods, materials, and the like for the line lock 310 may also apply to the line lock 510 and/or any other embodiment of the invention.

And as previously described in U.S. application Ser. No. 10/936,376, referring to FIG. 28, a perspective view illustrates a line lock 1410 according to another alternative embodiment of the invention. As in the previous embodiment, the line lock 1410 has a body 1412 that is generally disc-shaped. The body 1412 has a top surface 1414, a bottom surface 1416, and a periphery 1418 extending between the top surface 1414 and the bottom surface 1416 to provide the generally circular profile of the body 1412. Furthermore, the body 1412 bounds a first primary passageway 1422, a second primary passageway 1423, a first secondary passageway 1424, and a second secondary passageway 1425. The first passageways 1422, 1424 possess multiple forms of symmetry with respect to the second passageways 1423, 1425, as will be described subsequently. The passageways 1422, 1423, 1424, 1425 are also adjacent to the periphery 1418.

In addition to the passageways 1422, 1423, 1424, 1425, the body 1412 bounds a first working passageway 1428. The first working passageway 428 has an access region 1432 and a pair of capture slots 1434 extending from either side of the access region 1432. The first working passageway 1428 accommodates both locking portions 356, 357 of the suture 350. Accordingly, the access region 1432 is large enough to simultaneously receive two suture portions with clearance, and each of the capture slots 1434 is sized to compress one of the suture portions.

The body 1412 also defines a first groove 1436 and a second groove 1437, both of which are formed in the top surface 1414. The first groove 1436 extends along a generally arcuate path between the first primary and secondary passageways 1422, 1424. Similarly, the second groove 1437 extends along a generally arcuate path between the second primary and secondary passageways 1423, 1425. The first and second grooves serve to provide a pair of sharpened lips 1438 adjacent to each of the capture slots 1434 of the first working passageway 1428.

Figure 28:
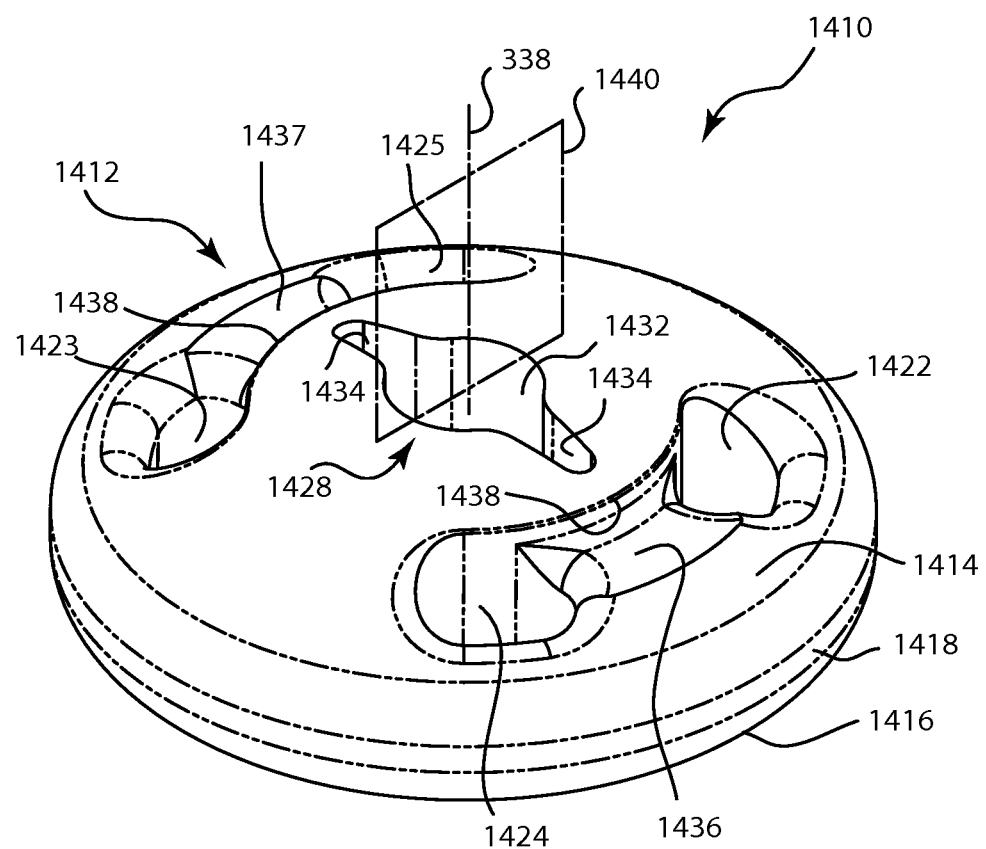
FIG. 28 is a perspective view of a line lock according to another alternative embodiment of the invention.

As shown in FIG. 28, the passageways 1422, 1423, 1424, 1425, 1428 are symmetrical to each other about a central axis 338 of the body 1412. This is because, if rotated 180° about the central axis 338, the first primary and secondary passageways 1422, 1424 would be superimposed on the second primary and secondary passageways 1423, 1425, and the first working passageway 1428 would be superimposed on itself. Furthermore, the passageways 1422, 1423, 1424, 1425, 1428 are symmetrical to each other about a plane 1440 passing through the center of the body 1412. This is because, if reflected across the plane 1440, the first primary and secondary passageways 1422, 1424 would be superimposed on the second primary and secondary passageways 1423, 1425, and the first working passageway 1428 would be superimposed on itself.

The suture 350 may be routed through the passageways 1422, 1423, 1424, 1425, 1428 of the line lock 1410 in a manner similar to that of the line lock 310. However, rather than being routed through two different working passageways 328, 329, the locking portions 356, 357 are both routed through the first working passageway 1428. From the working passageway 1428, the first working portion 354 extends between the first compression section 360 and the first groove 1436, and the second working portion 355 extends between the second compression section 361 and the second groove 1437.

The line lock 1410 provides locking in a manner somewhat similar to that of the previous embodiment. More precisely, when the compression sections 360, 361 press the working portions 354, 355, respectively, against the top surface 1414, the suture 350 becomes wedged in the capture slots 1434. Additionally, the compression sections 360, 361 press the working portions 354, 355 against the grooves 1436, 1437, respectively. As shown, the compression sections 360, 361 may extend generally parallel to the grooves 1436, 1437 and the working portions 354, 355 may extend generally perpendicular to the grooves 1436, 1437. Accordingly, the working portions form bends (not shown) where they extend over the sharpened lips 1438 of the grooves 1436, 1437. The sharpened lips 1438 provide additional friction tending to resist motion of the working portions 354, 355 toward the first working passageway 1428.

Otherwise, operation of the line lock 1410 is similar to that of the line lock 310 of the previous embodiment. The suture 350 may be inserted into the passageways 1422, 1423, 1424, 1425, 1428, tightened, and locked within the line lock 1410 in any of the ways set forth in connection with the previous embodiment. As described above, the working portions 354, 355 may be cut short after the suture 350 has been tightened and locked by the line lock 410. The line lock 1410 may also be formed of a variety of biodegradable or non-biodegradable materials. The text setting forth potential suture threading methods, line lock advancement methods, materials, and the like for the line lock 310 may also apply to the line lock 1410 and/or any other embodiment of the invention.

Figure 29:
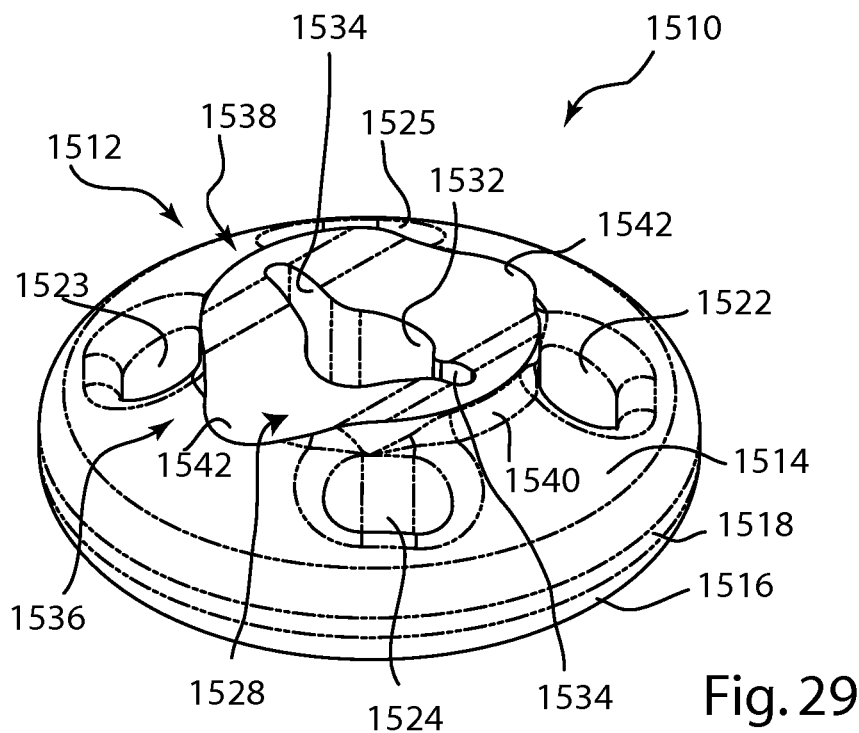
FIG. 29 is a perspective view of a line lock according to another alternative embodiment of the invention.

Referring to FIG. 29, a perspective view illustrates a line lock 1510 according to another embodiment of the invention. As in the previous embodiment, the line lock 1510 has a body 1512 with a disc-like shape. The body 1512 has a top surface 1514, a bottom surface 1516, and a periphery 1518 arranged between the top surface 1514 and the bottom surface 1516 to define the circular profile of the body 1512. The body 1512 bounds a first primary passageway 1522, a second primary passageway 1523, a first secondary passageway 1524, a second secondary passageway 1525, and a first working passageway 1528.

As in the previous embodiment, the first working passageway 1528 has an access region 1532 and a pair of oppositely disposed capture slots 1534. However, in place of the grooves 1436, 1437 of the previous embodiment, the body 1512 has a central plateau 1536 around which the primary and secondary passageways 1522, 1523, 1524, 1525 are arranged. The first working passageway 1528 extends through the central plateau 1536.

The central plateau 1536 may be somewhat tapered so as to form a sharpened rim 1538. The central plateau 1536 has a concave surface 1540 that passes along a generally circular pathway between the sharpened rim 1538 and the remainder of the body 1512. The sharpened rim 1538 has a pair of ears 1542 that extend between the first primary passageway 1522 and the second secondary passageway 1525, and between the second primary passageway 1523 and the first secondary passageway 1524. The top surface of the central plateau 1536 elevates as it extends outward, along the capture slots 1534.

The suture 350 may be routed through the passageways 1522, 1523, 1524, 1525, 1528 of the line lock 1510 in a manner similar to that of the line lock 1410 of the previous embodiment. Accordingly, both locking portions 356, 357 of the suture 350 will extend through the first working passageway 1528. The first working portion 354 will extend from the first working passageway 1528 to lie along the central plateau 1536 and the top surface 1514 between the first primary and secondary passageways 1522, 1524. The second working portion 355 will extend from the first working passageway 1528 to lie along the central plateau 1536 and the top surface 1514 between the second primary and secondary passageways 1523, 1525.

When the standing portion 352 is tensioned, the compression sections 360, 361 will compress the working portions 354, 355 against the sharpened rim 1538 of the central plateau 1536, thereby forming bends and applying friction to keep the working portions 354, 355 from moving back toward the first working passageway 1528. The sharpened rim 1538 effectively forms a function similar to that of the sharpened lips 1438 of the grooves 1436, 1437 of the previous embodiment. The compression sections 360 may tend to slide outward to either side of the central plateau 1536 to enhance the bends formed in the working portions 354, 355.

Figure 30:
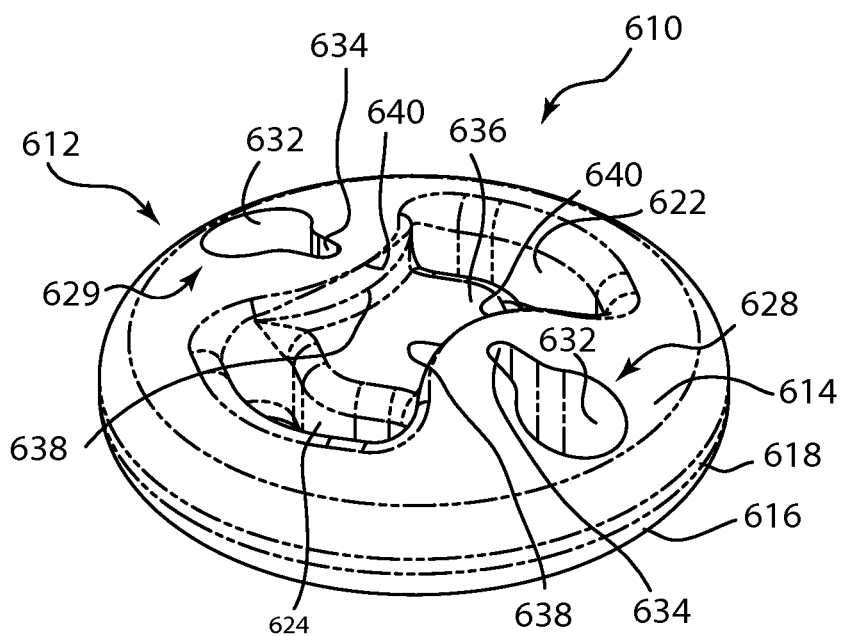
FIG. 30 is a perspective view of a line lock according to another alternative embodiment of the invention.

Referring to FIG. 30, a perspective view illustrates a line lock 610 according to another alternative embodiment of the invention. The line lock 610 has a body 612 with a disc-like shape. The body 612 has a top surface 614, a bottom surface 616, and a periphery 618 that extends between the top surface 614 and the bottom surface 616 to define the generally circular profile of the body 612. The body 612 bounds a first primary passageway 622 and a first secondary passageway 624, but no second primary or secondary passageways. The first primary and secondary passageways 622, 624 are generally arc-shaped, and each of the first primary and secondary passageways 622, 624 is broad enough to accommodate multiple passes of the suture 350.

The body 612 also bounds a first working passageway 628 and a second working passageway 629. The working passageways 628, 629 may be shaped similarly to the working passageways 328, 329 of the embodiment of FIG. 19, in that each of the working passageways 628, 629 has a keyhole-like shape with an access region 632 sized to permit passage of the suture 350 with clearance, and a capture slot 634 sized to grip the suture 350. The capture slots 634 are oriented inward, toward the center of the body 612.

The body 612 also has a central depression 636 positioned between the first primary and secondary passageways 622, 624. The central depression 636 may have a bowtie-like shape. The central depression 636 has side walls 638 that extend generally perpendicular to the top surface 614. Sharpened edges 640 are formed by the intersection of the side walls 638 with the top surface 614. The sharpened edges 640 serve to enhance locking of the suture 350 in a manner that will be set forth in connection with FIGS. 31 and 32.

Figure 31:
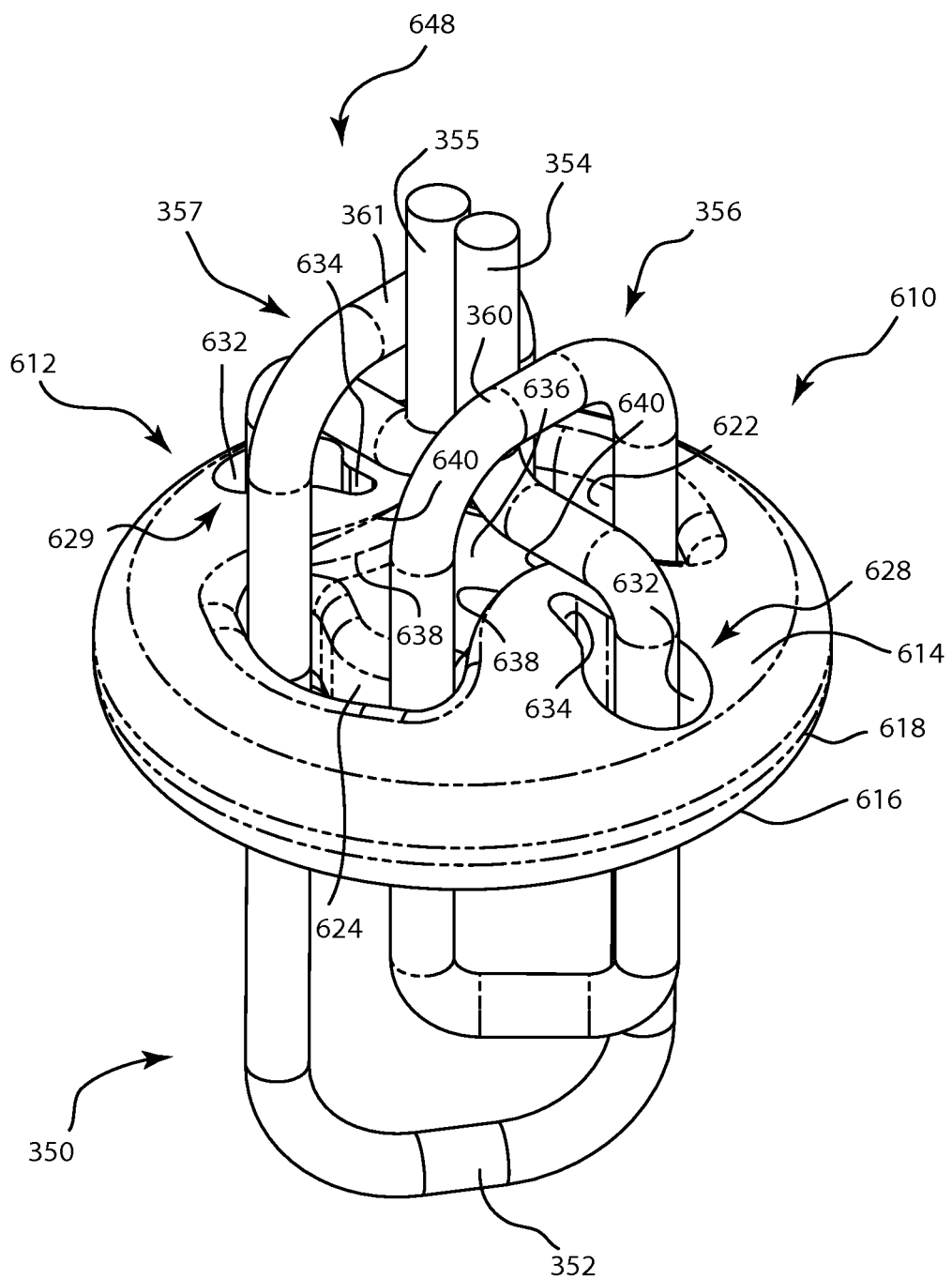
FIG. 31 is a perspective view of the line lock of FIG. 30, with a suture passing loosely through the passageways of the line lock.

Referring to FIG. 31, a perspective view illustrates a system 648 including the line lock 610 and the suture 350 passing through the passageways 622, 624, 628, 629 in a relatively loose configuration. As shown, the first locking portion 356 passes first through the first primary passageway 622, and then through the first secondary passageway 624 to define the first compression section 360. The second locking portion 357 passes first through the first secondary passageway 624 and then through the first primary passageway 622 to define the second compression section 361.

From the first secondary passageway 624, the first locking portion 356 passes through the first working passageway 628, and the first working portion 354 extends from the first working passageway 628, between the top surface 614 and the first compression section 360. Similarly, from the first primary passageway 622, the second locking portion 357 passes through the second working passageway 629, and the second working portion 355 extends from the second working passageway 629, between the top surface 614 and the second compression section 361.

Figure 32:
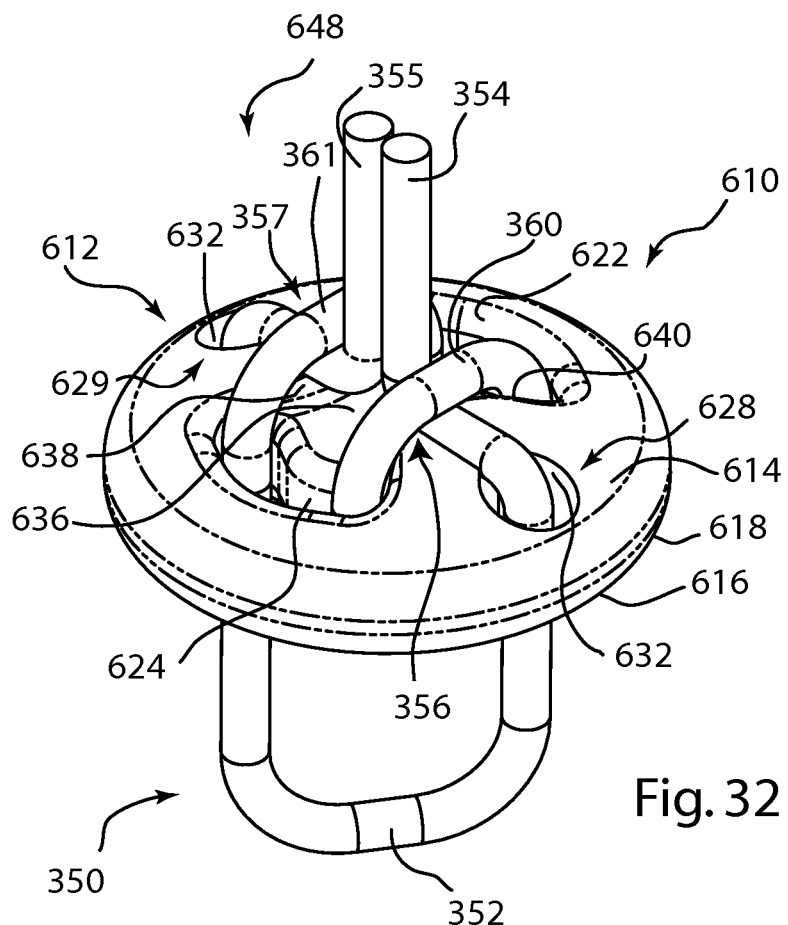
FIG. 32 is a perspective view of the line lock of FIG. 30, with suture passing tightly through the passageways of the line lock.

Referring to FIG. 32, a perspective view illustrates the assembly 648 of FIG. 31, with the suture 350 passing relatively tightly through the passageways 622, 624, 628, 629. When the standing portion 352 is tensioned, the compression sections 360, 361 press the working portions 354, 355 against the top surface 614 and/or into the central depression 636. The working portions 354, 355 are also pressed against the sharpened edges 640 to form bends in the working portions 354, 355 and to provide friction to keep the working portions 354, 355 from moving toward the working passageways 628, 629, respectively. The sharpened edges 640 effectively serve a function similar to that of the sharpened rim 538 and the sharpened lips 1438 of previous embodiments.

Figure 33:
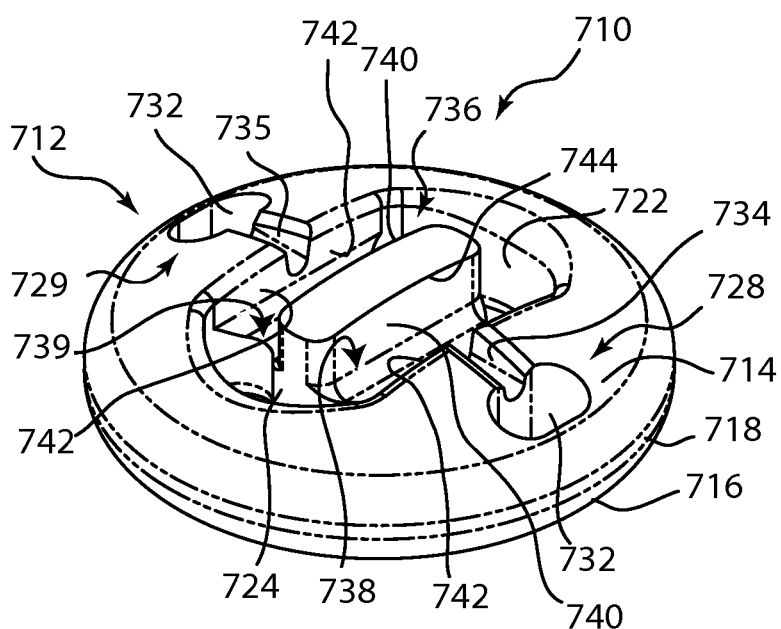
FIG. 33 is a perspective view of a line lock according to another alternative embodiment of the invention.

Referring to FIG. 33, a perspective view illustrates a line lock 710 according to another alternative embodiment of the invention. As in previous embodiments, the line lock 710 has a body 712 with a disc-like shape. The body 712 has a top surface 714, a bottom surface 716, and a periphery 718 that extends between the top surface 714 and the bottom surface 716 to define the generally circular profile of the body 712. The body 712 bounds a first primary passageway 722 and a first secondary passageway 724. The first primary and secondary passageways 722, 724 are generally arc-shaped, and each of the first primary and secondary passageways 722, 724 is broad enough to accommodate multiple passes of the suture 350.

The body 712 further bounds a first working passageway 728 and a second working passageway 729. Each of the working passageways 728, 729 includes an access region 732 that is sized to permit passage of the suture 350 therethrough with clearance. Furthermore, the body 712 has a first trough 734 adjoining the first working passageway 728 and a second trough 735 adjoining the second working passageway 729. The troughs 734, 735 are sized to press against the suture 350 to keep the suture 350 from sliding freely through the troughs 734, 735.

The body 712 also has a central plateau 736, a first groove 738, and a second groove 739. The grooves 738, 739 are positioned on either side of the central plateau 736 such that the first groove 738 lies between the central plateau 736 and the first working passageway 728 and the second groove 739 lies between the central plateau 736 and the second working passageway 729. The grooves 738, 739 are relatively straight and connect opposing ends of the first primary and secondary passageways 722, 724 together.

The grooves 738, 739 define a pair of inner walls 740 and a pair of outer walls 742, all of which extend generally perpendicular to the top surface 714. The inner walls 740 also provide the sides of the central plateau 736 and define sharpened edges 744 where they intersect the top surface of the central plateau 736.

Figure 34:
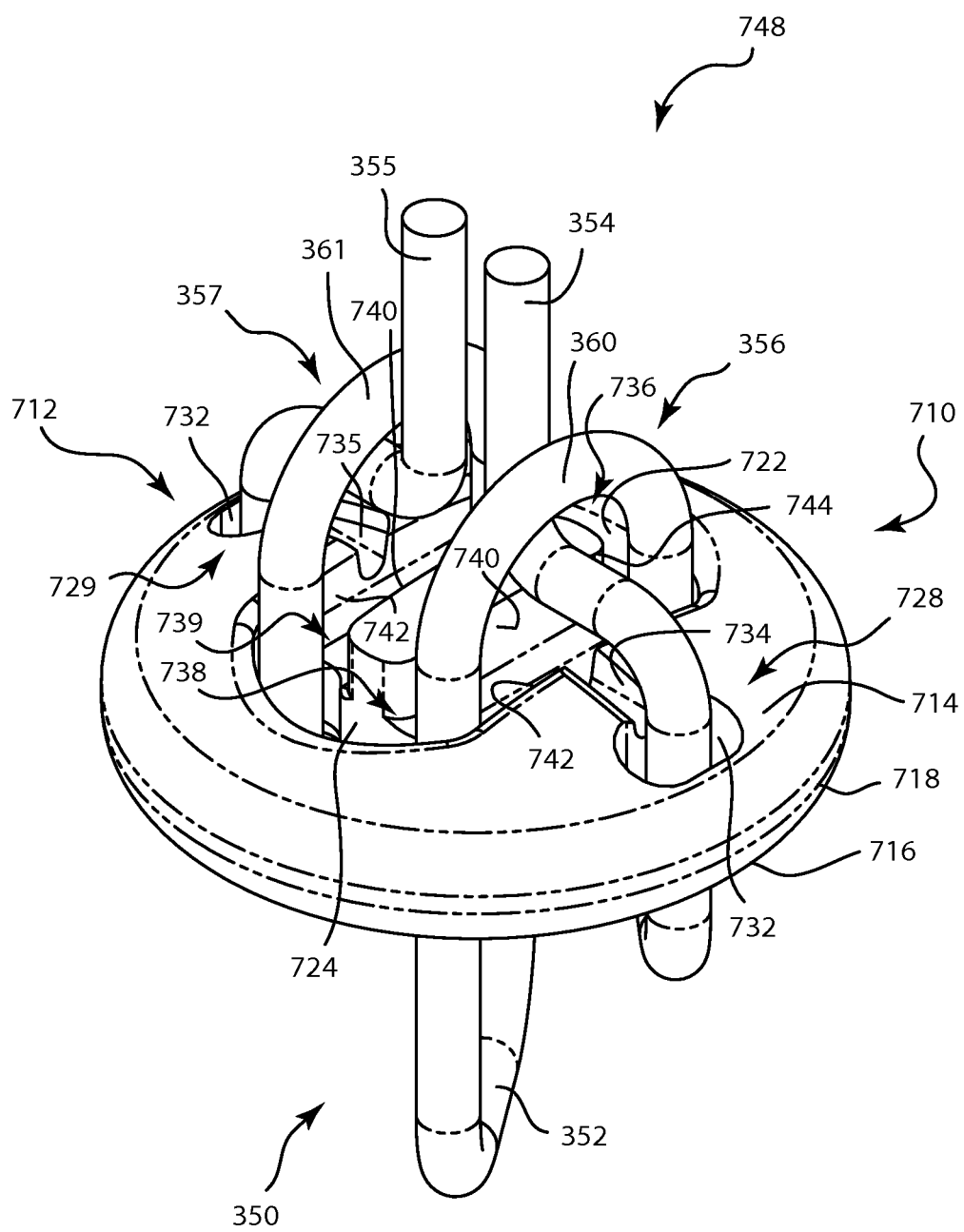
FIG. 34 is a perspective view of the line lock of FIG. 33, with a suture passing loosely through the passageways of the line lock.

Referring to FIG. 34, a perspective view illustrates a system 748 including the line lock 710 of FIG. 27 and the suture 350 passing relatively loosely through the passageways 722, 724, 728, 729 of the line lock 710. If desired, the suture 350 may be routed through the passageways 722, 724, 728, 729 in a manner very similar to that of the previous embodiment. Alternatively, as shown in FIG. 34, the first locking portion 356 may pass through the first secondary passageway 724, then through the first primary passageway 722, thereby defining the first compression section 360, and then through the first working passageway 728. Similarly, the second locking portion 357 may pass through the first primary passageway 722, then the first secondary passageway 724, thereby defining the second compression section 361, and then through the second working passageway 729.

From the first working passageway 728, the first working portion 354 passes between the first compression section 360 and the top surface 614 and/or the first trough 734 and the first groove 738. Similarly, from the second working passageway 729, the second working portion 355 passes between the second compression section 361 and the top surface 714 and/or the second trough 735

Figure 35:
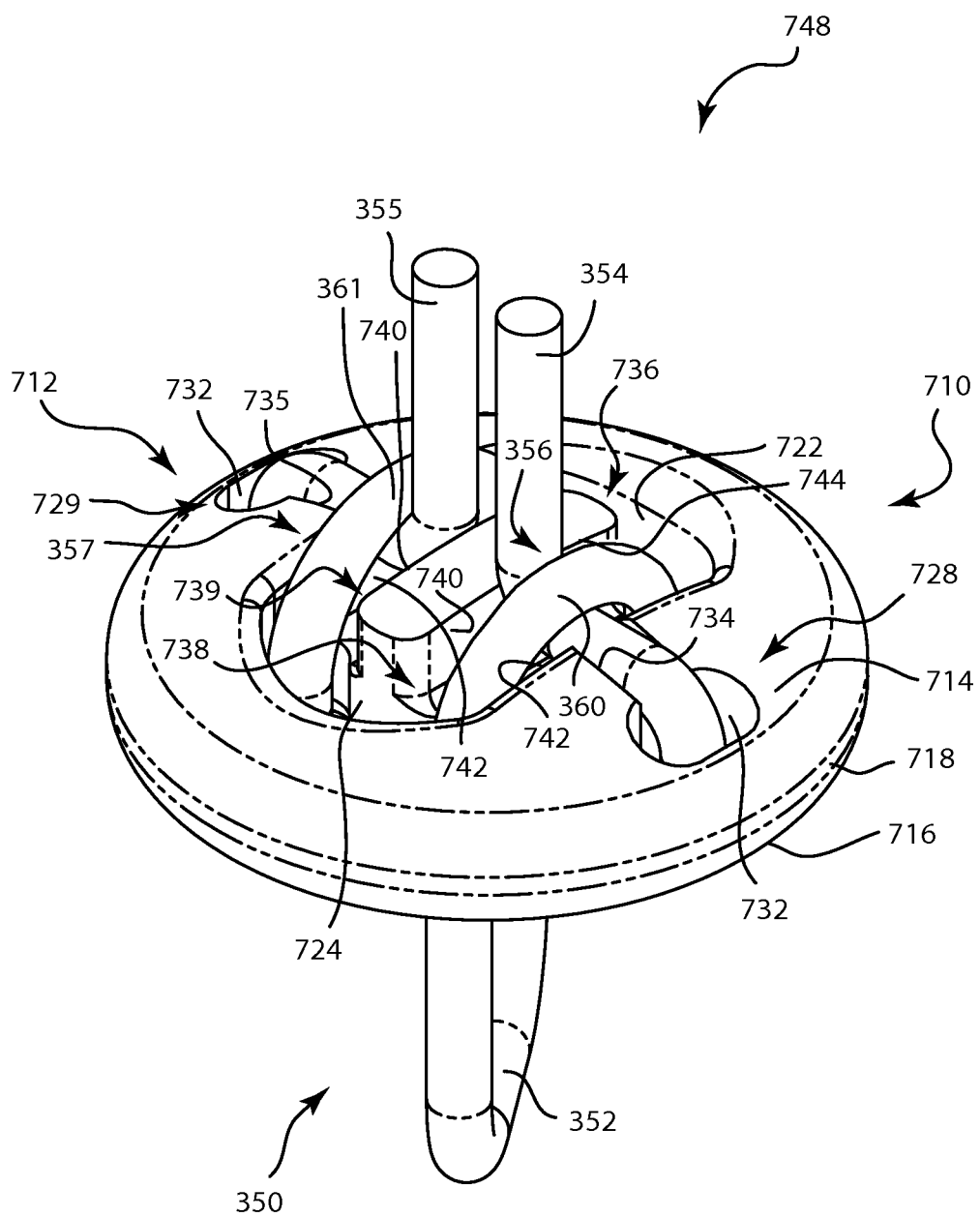
FIG. 35 is a perspective view of the line lock of FIG. 33, with suture passing tightly through the passageways of the line lock.

Referring to FIG. 35, a perspective view illustrates the system 748 of FIG. 34, with the suture 350 routed relatively tightly through the passageways 722, 724, 728, 729 of the line lock 710. When the standing portion 352 is tensioned, the compression sections 360, 361 press the working portions 354, 355 against the top surface 714, the troughs 734, 735, the grooves 738, 739, and the sharpened edge 744. The sharpened edge 744 helps to form a bend in each of the working portions 354, 355, and to provide friction that keeps the working portions 354, 355 from moving back toward the working passageways 728, 729. The working portions 354, 355 are also pressed into the troughs 734, 735, which add additional friction. Part of each of the working portions 354, 355 may be pressed into the grooves 738, 739 to enhance bending of the working portions 354, 355, thereby providing stronger locking.

Figure 36:
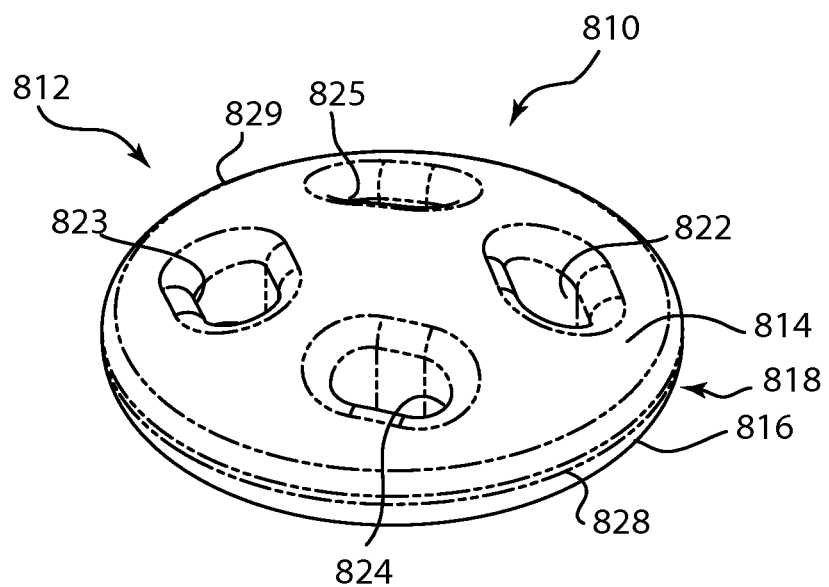
FIG. 36 is a perspective view of a line lock according to another alternative embodiment of the invention.

Referring to FIG. 36, a perspective view illustrates a line lock 810 according to another alternative embodiment of the invention. As in previous embodiments, the line lock 810 has a body 812 with a generally disc-like shape. The body 812 has a top surface 814, a bottom surface 816, and a periphery 818 extending between the top surface 814 and the bottom surface 816 to define the generally circular profile of the body 812. The body 812 bounds a first primary passageway 822, a second primary passageway 823, a first secondary passageway 824, and a second secondary passageway 825. All of the primary and secondary passageways 822, 823, 824, 825 are positioned proximate the periphery 818. However, the body 812 does not bound any working passageways.

The primary and secondary passageways 822, 823, 824, 825 are shaped in a manner similar to those of the embodiment of FIG. 19, and may thus be somewhat elongated to permit them to receive a doubled-over suture end or the like. Since no working passageways are present, the suture 350 may pass outside the periphery 818, and may rest against the periphery 818 in place of the bore of a working passageway.

For example, the standing portion of the suture 350 (not shown in FIG. 36) may extend from the bottom surface 816. The first locking portion 356 may pass through the first primary passageway 822, then through the first secondary passageway 824 to define the first compression section 360, and then around a first working portion 828 of the periphery 818. Similarly, the second locking portion 357 may pass through the second primary passageway 823, then through the second secondary passageway 825 to define the second compression section 361, and then around a second working portion 829 of the periphery. Although the suture 350 is not illustrated in FIG. 36, the pattern applied to the suture 350 by engagement with the line lock 810 may be similar to that of FIGS. 38 and 39, which will be described subsequently. Alternatively, the pattern applied to the suture 350 by engagement of the line lock 810 may be similar to that of FIGS. 41 and 42, which will also be described subsequently.

When the line lock 810 is locked, the compression sections 360, 361 may press the working portions 354, 355 of the suture against the top surface 814. The working portions 354, 355 must bend around the working portions 828, 829 of the periphery 818, which serve to provide friction in addition to bending. If desired, the working portions 828, 829 may be sharpened, notched, or otherwise shaped to enhance the magnitude of friction they provide. As in other embodiments, the working portions 354, 355 also frictionally engage the compression sections 360, 361. The line lock 810 of FIG. 36 is relatively compact, and may be especially useful for tissue retention in highly constrained spaces.

Figure 37:
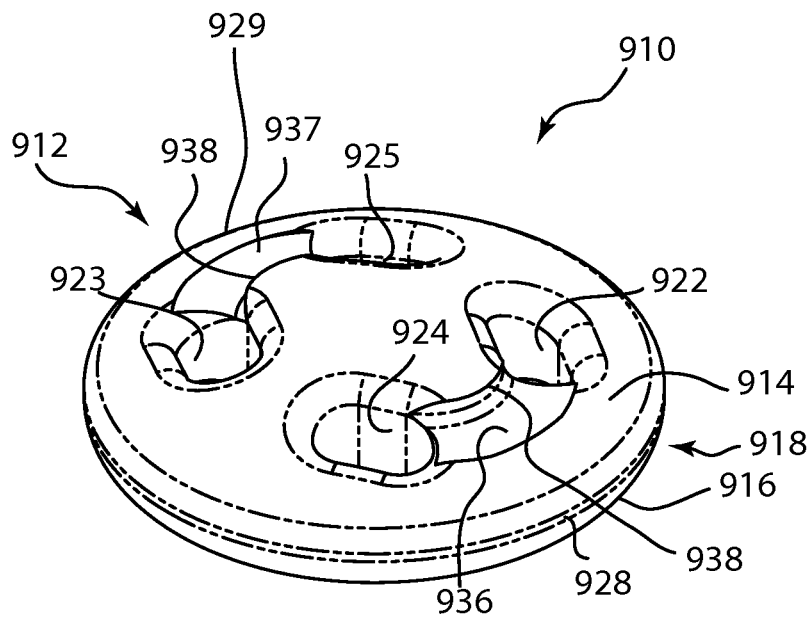
FIG. 37 is a perspective view of a line lock according to another alternative embodiment of the invention.

Referring to FIG. 37, a perspective view illustrates a line lock 910 according to another alternative embodiment of the invention. The line lock 910 has a body 912 with a disc-like shape. The body 912 may have a top surface 914, a bottom surface 916, and a periphery 918 that extends between the top surface 914 and the bottom surface 916 to define the generally circular profile of the body 912. As in the previous embodiment, the body 912 bounds a first primary passageway 922, a second primary passageway 923, a first secondary passageway 924, and a second secondary passageway 925.

Working passageways have again been omitted, and the periphery 918 includes first and second working portions 928, 929 along which the suture 350 may be routed in place of working passageways. Additionally, the body 912 has a first groove 936 extending between the first primary and secondary passageways 922, 924, and a second groove 937 extending between the second primary and secondary passageways 923, 925. The grooves 936, 937 define sharpened lips 938 where they intersect the top surface 914. The sharpened lips 938 face outward, and each of the sharpened lips 938 has a generally arcuate shape similar to the generally arcuate shape of each of the grooves 936, 937.

Figure 38:
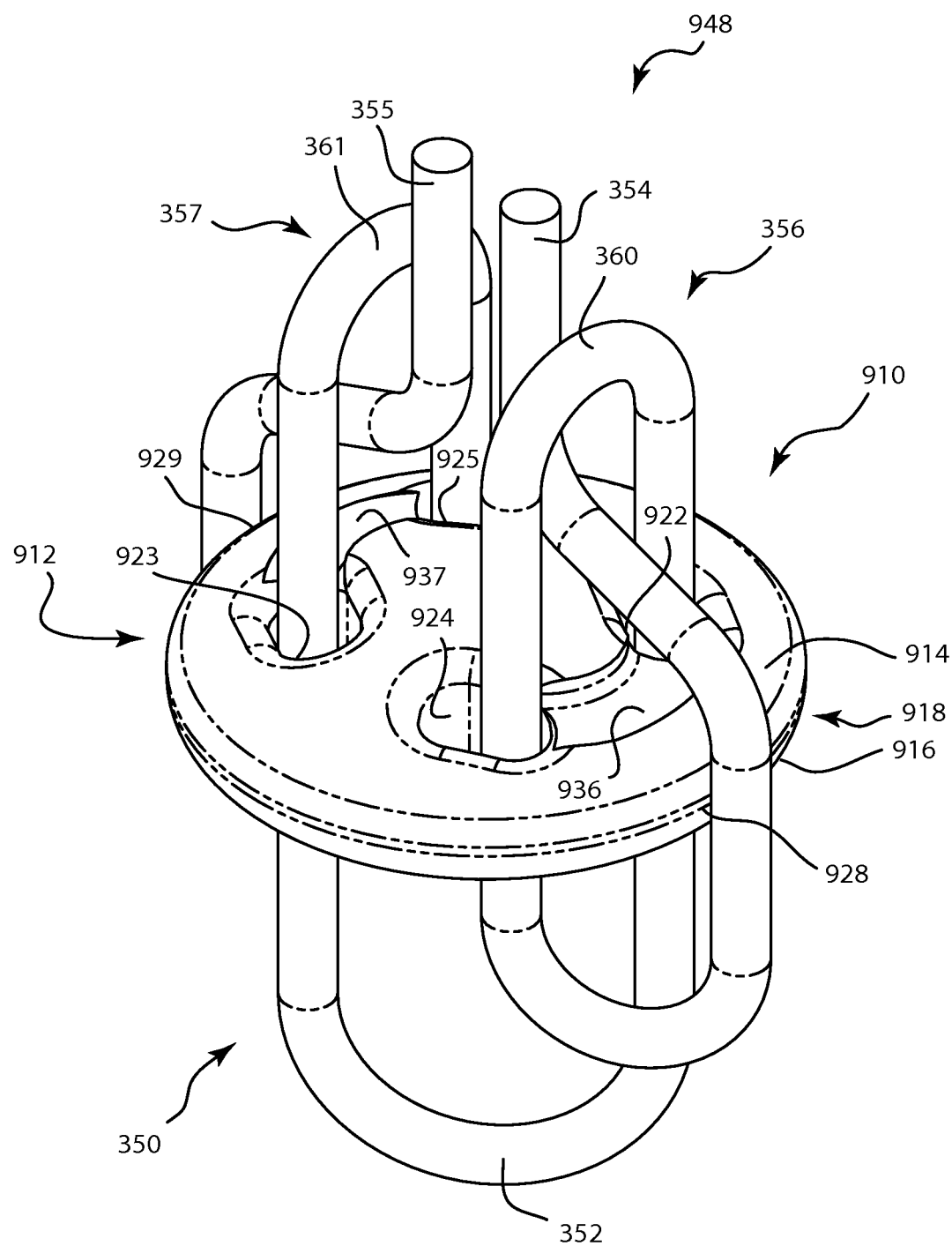
FIG. 38 is a perspective view of the line lock of FIG. 37, with a suture passing loosely through the passageways of the line lock.

Referring to FIG. 38, a perspective view illustrates a system 948 including the line lock 910 and the suture 350, with the suture 350 passing relatively loosely through the passageways 922, 923, 924, 925 of the line lock 910. As shown, the first locking portion 356 passes through the first primary passageway 922, then the first secondary passageway 924, thereby defining the first compression section 360 of the suture 350. Similarly, the second locking portion 357 passes through the second primary passageway 923, then through the second secondary passageway 925 to define the second compression section 361 of the suture 350.

The first locking portion 356 then passes around the first working portion 928 of the periphery 918, and then between the top surface 914 and the first compression section 360. By the same token, the second locking portion 357 then passes around the second working portion 929 of the periphery 918, and then between the top surface 914 and the second compression section 361.

Figure 39:
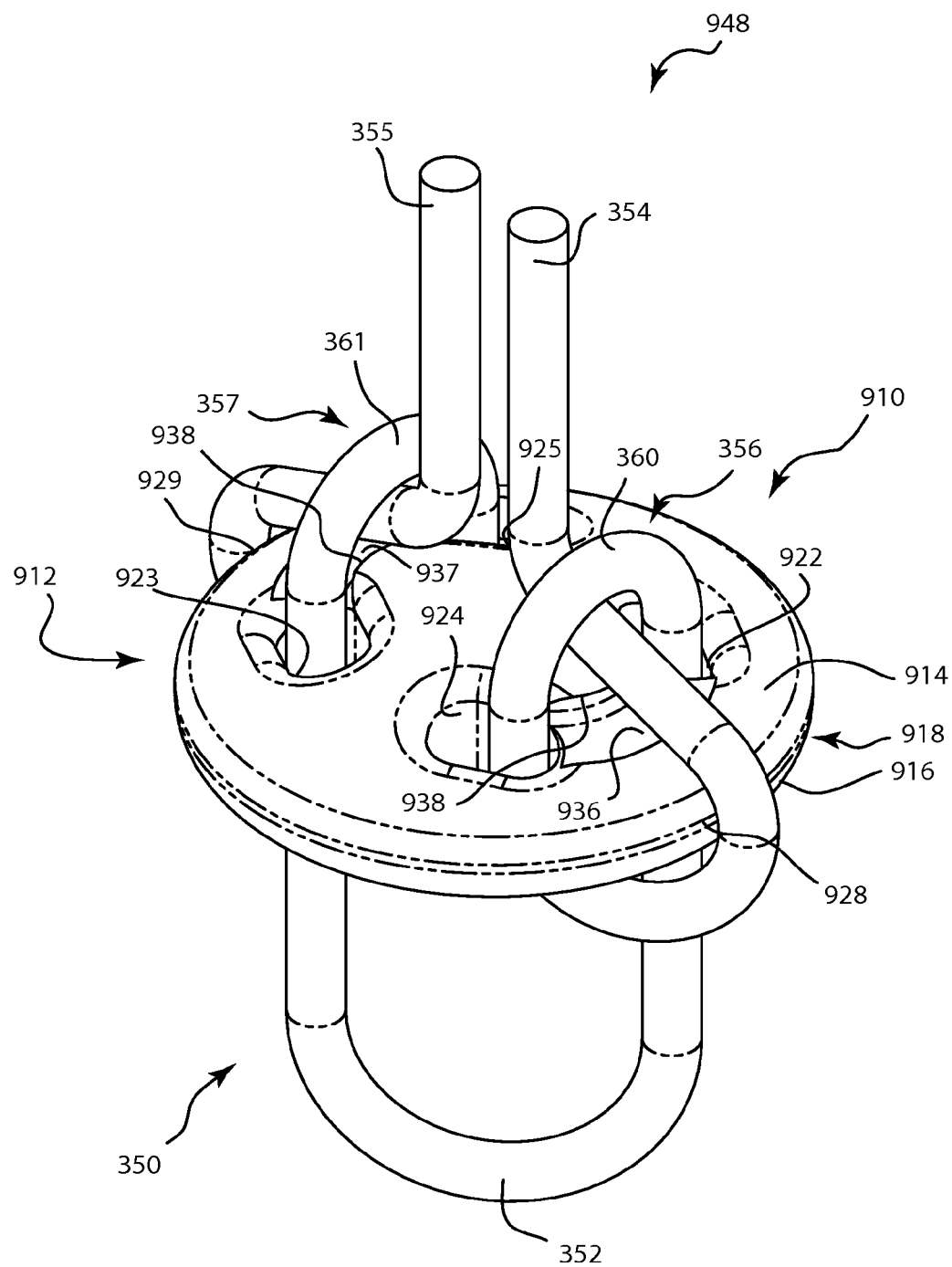
FIG. 39 is a perspective view of the line lock of FIG. 37 with suture passing tightly through the passageways of the line lock.

Referring to FIG. 39, a perspective view illustrates the system 948 of FIG. 38, with the suture 350 passing relatively tightly through the passageways 922, 923, 924, 925 of the line lock 910. When the standing portion 352 tightens, the compression sections 360, 361 press the working portions 354, 355 of the suture 350 against the grooves 936, 937 and the top surface 914, including the sharpened lips 938. The sharpened lips 938 provide bends in the working portions 354, 355, and also exert frictional force on the working portions 354, 355 to keep them from moving toward the working portions 928, 929 of the periphery 918. The compression sections 360, 361 may slide into the grooves 936, 937 to enhance bending of the working portions 354, 355.

Figure 40:
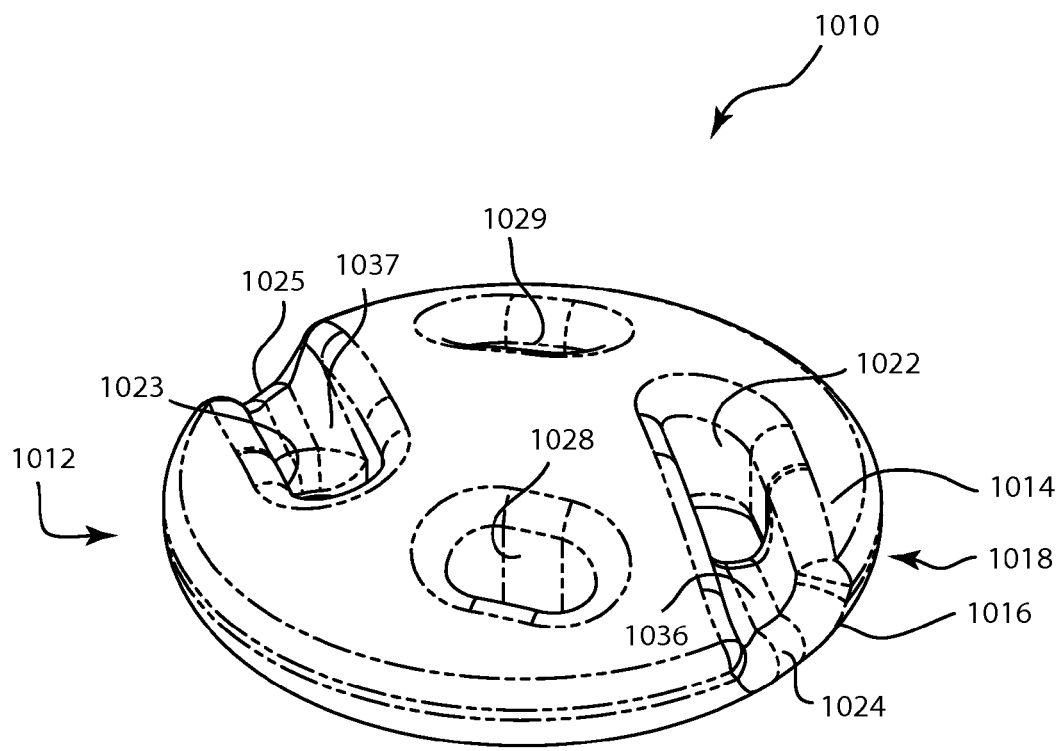
FIG. 40 is a perspective view of a line lock according to another alternative embodiment of the invention.

Referring to FIG. 40, a perspective view illustrates a line lock 1010 according to another alternative embodiment of the invention. The line lock 1010 has a body 1012 with a disc-like shape. The body 1012 has a top surface 1014, a bottom surface 1016, and a periphery 1018 extending between the top surface 1014 and the bottom surface 1016 to provide the generally circular profile of the body 1012. The body 1012 bounds a first primary passageway 1022 and a second primary passageway 1023.

Furthermore, the body 1012 partially bounds a first secondary passageway 1024 and a second secondary passageway 1025. In the embodiment of FIG. 40, the secondary passageways 1024, 1025 take the form of notches formed in the periphery 1018. As mentioned previously, the term "passageway," as used in this application, is broadly interpreted to include partially bound apertures, open channels, recesses, grooves, slots, and the like, that are capable of receiving a line and at least partially retaining the line therein. Accordingly, the structures labeled by reference numbers 1024, 1025 of FIG. 40 are, indeed, passageways. The secondary passageways 1024, 1025 are contiguous with the periphery 1018 because the bore of each of the secondary passageways 1024, 1025 transitions directly into the periphery 1018, with no significant intervening surface.

The body 1012 also bounds a first working passageway 1028 and a second working passageway 1029. The primary passageways 1022, 1023 and the working passageways 1028, 1029 may be shaped similarly to the primary and secondary passageways 322, 323, 324, 325 of the embodiment of FIG. 19, in that they are slightly elongated to permit passage of a doubled-over suture end. The body 1012 also has a first groove 1036 extending between the first primary passageway 1022 and the first secondary passageway 1024, and a second groove 1037 extending between the second primary passageway 1023 and the second secondary passageway 1025.

Figure 41:
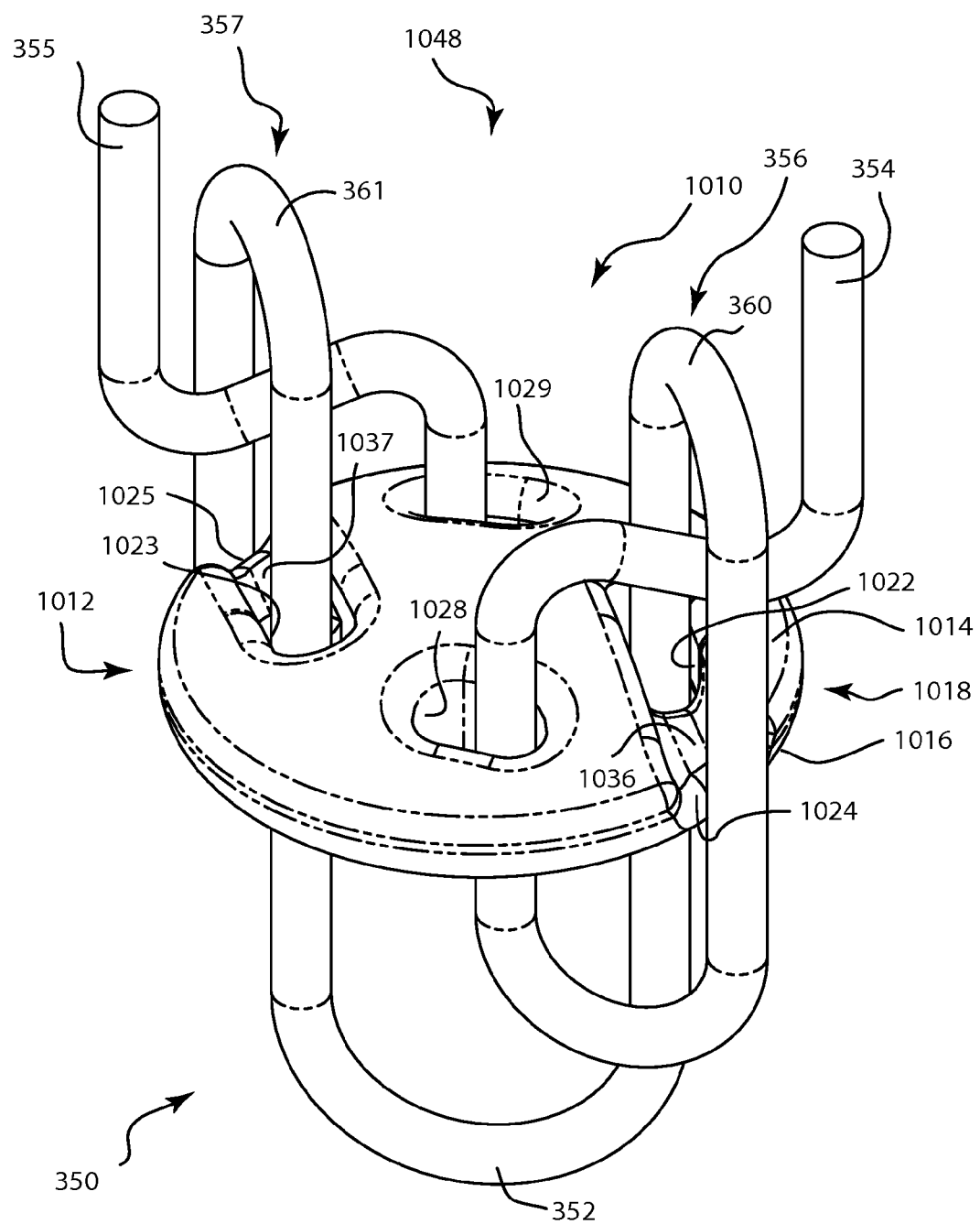
FIG. 41 is a perspective view of the line lock of FIG. 40, with a suture passing loosely through the passageways of the line lock.

Referring to FIG. 41, a perspective view illustrates a system 1048 including the line lock 1010 of FIG. 40 and the suture 350 passing relatively loosely through the passageways 1022, 1023, 1024, 1025, 1028, 1029 of the body 1012. As shown, the first locking portion 356 of the suture 350 extends through the first primary passageway 1022, then through the first secondary passageway 1024 to define the first compression section 360. Similarly, the second locking portion 357 extends through the second primary passageway 1023, then through the second secondary passageway 1025 to define the second compression section 361.

From the first secondary passageway 1024, the first locking portion 356 extends through the first working passageway 1028, and then between the first compression section 360 and the top surface 1014 and the first groove 1036. Similarly, from the second secondary passageway 1025, the second locking portion 357 extends through the second working passageway 1029, and then between oho the second compression section 361 and the top surface 1014 and the second groove 1037.

Figure 42:
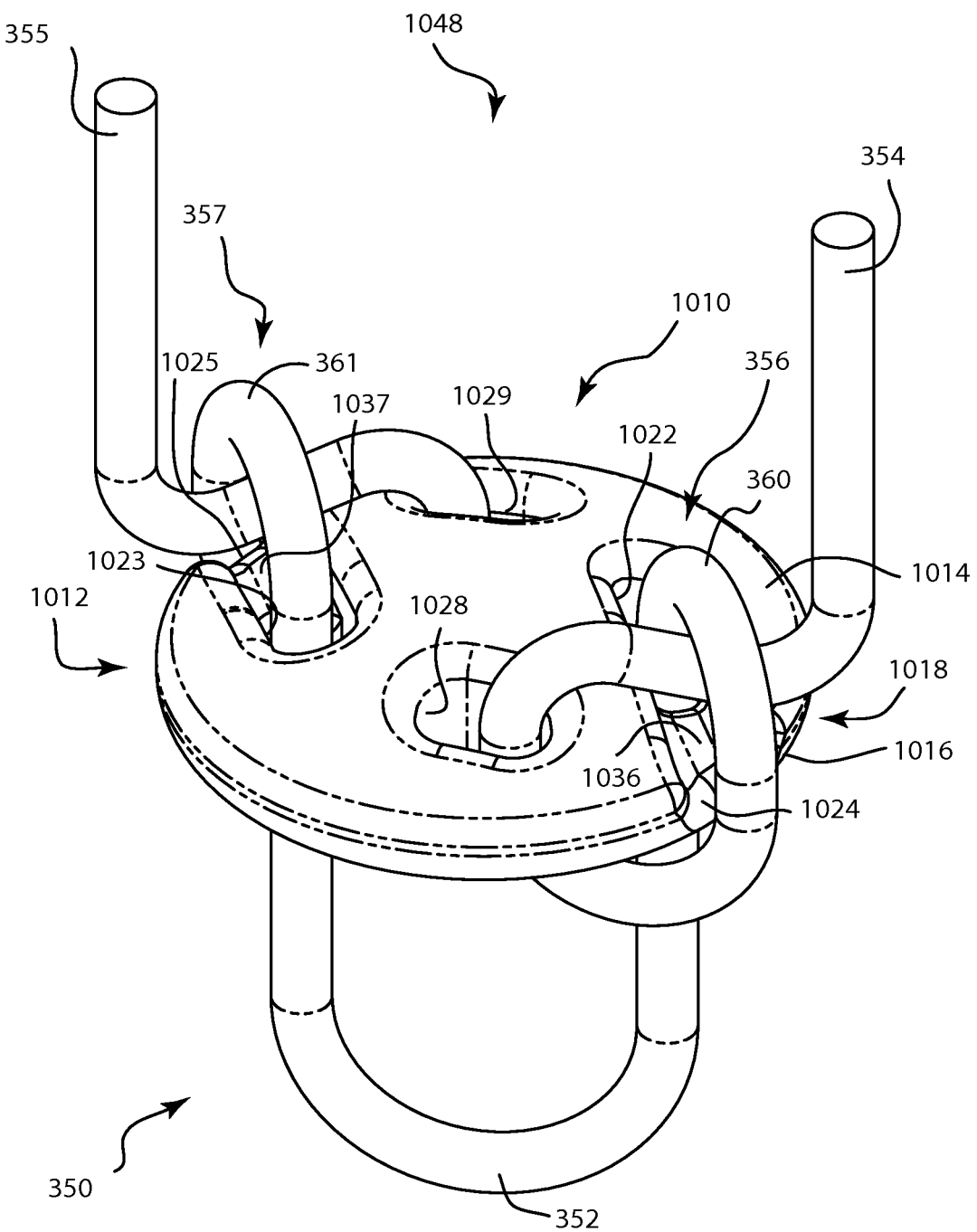
FIG. 42 is a perspective view of the line lock of FIG. 40 with suture passing tightly through the passageways of the line lock.

Referring to FIG. 42, a perspective view illustrates the system 1048 of FIG. 35, with the suture 350 passing relatively tightly through the passageways 1022, 1023, 1024, 1025, 1028, 1029 of the body 1012. When the standing portion 352 is tensioned, the compression sections 360, 361 press the working portions 354, 355 against the top surface 1014 and the grooves 1036, 1037. The working portions 354, 355 lie generally perpendicular to the grooves 1036, 1037 and are pressed into the grooves 1036, 1037 to form a pair of bends in each of the working portions 354, 355. The edges of the grooves 1036, 1037 also exert frictional force on the working portions 354, 355 to keep them from moving toward the working passageways 1028, 1029.

Figure 43:
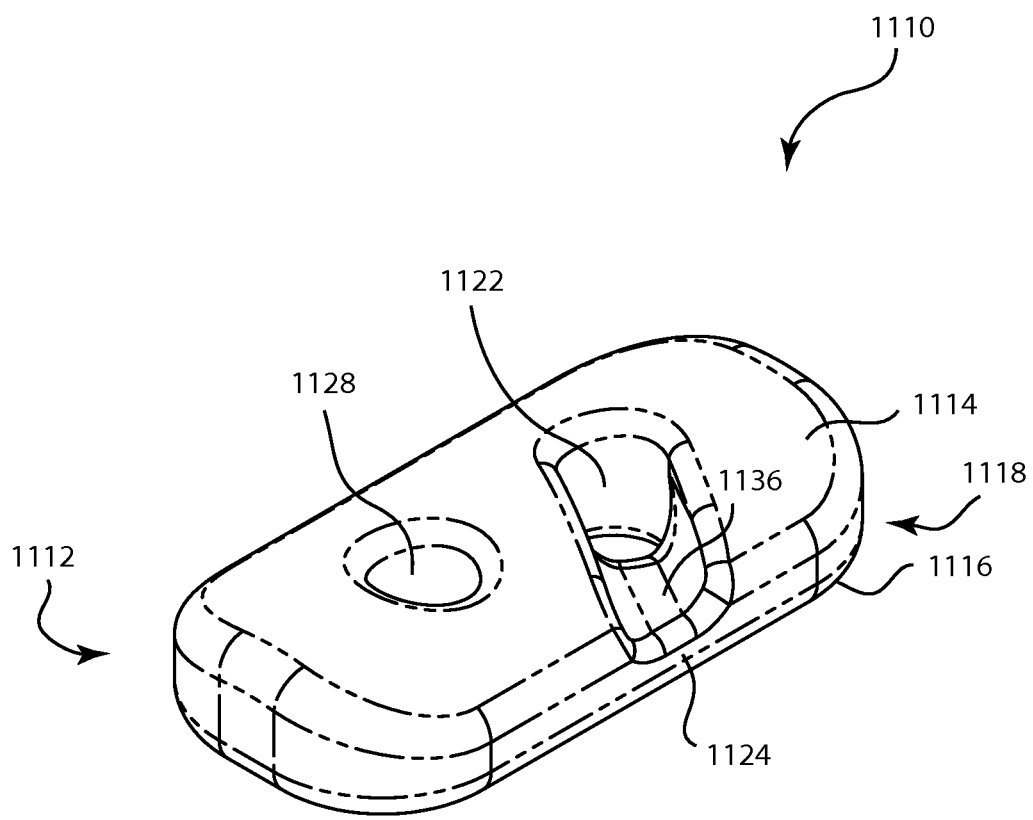
FIG. 43 is a perspective view of a line lock according to another alternative embodiment of the invention.

Referring to FIG. 43, a perspective view illustrates a line lock 1110 according to another embodiment of the invention. As shown, the line lock 1110 has a body 1112 with a generally rectangular prismatic shape, with rounded corners. The body 1112 has a top surface 1114, a bottom surface 1116, and a periphery 1118 extending between the top surface 1114 and the bottom surface 1116 to define the generally rectangular profile of the body 1112. The body 1112 at least partially bounds a plurality of passageways that enable the body 1112 to perform the function of half of the line lock 1010 of the previous embodiment, as will be set forth in greater detail below.

The passageways of the body 1112 include a first primary passageway 1122 fully bounded by the body 1112, a first secondary passageway 1124 partially bounded by the body 1112, and a first working passageway 1128 fully bounded by the body 1112. The first primary, secondary, and working passageways 1122, 1124, 1128 are similar to their counterparts 1022, 1024, 1028 from the previous embodiment, and operate to retain the suture 350 in a similar manner. Additionally, the body 1112 includes a first groove 1136 similar to the first groove 1036 of the previous embodiment.

Figure 44:
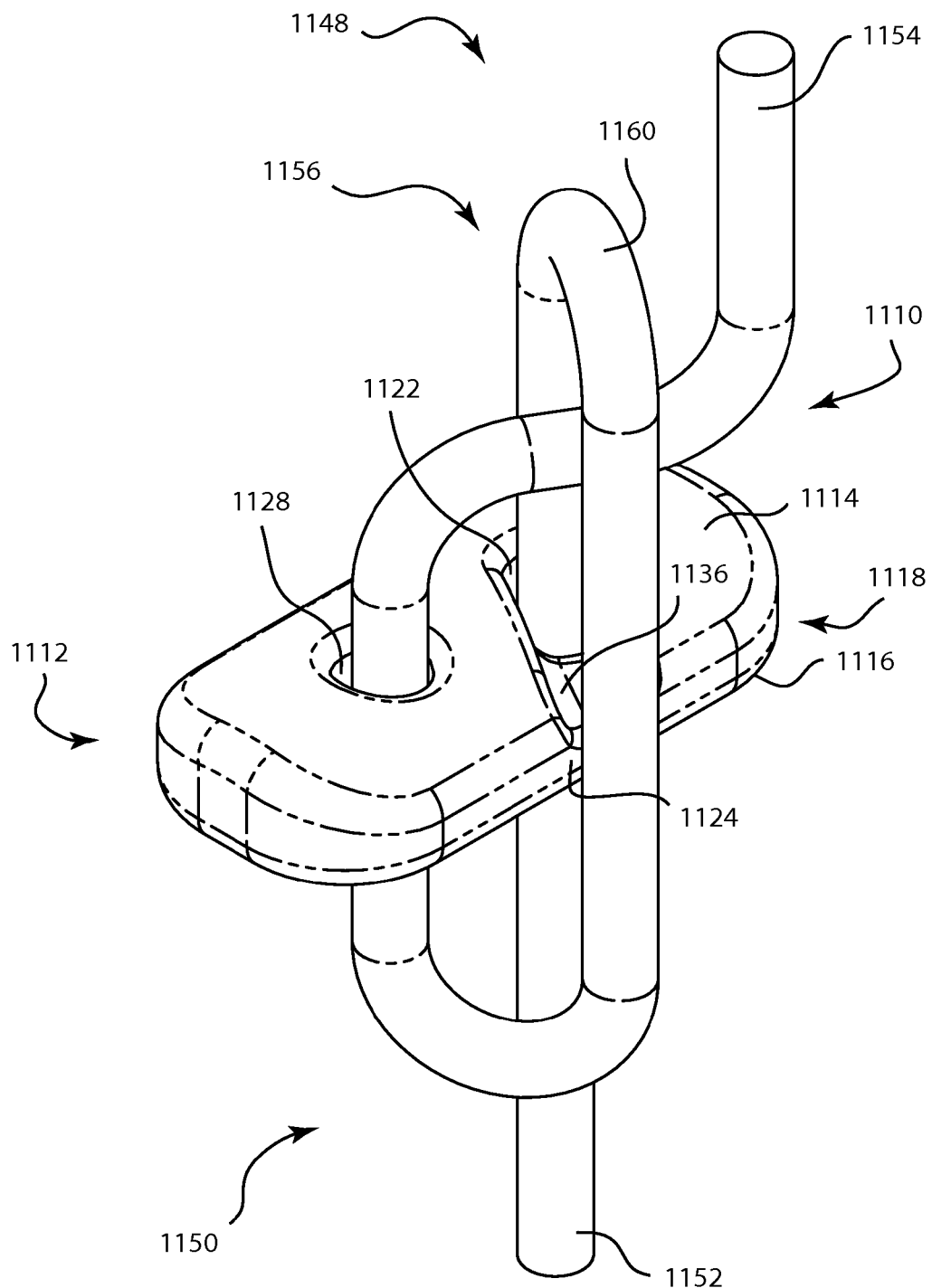
FIG. 44 is a perspective view of the line lock of FIG. 43, with a suture passing loosely through the passageways of the line lock.

Referring to FIG. 44, a perspective view illustrates a system 1148 including the line lock 1110 and the suture 350 passing relatively loosely through the passageways 1122, 1124, 1128 of the body 1112. The first locking portion 356 of the suture 350 passes through the first primary passageway 1122, then through the first secondary passageway 1124 to define the first compression section 360 of the suture 350. The first locking portion 356 then passes through the first working passageway 1128. From the first working passageway 1128, the first working portion 354 passes between the first compression section 360 and the top surface 1114 and the first groove 1136.

Figure 45:
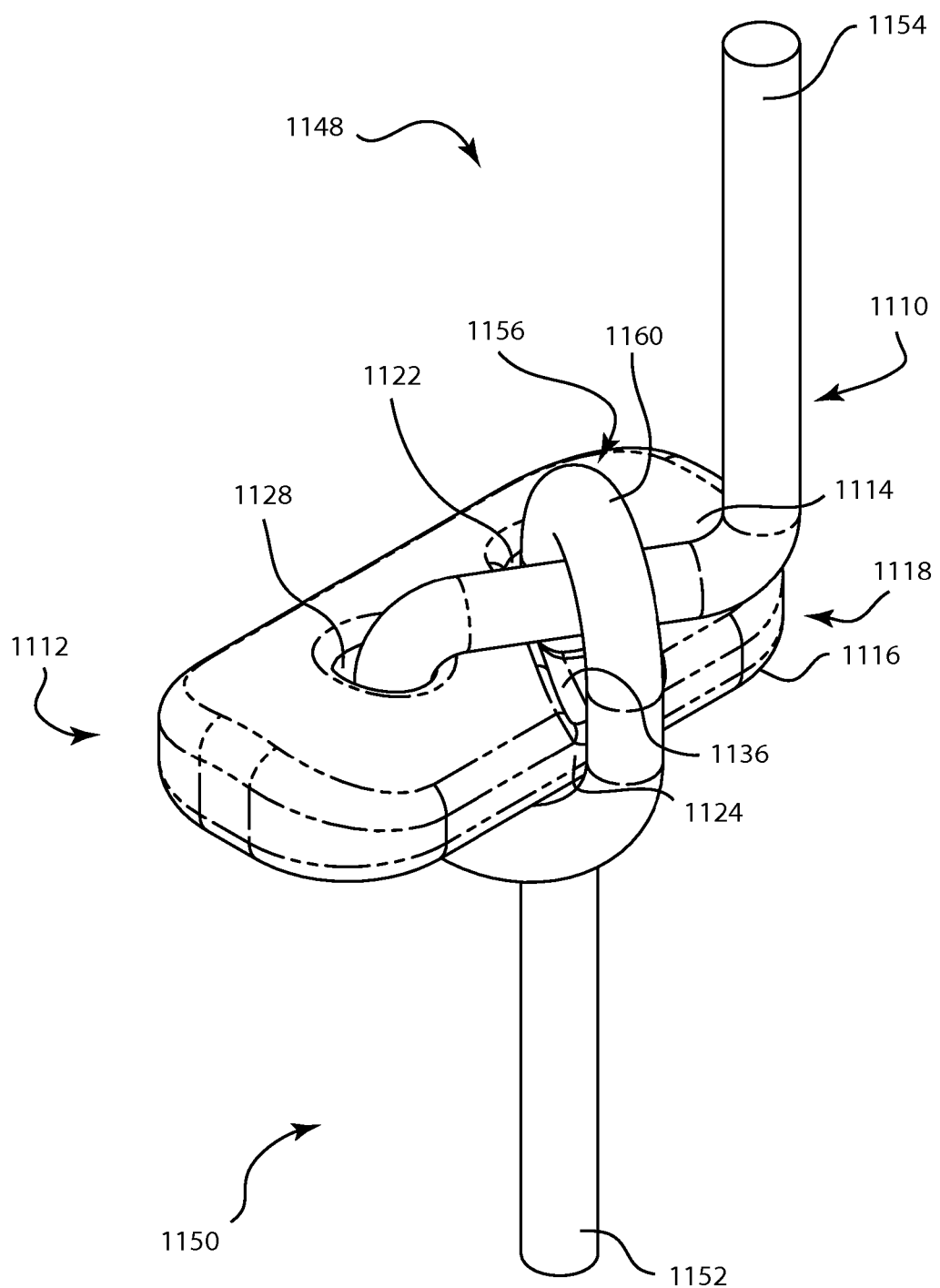
FIG. 45 is a perspective view of the line lock of FIG. 43 with suture passing tightly through the passageways of the line lock.

Referring to FIG. 45, a perspective view illustrates the system 1148 of FIG. 44, with the suture 350 passing relatively tightly through the passageways 1122, 1124, 1128. When the standing portion 352 is tensioned, the first compression section 360 presses the first working portion 354 against the top surface 1114 and the first groove 1136. As in the previous embodiment, the first groove 1136 helps to form bends in the first working portion 354 and to exert frictional force to keep the first working portion 354 from moving back toward the first working passageway 1128. Thus, as in previous embodiments, the first locking portion 356 is only able to move through the passageways 1122, 1124, 1128 along one direction.

In FIGS. 44 and 45, the working portion 352 is shown as an end, not a loop. However, the suture 350 need not terminate at the working portion 352 as shown, but may continue to provide the second locking portion 357 including the second compression section 361, and then the second working portion 355 (not shown in FIG. 44), as illustrated in connection with previous embodiments. The working portion 352 may then form a loop, and a second line lock (not shown) similar to the line lock 1110 may be used to lockably retain the second locking portion 357. Thus, the two line locks may cooperate to retain tissue.

Alternatively, the working portion 352 may indeed terminate with no loop. The working portion 352 may instead be tied or otherwise attached to an anchor or the like, so that the line lock 1110 can be used to cinch tissue along the standing portion 352 by moving along only one length of the suture 350. Since the line lock 1110 is only made to retain one length of the suture 350, the line lock 1110 may be relatively compact by comparison with previous embodiments, and may thus be especially useful for tissue retention in constrained spaces.

Figure 46:
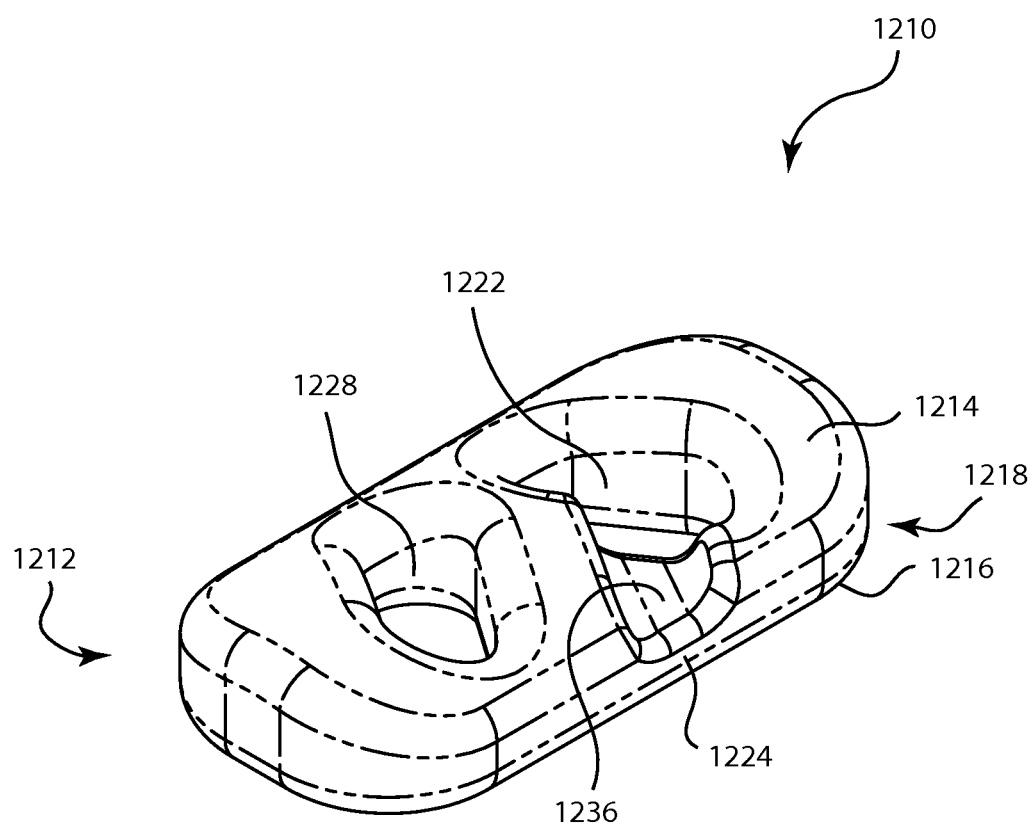
FIG. 46 is a perspective view of a line lock according to another alternative embodiment of the invention.

Referring to FIG. 46, a perspective view illustrates a line lock 1210 according to another alternative embodiment of the invention. As in the previous embodiment, the line lock 1210 has a body 1212 with a generally rectangular prismatic shape, with rounded corners. The body 1212 has a top surface 1214, a bottom surface 1216, and a periphery 1218 extending between the top surface 1214 and the bottom surface 1216 to define the generally rectangular profile of the body 1212. The body 1212 is configured similarly to the body 1112 of the previous embodiment, except that the body 1212 has passageways sized to simultaneously receive and lock multiple suture lengths.

More precisely, the body 1212 bounds a first primary passageway 1222, partially bounds a first secondary passageway 1224, and bounds a first working passageway 1228. The first primary and working passageways 1222, 1228 are elongated so as to be capable of simultaneously receiving multiple suture lengths. The first secondary passageway 1224 is only partially bounded by the body 1212, and may therefore be able to receive multiple suture lengths without elongation. As in the previous embodiment, the body 1212 also includes a first groove 1236 that extends between the first primary and secondary passageways 1222, 1224.

Figure 47:
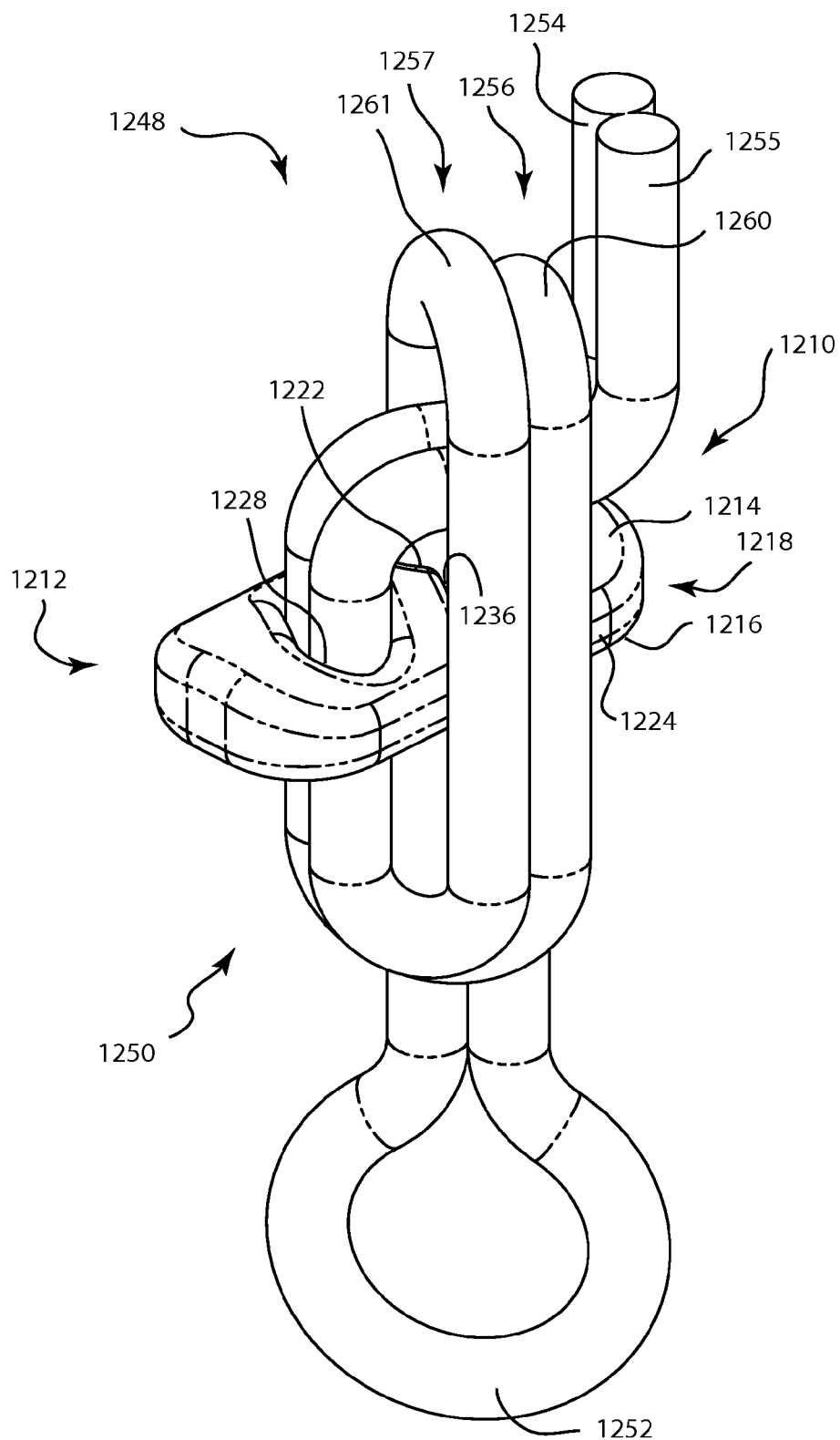
FIG. 47 is a perspective view of the line lock of FIG. 46, with a suture passing loosely through the passageways of the line lock.

Referring to FIG. 47, a perspective view illustrates a system 1248 including the line lock 1210 and the suture 350, with the suture 350 passing relatively loosely through the passageways 1222, 1224, 1228 of the body 1212. FIG. 47 illustrates the standing portion 352, both working portions 354, 355, and both locking portions 356, 357 of the suture 350, including both compression sections 360, 361. The standing portion 352 is again illustrated as a loop.

As shown, the locking portions 356, 357 are routed through the passageways 1222, 1224, 1228 side-by-side. More precisely, the locking portions 356, 357 pass through the first primary passageway 1222, then through the first secondary passageway 1224 to define the first and second compression sections 360, 361. The locking portions 356, 357 then pass through the first working passageway 1228. From the first working passageway 1228, the working portions 354, 355 pass between the compression sections 360, 361 and the top surface 1214 and the first groove 1236.

Figure 48:
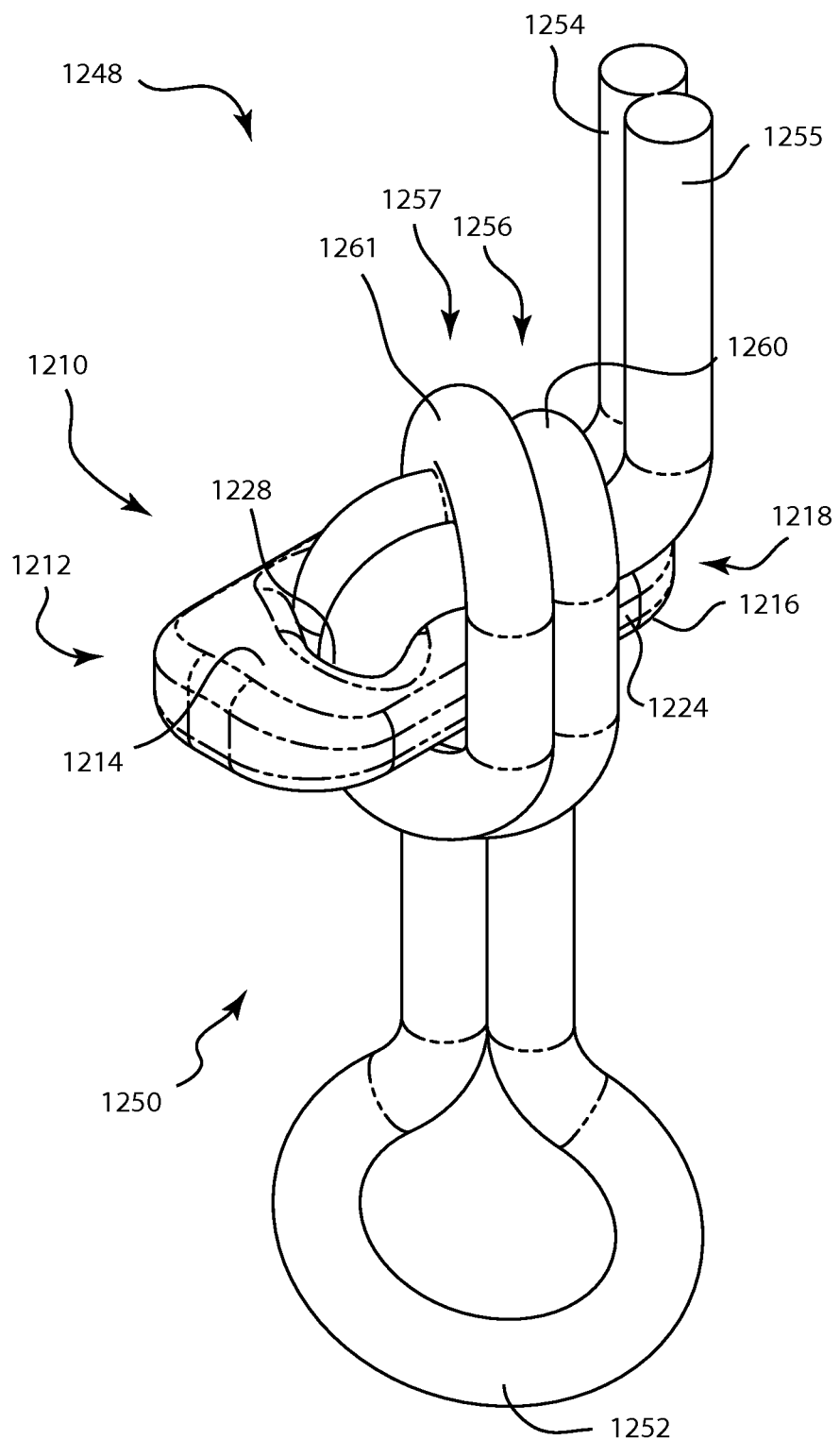
FIG. 48 is a perspective view of the line lock of FIG. 46 with suture passing tightly through the passageways of the line lock.

Referring to FIG. 48, a perspective view illustrates the system 1248 of FIG. 47, with the suture 350 relatively tightly passing through the passageways 1222, 1224, 1228 of the body 1212. The compression sections 360, 361 press the working portions 354, 355 against the top surface 1214 and the first groove 1236. The first groove 1236 helps to form bends in the working portions 354, 355 and to exert frictional force to keep the first working portions 354, 355 from moving back toward the first working passageway 1228. Thus, as in previous embodiments, the locking portions 356, 357 are only able to move through the passageways 1222, 1224, 1228 along one direction. As in previous embodiments, the standing portion 352 may pass through an anchor or the like to enable usage of the line lock 1210 for tissue retention.

The present invention has particular relevance to surgery, and more particularly to tissue retention through the use of sutures. However, the principles, structures, and methods of the present invention may also be extended to other fields, including the use of larger line locks for locking ropes or cables in a wide variety of applications.

As previously described in U.S. application Ser. No. 10/942,275, referring to FIG. 49, a perspective view illustrates one embodiment of a system 2400 including the line lock 310 of FIG. 19 (not visible in FIG. 49), and various implements to help insert, or "thread," the suture 350 through the passageways 322, 323, 324, 325, 328, 329 of the line lock 310. A longitudinal direction 2402, a lateral direction 2404, and a transverse direction 2406 cooperate to form a system of orthogonal axes that will be used for reference in the following description.

In addition to the line lock 310, the system 2400 includes a cartridge 2410, a first threader 2412, and a second threader 2414. The cartridge 2410 contains the line lock 310 and, when in the closed configuration shown in FIG. 49, substantially encloses the line lock 310 to facilitate insertion of the suture 350 through the passageways 322, 323, 324, 325, 328, 329, and possibly, to help isolate the line lock 310 from contaminants. In this application, the phrase "substantially enclose" does not require full enclosure; rather, some portion(s) of the substantially enclosed part may protrude from the enclosure.

The cartridge 2410 may be formed of a plastic such as polypropylene, PEEK, or the like. The threaders 2412, 2414 pass through the cartridge 2410 along first and second pathways, respectively, to enable a user to draw the suture 350 through the passageways 322, 323, 324, 325, 328, 329 along the correct pattern, as will be described in greater detail subsequently. The threaders 2412, 2414 may be formed substantially of a fibrous material or a plastic, such as nylon.

Figure 49:
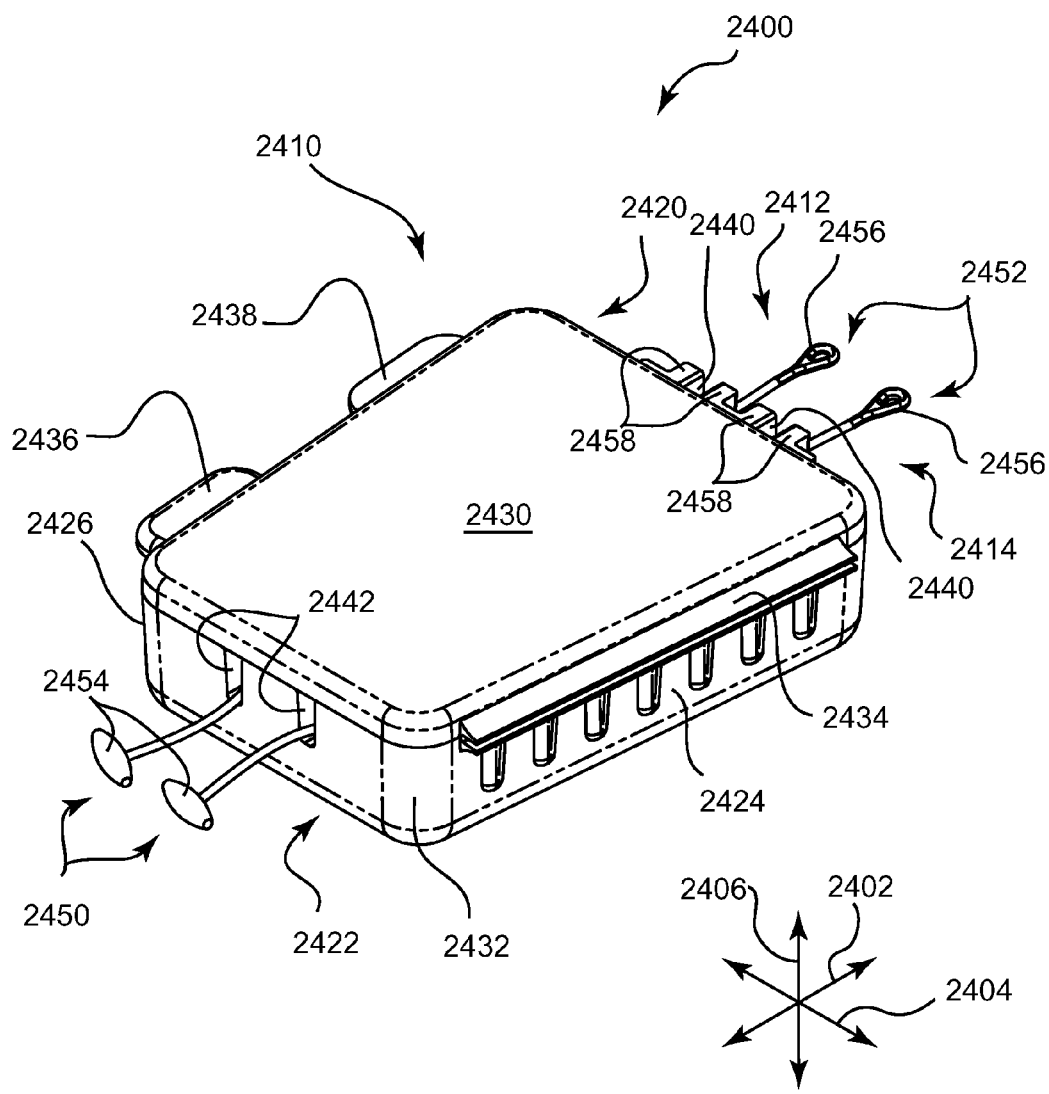
FIG. 49 is a perspective view of a system including a cartridge with threaders that facilitate the insertion of suture through the passageways of the line lock of FIG. 19.

As shown in FIG. 49, the cartridge 2410 has a first longitudinal end 2420, a second longitudinal end 2422, a first lateral end 2424, and a second lateral end 2426. The threaders 2412, 2414 pass through the longitudinal ends 2420, 2422. Furthermore, the cartridge 2410 has a lid 2430 designed to move with respect to the remainder of the cartridge 2410, which will be referred to as a containment portion 2432. More specifically, a living hinge 2434 extends generally along the first lateral end 2424, between the adjacent edges of the lid 2430 and the containment portion 2432. The living hinge 2434 is integrally formed with the lid 2430 and the containment portion 2432 and flexes to enable pivotal motion of the lid 2430 with respect to the containment portion 2432. In alternative embodiments, a conventional hinge may be used, or a lid may be slidable with respect to and/or fully removable from the remainder of the cartridge, thereby obviating the need for a hinging mechanism.

A first tab 2436 integrally formed with the lid 2430 and a second tab 2438 integrally formed with the containment portion 2432 may easily be pushed in opposite directions, for example, by a user's thumbs, to open the cartridge 2410. The lid 2430 and the containment portion 2432 may be designed to adhere to each other at the second lateral end 2426 so that the cartridge 2410 only opens when a threshold force is applied. Thus, the cartridge 2410 may not open if dropped or jostled.

The first longitudinal end 2420 has a first set of slots 2440 through which the threaders 2412, 2414 pass. Similarly, the second longitudinal end 2422 has a second set of slots 2442 through which the threaders 2412, 2414 pass. Thus, the threaders 2412, 2414 extend into the cartridge 2410 through the first longitudinal end 2420 and out again through the second longitudinal end 2422. Each of the threaders 2412, 2414 has a leading end 2450 adjacent to the second set of slots 2442 and a trailing end 2452 adjacent to the first set of slots 2440.

Each of the leading ends 2450 has a pull feature designed to facilitate grasping and drawing of the leading ends 2450 by hand. In the embodiment of FIG. 49, the pull features take the form of grips 2454 that may be easily grasped, for example, between a thumb and an index finger. The grips 2454 may be plastic rods crimped, insert molded, adhesive bonded, or otherwise attached to the remainder of the threaders 2412, 2414. In alternative embodiments, differently configured pull features may be used, including rigid rings, flexible loops, spherical beads, squared beads, and the like.

Additionally, each of the trailing ends 2452 has a suture retention feature designed to retain a portion of a suture to enable the threaders 2412, 2414 to draw the suture through the passageways 322, 323, 324, 325, 328, 329 of the line lock 310. In FIG. 49, the suture retention features take the form of eyelets 2456, each of which is able to receive an end of the suture such that the suture end can double back on itself to be drawn through the cartridge 2410. The eyelets 2456 may be crimped, adhesive bonded, insert molded, or otherwise attached to the remainder of the threaders 2412, 2414. In alternative embodiments, differently configured suture retention features may be used, including adhesive-coated surfaces, collets, clips, flexible loops, and the like.

The eyelets 2456 may be retained to ensure that they are not drawn into the cartridge 2410 prior to attachment to the suture to be threaded through the line lock 310. For example, the containment portion 2432 may have retention posts 2458 that extend in the longitudinal direction 2402 on either side of each of the slots of the first set of slots 2440. Each of the eyelets 2456 may optionally be looped around a pair of the retention posts 2458 so that each eyelet 2456 is unable to enter the corresponding slot of the first set of slots 2440 until the eyelet 2456 is removed from around the retention posts 2458. Each of the eyelets 2456 may need to be slightly larger than shown in FIG. 49 to enable them to encircle a pair of the retention posts 2458. The retention posts 2458 may also serve a similar function if loops or other flexible suture retention features are used in place of the eyelets 2456.

Figure 50:
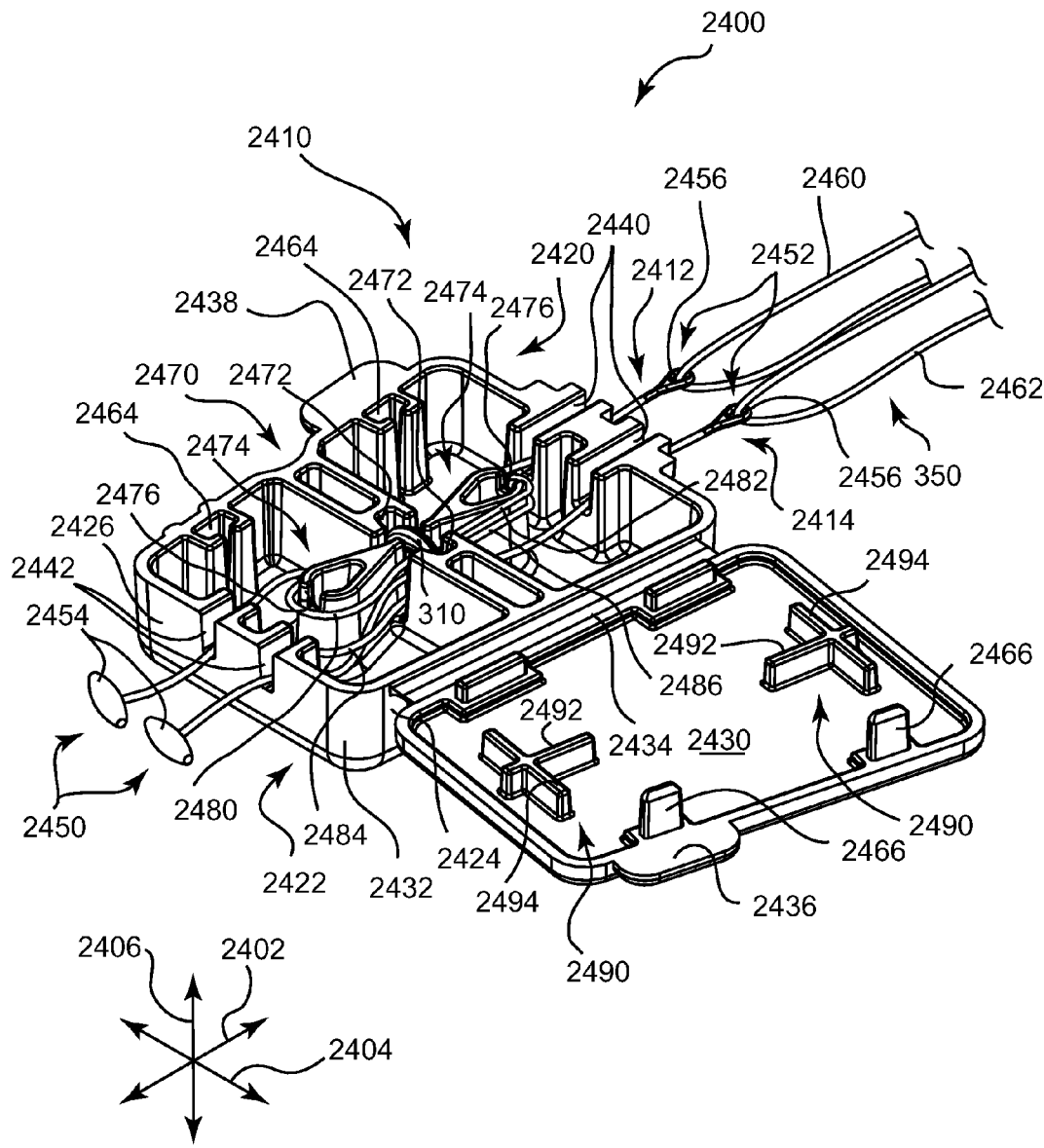
FIG. 50 is a perspective view of the system of FIG. 49, with the lid of the cartridge open and sutures coupled to the trailing ends of the threaders.

Referring to FIG. 50, a perspective view illustrates the system 2400 of FIG. 49, with the cartridge 2410 in the open configuration to expose the line lock 310. The suture 350 has also been inserted into engagement with the trailing ends 2452 of the threaders 2412, 2414. More precisely, a first suture portion 2460 of the suture 350 has been inserted through the eyelet 2456 of the first threader 2412, and a second suture portion 2462 of the suture 350 has been inserted through the eyelet 2456 of the second threader 2414. The first and second suture portions 2460, 2462 are doubled back on themselves to permit the eyelets 2456 to draw them through the cartridge 2410 and through the passageways 322, 323, 324, 325, 328, 329 (not visible in FIG. 50) of the line lock 310.

Each of the suture portions 2460, 2462 may correspond to one or more of the various portions 352, 354, 355, 356, 357 of the suture 350. However, no direct correlation is necessary because any portion(s) of the suture 350 may be drawn through the line lock 310 via the cartridge 2410 and the threaders 2412, 2414. In the alternative to threading two portions of a suture through the line lock 310, the system 2400 may be used to thread two separate sutures through the line lock 310.

As shown in FIG. 50, the containment portion 2432 has a pair of sockets 2464 formed therein. Each of the sockets 2464 may provide a generally rectangular cavity surrounded by a wall that is slotted to permit expansion of the socket 2464. The lid 2430 has a pair of posts 2466 that are generally rectangular in shape, and are sized and positioned to slide into the sockets 2464 when the cartridge 2410 is in the closed configuration. The posts 2466 may be sized to fit relatively tightly into the sockets 2464 so that the cartridge 2410 does not open until the threshold force is applied to remove the posts 2466 from the sockets 2464.

The containment portion 2432 also has a central divider 2470 that extends generally along the lateral direction 2404 to effectively separate the containment portion 2432 into two separate compartments. The containment portion 2432 defines a retention feature designed to retain the line lock 310. In this application, the terms "retention feature" and "threading feature" are to be broadly interpreted to include, not just single structural elements, but also groups of elements that cooperate to carry out line lock retention or suture threading.

In FIG. 50, the retention feature takes the form of a pair of troughs 2472 positioned on either side of a space in which the line lock 310 rests within the containment portion 2432. The troughs 2472 face each other such that they retain the periphery 318 of the body 312 of the line lock 310 to resist motion of the line lock 310 along the longitudinal and transverse directions 2402, 2406. The troughs 2472 are exposed on the open side of the containment portion 2432 so that the line lock 310 can be inserted into the space between the troughs 2472, or removed therefrom, by moving the line lock 310 along the transverse direction 2406.

Additionally, the containment portion 2432 has a threading feature designed to help guide the suture 350 through the passageways 322, 323, 324, 325, 328, 329 along the desired pattern. In FIG. 50, the threading feature takes the form of a pair of posts 2474 positioned on either side of the central divider 2470, and thus on either side of the space in which the line lock 310 rests. Each of the posts 2474 may have a generally teardrop-shaped cross section, as taken through a plane parallel to the longitudinal and transverse directions 2402, 2406. Each of the posts 2474 also has a slot 2476 facing the adjacent one of the first and second longitudinal ends 2420, 2422.

The threaders 2412, 2414 are wrapped around the posts 2474 along a configuration similar to that provided by the suture 350 illustrated in FIGS. 20 and 21. More precisely, from its trailing end 2452, the first threader 2412 passes through one of the first set of slots 2440, then through the first primary passageway 322 (not visible in FIG. 50) and then through the first secondary passageway 323 (not visible) to define a first loop 2480 of the first threader 2412. From the first secondary passageway 323, the first threader 2412 passes through the first working passageway 328 (not visible) to define a second loop 2482 of the first threader 2412. From the first working passageway 328, the first threader 2412 extends through the first loop 2480 and then passes through the corresponding one of the second set of slots 2442, to the leading end 2450.

Similarly, from its trailing end 2452, the second threader 2414 passes through one of the first set of slots 2440, then through the second primary passageway 2324 (not visible in FIG. 50) and then through the second secondary passageway 325 (not visible) to define a first loop 2484 of the second threader 2414. From the second secondary passageway 325, the second threader 2414 passes through the second working passageway 329 (not visible) to define a second loop 2486 of the second threader 2414. From the second working passageway 329, the second threader 2414 extends through the first loop 2484 and then passes through the corresponding one of the second set of slots 2442, to the leading end 2450.

The various portions of the threaders 2412, 2414 may be positioned to correspond to portions of the suture 350, as labeled in FIGS. 20 and 21. For example, the trailing ends 2452 may correspond to the standing portion 352 of the suture 350, the leading ends 2450 may correspond to the working portions 354, 355, and the loops 2480, 2482, 2484, 2486 may correspond to the locking portions 356, 357. The first loops 2480, 2484 of the threaders 2412, 2414, respectively, may more precisely correspond to the compression sections 360, 361 of the locking portions 356, 357. Accordingly, when the suture 350 is drawn through the passageways 322, 323, 324, 325, 328, 329 by the threaders 2412, the suture 350 assumes a configuration having the various portions 352, 354, 355, 356, 357 and sections 360, 361, as illustrated in FIGS. 20 and 21.

As also shown in FIG. 50, the lid 2430 has a pair of blocking members 2490 that engage the posts 2474 when the cartridge 2410 is closed to keep the various loops 2480, 2482, 2484, 2486 in place. More precisely, each of the blocking members 2490 has a longitudinal portion 2492 extending along the longitudinal direction 2402, and a transverse portion 2494 extending along the transverse direction 2406. The longitudinal portions 2492 may be positioned to seat in the slots 2476 of the posts 2474 to ensure that the loops 2480, 2482, 2484, 2486 cannot slip from the posts 2474 by moving laterally toward the lid 2430, into a gap that may exist between the posts 2474 and the lid 2430. Similarly, the transverse portions 2494 may be positioned inward of and adjacent to the first and second sets of slots 2440, 2442 to ensure that the leading and trailing ends 2450, 2452 of the threaders 2412, 2414 are unable to slide out of the slots 2440, 2442 by moving laterally toward the lid 2430, into a gap that may exist between the slots 2440, 2442 and the lid 2430.

Figure 51:
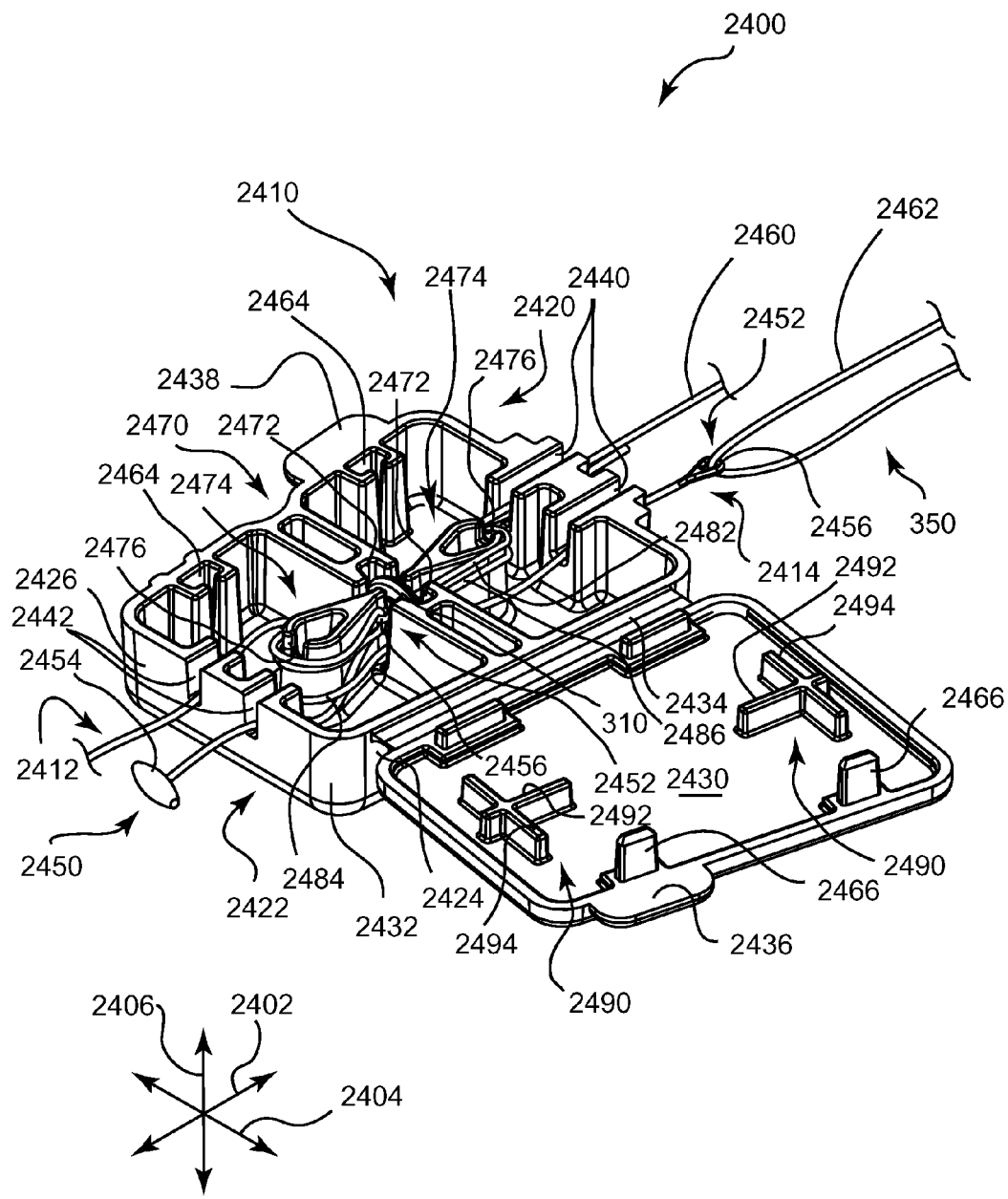
FIG. 51 is a perspective view of the system of FIG. 49, with the cartridge open and one of the sutures drawn part-way through the cartridge.

Referring to FIG. 51, a perspective view illustrates the system 2400 of FIG. 49, with the cartridge 2410 open to expose the line lock 310. In FIG. 51, the first threader 2412 is drawn partially through the cartridge 2410 so that the corresponding first suture portion 2460 of the suture 350 is partially drawn through the corresponding passageways 322, 324, 328 (not visible in FIG. 51) of the line lock 310.

More precisely, the first suture portion 2460 has been drawn through the corresponding one of the first set of slots 2420 and through the first primary passageway 322 (not visible in FIG. 51) of the line lock 310. Further, the first suture portion 2460 has been drawn along the first loop 2480 of the first threader 2412 so that the first suture portion 2460 encircles the post 2474 toward the second longitudinal side 2422, in place of the first loop 2480.

The leading, doubled-over portion of the first suture portion 2460 is thus poised to enter the first secondary passageway 324 (not visible). From the first secondary passageway 324, the first suture portion 2460 will then be drawn along the second loop 2482 of the first threader 2412, through the first working passageway 328 (not visible), and then through the corresponding one of the second set of slots 2442 in the second longitudinal end 2422. The leading, doubled-over portion of the first suture portion 2460 will then protrude from the cartridge 2410 and may easily be grasped and drawn by hand until the line lock 310 is positioned at the desired location along the length of the first suture portion 2460.

The second suture portion 2462 may be drawn through the cartridge 2410 in a similar manner, as described previously in connection with the discussion of FIG. 50. Thus, both suture portions 2460, 2462 may be drawn fully through the cartridge 2410 and through the passageways 322, 323, 324, 325, 328, 329 of the line lock 310. The suture portions 2460, 2462 may be drawn through the cartridge 2410 with the cartridge in the open configuration, as illustrated in FIG. 51, or with the cartridge 2410 in the closed configuration. If desired, part or all of the cartridge 2410 may be made translucent or transparent so that a user can easily verify proper threading without opening the cartridge 2410.

Figure 52:
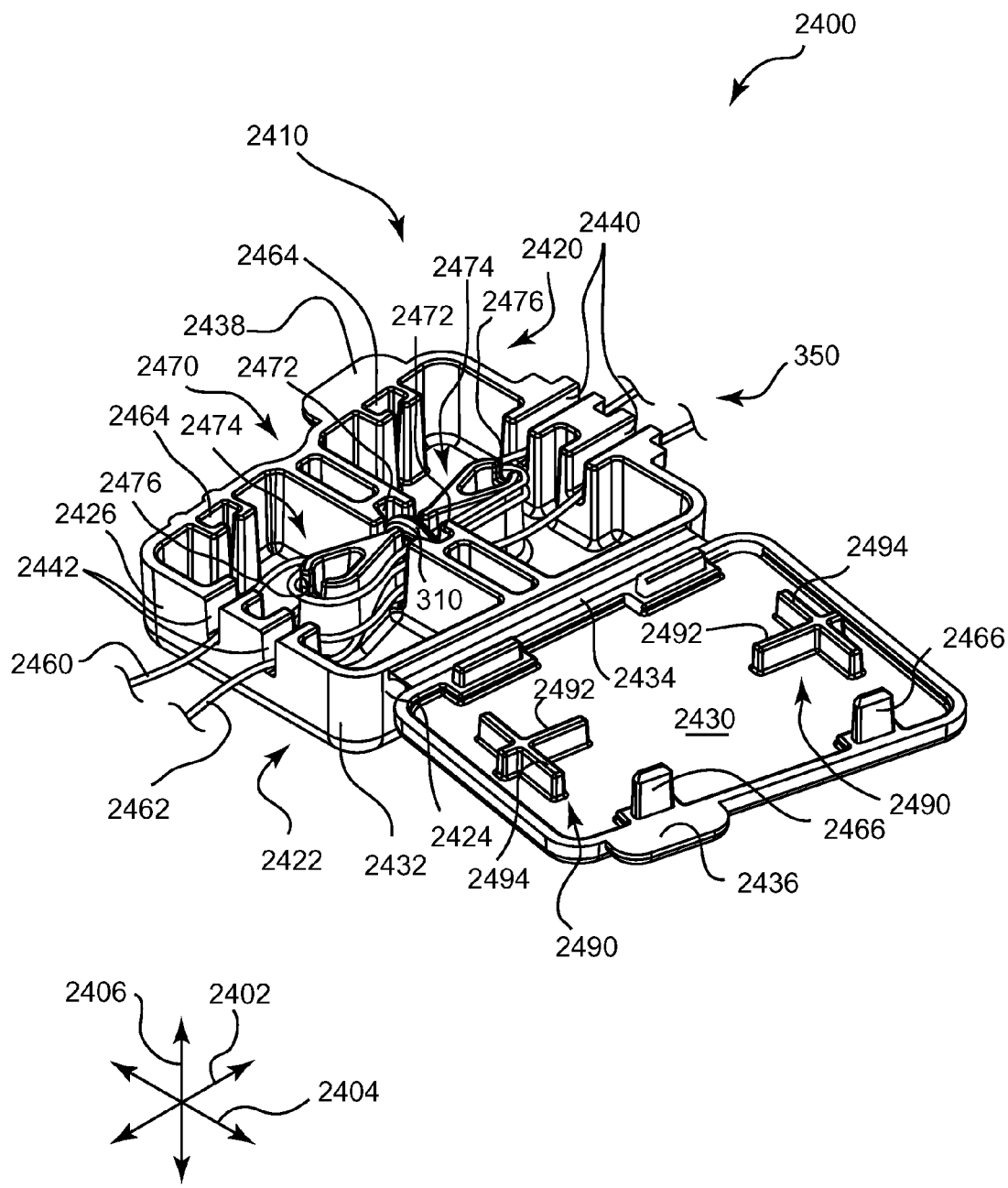
FIG. 52 is a perspective view of the system of FIG. 49, with the cartridge open and the sutures fully drawn through the cartridge to pass through the passageways of the line lock.

Referring to FIG. 52, a perspective view illustrates the system 2400 of FIG. 49, with the cartridge 2410 in the open configuration to expose the line lock 310. The suture 350 has been fully threaded through the passageways 322, 323, 324, 325, 328, 329 of the line lock 310 in the manner illustrated in FIGS. 20 and 21. Accordingly, the line lock 310 need only be removed from the cartridge 2410 prior to use to retain tissue.

Figure 53:
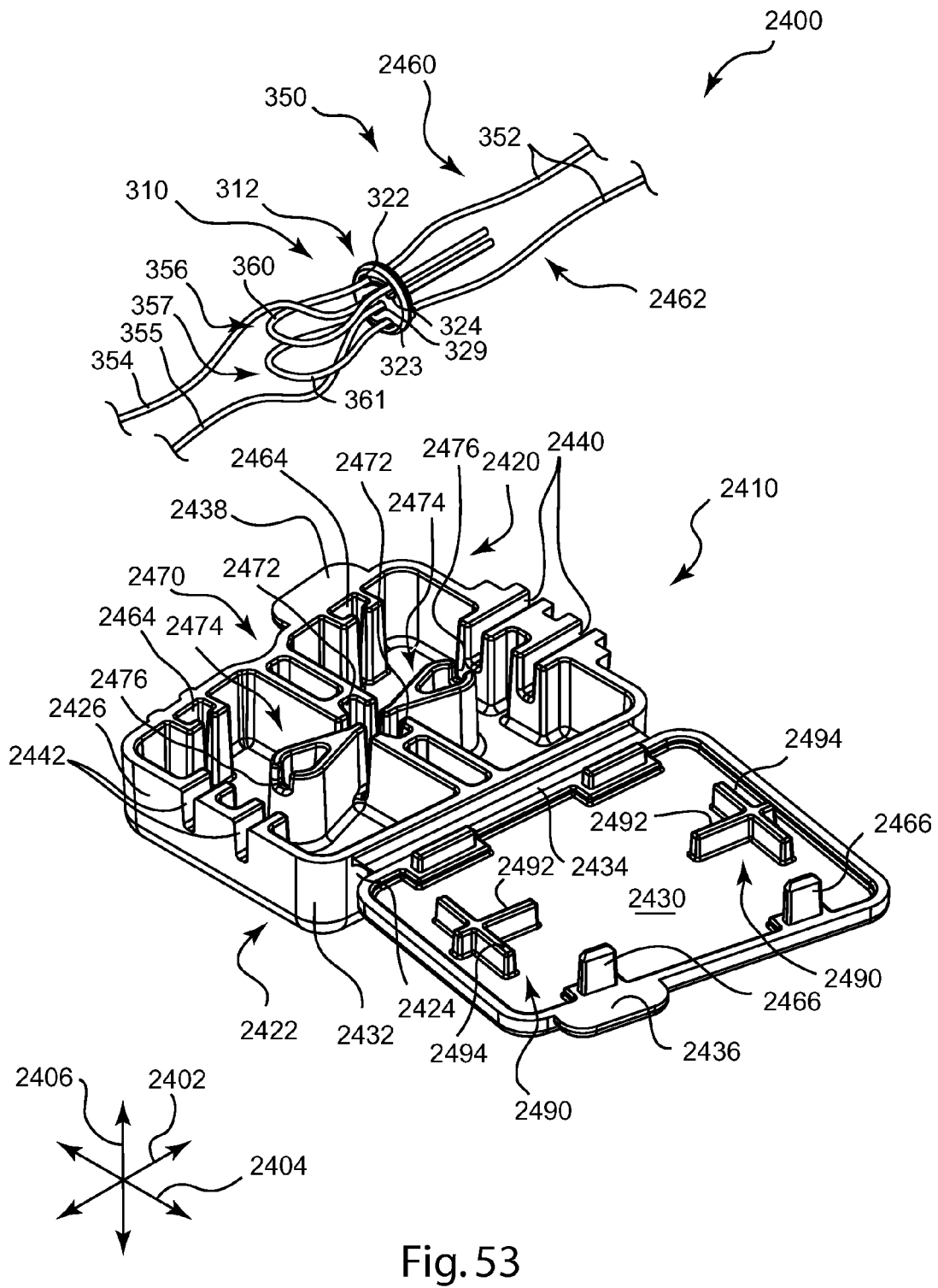
FIG. 53 is a perspective view of the system of FIG. 49, the cartridge open and the sutures and line removed from the cartridge for use.

Referring to FIG. 53, a perspective view illustrates the system 2400 of FIG. 49, with the cartridge 2410 in the open configuration, and with the line lock 310 and the suture 350 removed from the cartridge 2410 for use. The line lock 310 has been drawn from the space between the troughs 2472 by drawing the line lock 310 along the lateral direction 2404, toward the space the lid 2430 would occupy if the cartridge 2410 were closed. The first and second suture portions 2460, 2462 are also drawn along the same direction to slide free of the posts 2474 and the first and second sets of slots 2440, 2442.

As shown, the various portions and sections 352, 354, 355, 356, 357, 360, 361 of the suture 350 are arranged substantially as shown in FIGS. 20 and 21. The standing portion 352 may connect the first and second suture portions 2460, 2461 together at a location not illustrated in FIG. 53. The standing portion 352 may be inserted through an anchor embedded in tissue, or otherwise positioned behind tissues to be retained by the system 2400, prior to performance of the threading process set forth above. If the standing portion 352 is not required to pass through an enclosed aperture, the standing portion 352 may be positioned with respect to the tissue to be retained after the suture 350 has been threaded through the line lock 310.

In alternative embodiments, the first and second suture portions 2460, 2462 may be two separate lengths of suture. The first and second suture portions 2460, 2462 may then be attached to their respective anchor points, or to each other, before or after they are threaded through the line lock 310. If desired, the first and second suture portions 2460, 2462, as separate sutures, may be attached to two different anchor points and the line lock 310 may be applied to draw the anchor points, and thereby the connected tissues, together.

As another alternative, the line lock 310 may only receive a single suture portion via the cartridge 2410 and one of the threaders 2412, 2414. Such a single suture portion may be attached to an anchor at one end and tightened via the line lock 310 to retain tissue. As yet another alternative, a differently configured line lock (not shown) may be retained within the cartridge 2410 to receive a single suture portion. Such a line lock may operate as the functional equivalent of the line lock 310, and may thus have only the first passageways 322, 324, 328.

Returning to the configuration of FIG. 53, once the suture 350 has been properly threaded through the passageways 322, 323, 324, 325, 328, 329 (some of which are not visible in FIG. 53), the line lock 310 may then be used to retain the tissue as desired. This may be accomplished by following the procedures outlined previously, i.e., holding the working portions 354, 355 and advancing the line lock 310 along the suture 350 to constrict the standing portion 352, either with or without an insertion tool, and then trimming the suture 350.

Thus, the suture 350 may easily be threaded through the line lock 310 in the proper pattern to ensure that the line lock 310 is able to perform as desired. Threading may be performed without significantly compromising the sterility of the line lock 310, the suture 350, or the operating environment. Thus, the convenience, reliability, and safety of tissue retention operations may be enhanced through the present invention.

Figure 54:
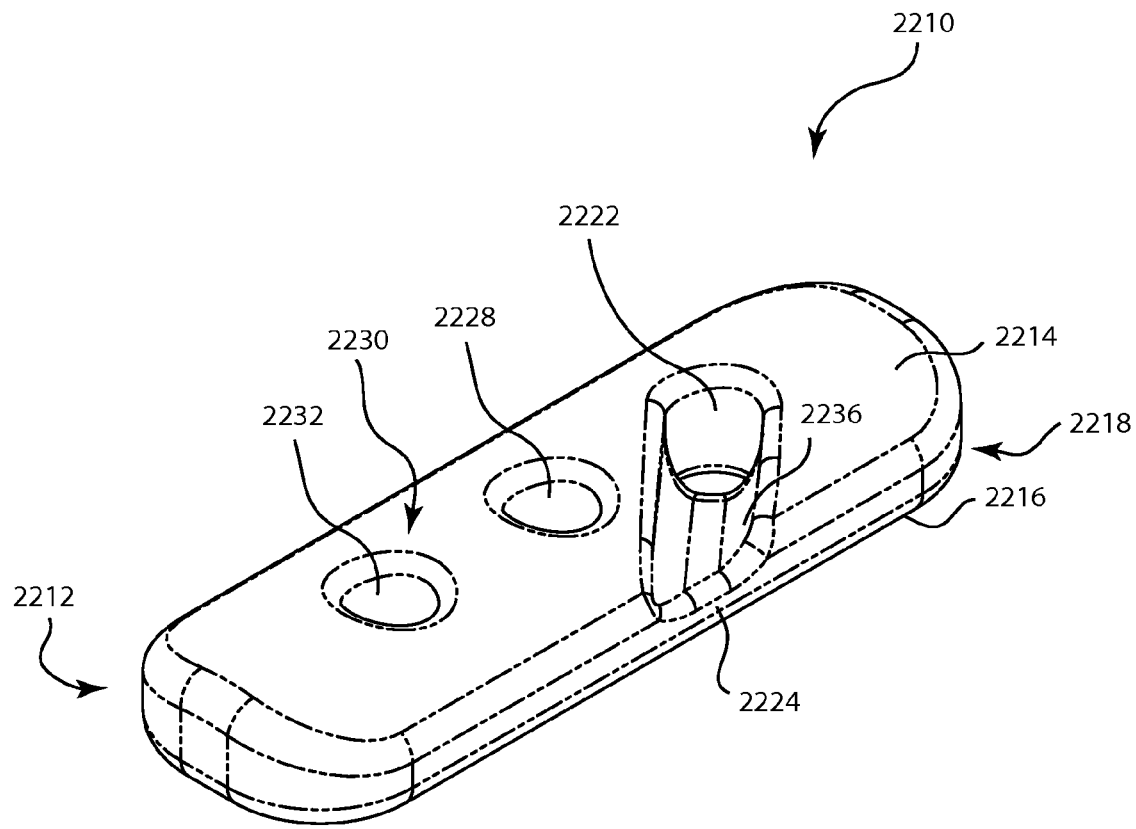
FIG. 54 is a perspective view of a line lock according to another embodiment of the invention.

And as previously described in U.S. application Ser. No. 11/001,866, referring to FIG. 54, a perspective view illustrates a line lock 2210 according to one alternative embodiment of the invention. The line lock 2210 has a body 2212 with a generally rectangular shape, with a top surface 2214, a bottom surface 2216, and a periphery 2218 that separates the top surface 2214 from the bottom surface 2216. The body 2212 fully bounds a primary passageway 2222 and partially bounds a secondary passageway 2224. In the embodiment of FIG. 54, the secondary passageway 2224 is defined by a portion of the periphery 2218 of the body 2212.

The body 2212 also fully bounds a working passageway 2228 and a retention passageway 2230. The retention passageway 2230 has a bore 2232 positioned to retain one end of a suture (not shown in FIG. 54). The body 2212 further defines a groove 2236 extending between the primary and secondary passageways 2222, 2224. The operation of the various passageways 2222, 2224, 2228, 2230 and the groove 2236 will be described in connection with FIGS. 55 and 56.

Figure 55:
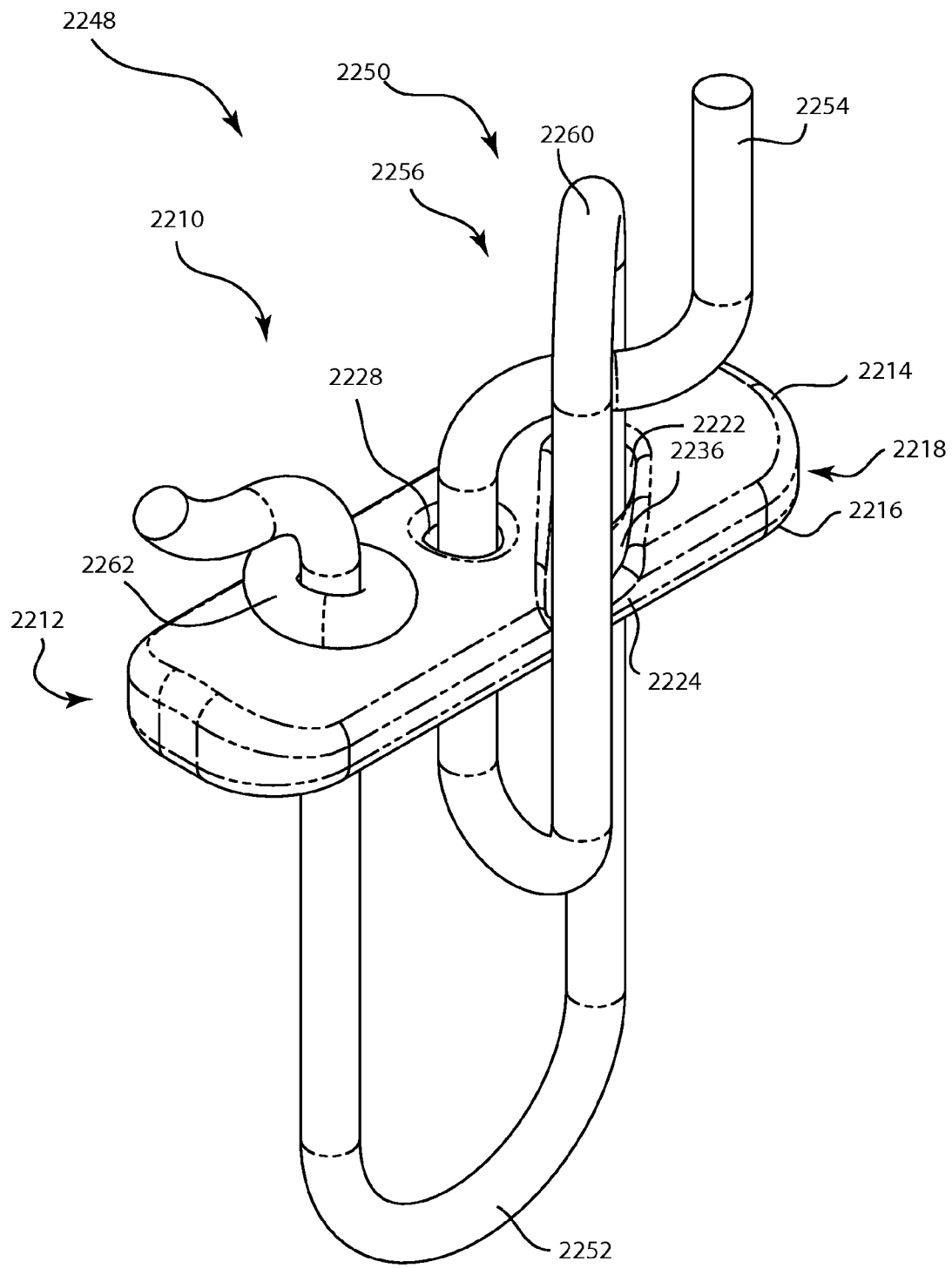
FIG. 55 is a perspective view of the line lock of FIG. 54, with a suture threaded loosely therethrough

Referring to FIG. 55, a perspective view illustrates a system 2248 including the line lock 210 of FIG. 54 and a line, or a suture 2250, that may be locked by the line lock 2210. The suture 2250 is relatively loosely routed through the passageways 2222, 2224, 2228 so that slack is present in the suture 2250.

As shown, the suture 2250 has a standing portion 2252 that may be looped through or around the tissue to be retained. A working portion 2254 may be manipulated by a surgeon to control the slack in the standing portion 2252. A locking portion 2256 separates the working portion 2254 from the standing portion 2252 and passes through the passageways 2222, 2224, 2228 in the manner illustrated. The locking portion 2256 includes a compression section 2260 that compresses the working portion 2254 against the body 2212 when the suture 2250 is tightened to prevent motion of the working portion 2254 through the working passageway 2228.

As shown, the end of the suture 2250 adjacent to the standing portion 2252 is secured to the line lock 2210 via a knot 2262. More precisely, the end of the suture 2250 has been inserted through the bore 2232 of the retention passageway 2230 (not visible in FIG. 55), and then the knot 2262 has been tied in the end. The knot 2262 may be a simple overhand knot. The knot 2262 is too large to pass through the bore 2232; thus, the end of the suture 2250 is effectively secured to the line lock 2210.

In this application, the word "secured," with reference to a flexible member, means that some part of the flexible member is connected to an object so as to be inseparable from the object by tension on the flexible member in at least one direction. Thus, even though the knot 2262 may be withdrawn from the top surface 2214, the fact that the knot 2262 is unable to pass through the top surface 2214 causes the end of the suture 2250 to be "secured" to the line lock 2210. The term "direction," when used in connection with motion of a flexible member such as a line, does not necessarily refer to a static vector. Rather, a "direction" may refer to motion of the line along a pathway, toward one specified end of the pathway. Thus, stating that a line is only able to move along a pathway in one direction means that the line can only be advanced toward one end of the pathway. The line moves along the pathway in one direction even though in the course of advancement along the pathway, segments of the line will simultaneously be moving along a variety of differently-oriented vectors.

The knot 2262 may be tied and the suture 2250 may be inserted through the bore 2232 prior to commencement of the surgical procedure. For example, the knot 2262 may be tied and the suture 2250 may be inserted through the bore 2232 at a manufacturing or packaging facility, prior to packaging of the line lock 2210 for shipping. The suture 2250 may then be shipped in the same package, preassembled with the line lock 2210 and ready for use. A needle (not shown) may similarly be included in the package. Thus, the surgeon need not select and assemble the various components needed to carry out the tissue retention procedure; rather, all necessary parts are already assembled and ready for use prior to commencement of the procedure.

From the end of the locking portion 2256 adjacent to the standing portion 2252, the locking portion 2256 passes through the primary passageway 2222, and then extends generally parallel to the groove 2236 to define the compression section 2260 and reach the secondary passageway 2224. From the secondary passageway 2224, the locking portion 2256 passes through the working passageway 2228. The working portion 2254 then passes through the space between the compression section 2260 and the groove 2236.

When tension is applied to the standing portion 2252, as when the standing portion 2252 is tightened around one or more pieces of tissue, the compression section 2260 is drawn taught. The compression section 2260 presses the working portion 2254 against the groove 2236 to keep the working portion 2254 from being drawn back through the working passageway 2228.

Figure 56:
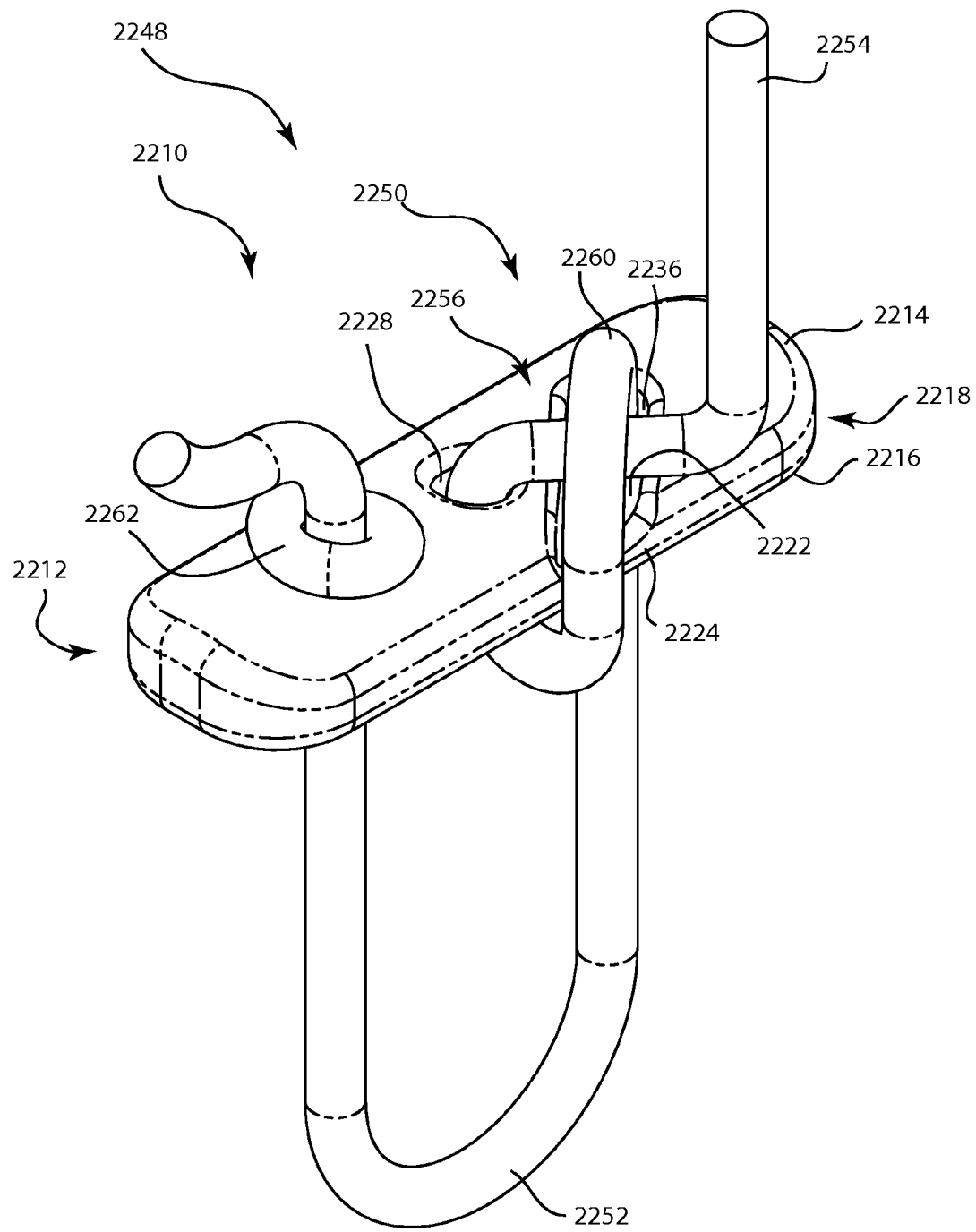
FIG. 56 is a perspective view of the line lock of FIG. 54, with a suture threaded tightly therethrough.

Referring to FIG. 56, a perspective view illustrates the system 2248, with the suture 2250 routed relatively tightly through the passageways 2222, 2224, 2228 of the line lock 2210. As described previously, the compression section 2260 presses the working portion 2254 against the groove 2236 to retain the working portion 2254. As the working portion 2254 is pressed against the groove 2236, bends (not shown) may be formed in the working portion 2254 as the working portion 2254 conforms to the shape of the groove 2236. Such bends enhance locking of the working portion 2254 because there is greater friction keeping the working portion 2254 in place, and there is no direct path along which tension on the working portion 2254 can act to draw the working portion 2254 through the space between the compression section 2260 and the groove 2236. Thus, the locking portion 2256 cooperates with the knot 2262 to retain both ends of the standing portion 2252, thereby enabling the standing portion 2252 to securely retain tissue.

Figure 57:
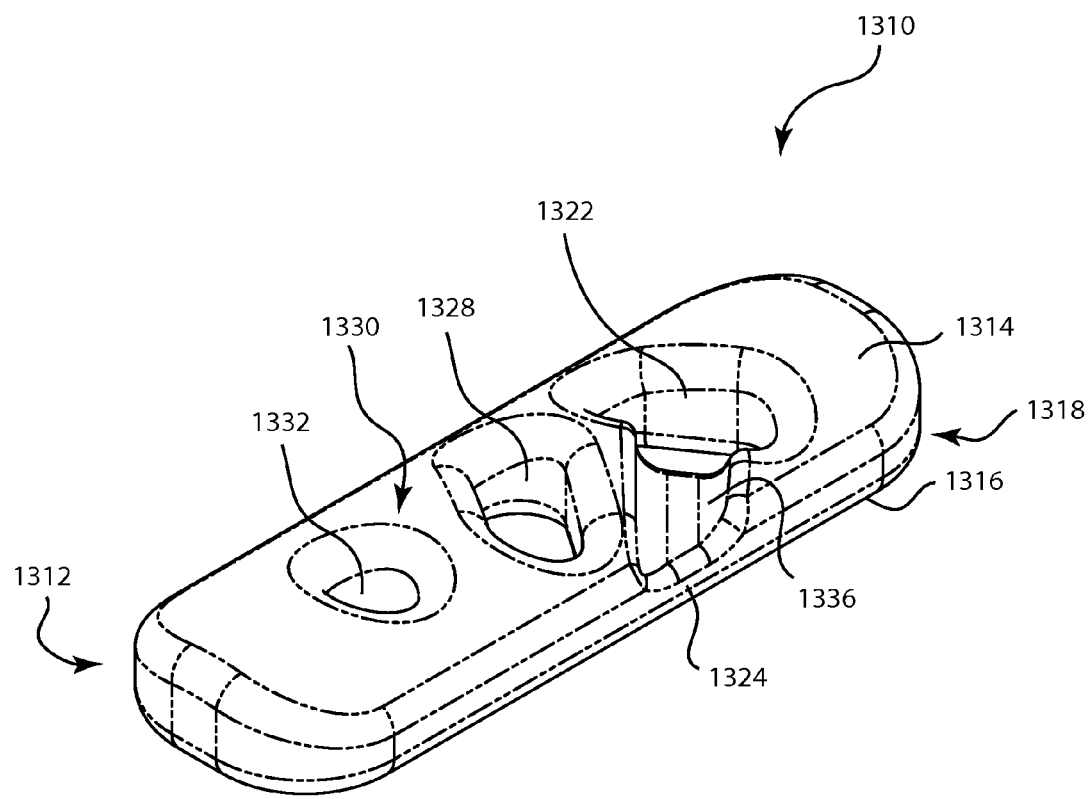
FIG. 57 is a perspective view of a line lock according to yet another embodiment of the invention.

Referring to FIG. 57, a perspective view illustrates a line lock 1310 according to another alternative embodiment of the invention. The line lock 1310 has a body 1312 with a generally rectangular shape, with a top surface 1314, a bottom surface 1316, and a periphery 1318 that separates the top surface 1314 from the bottom surface 1316. The body 1312 fully bounds a primary passageway 1322 and partially bounds a secondary passageway 1324. As in the previous embodiment, the secondary passageway 1324 is defined by a portion of the periphery 1318 of the body 1312.

The body 1312 also fully bounds a working passageway 1328 and a retention passageway 1330. The retention passageway 1330 has a bore 1332 positioned to retain a loop of a suture (not shown in FIG. 57). The body 1312 further defines a groove extending between the primary and secondary passageways 1322, 1324. The primary passageway 1322, the working passageway 1328, and the groove 1336 may all be somewhat wider than their counterparts of the previous embodiment to permit two suture portions to be simultaneously routed therethrough. The operation of the various passageways 1322, 1324, 1328, 1330 and the groove 1336 will be described in connection with FIGS. 58 and 59.

Figure 58:
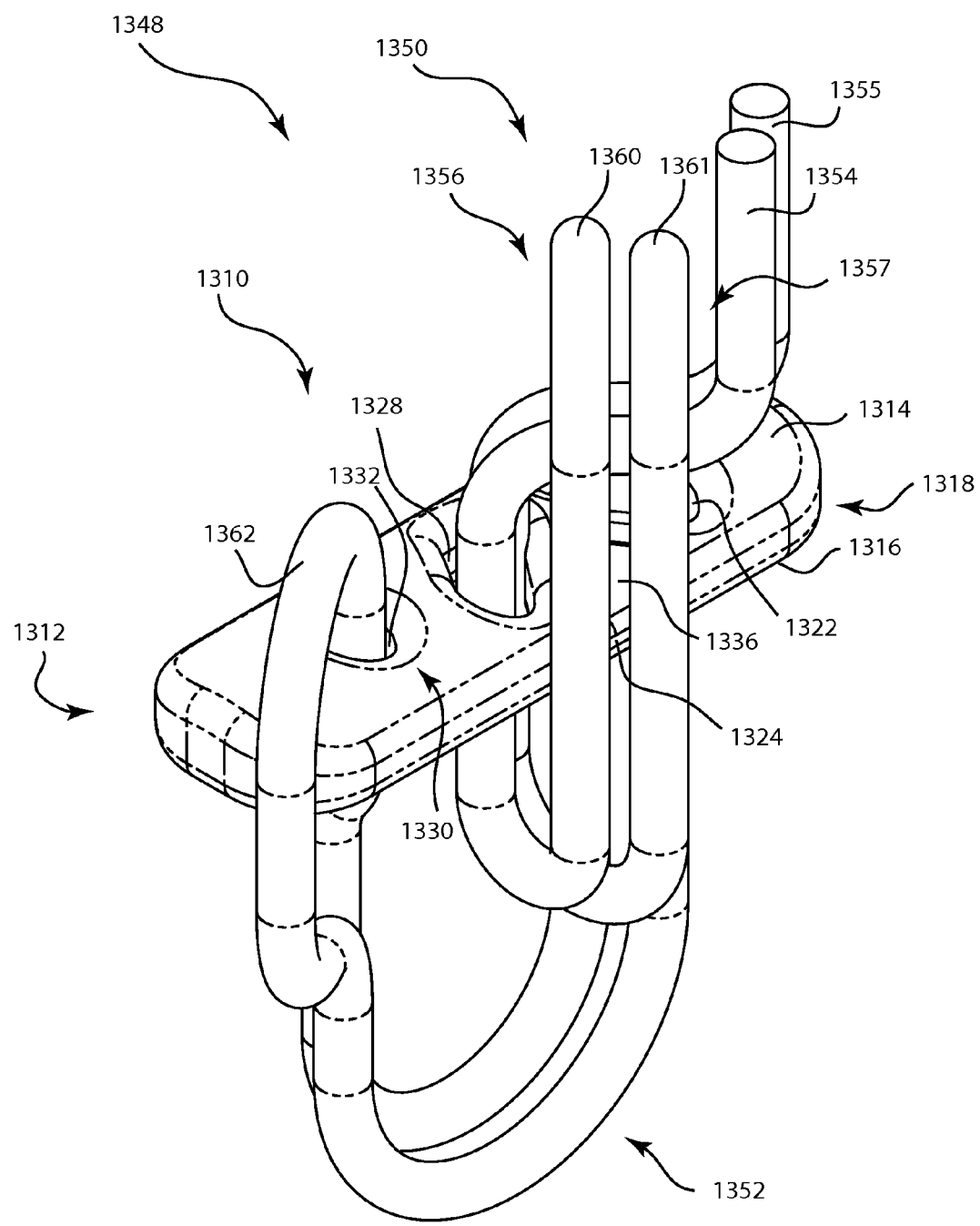
FIG. 58 is a perspective view of the line lock of FIG. 57, with the suture threaded loosely therethrough.

Referring to FIG. 58, a perspective view illustrates a system 1348 including the line lock 1310 of FIG. 57 and a line, or a suture 1350, which may be locked by the line lock 1310. The suture 1350 is relatively loosely routed through the passageways 1322, 1324, 1328 so that slack is present in the suture 1350.

As shown, the suture 1350 has a standing portion 1352 with two separate strands, each of which may be looped through or around the tissue to be retained. First and second working portions 1354, 1355 may be manipulated by a surgeon to control the slack in the standing portion 1352. First and second locking portions 1356, 1357, respectively, separate the first and second working portions 1354, 1355, respectively, from the standing portion 1352. The locking portions 1356, 1357 pass through the passageways 1322, 1324, 1328 side-by-side, in the manner illustrated.

The first locking portion 1356 includes a first compression section 1360 that compresses the first and second working portions 1354, 1355 against the body 1312 when the suture 1350 is tightened to prevent motion of the first working portion 1354 through the working passageway 1328. Similarly, the second locking portion 1357 includes a second compression section 1361 that compresses the first and second working portions 1354, 1355 against the body 1312 when the suture 1350 is tightened to prevent motion of the second working portion 1355 through the working passageway 1328.

The suture 1350 also has a loop 1362 that passes through the bore 1332 of the retention passageway 1330. The loop 1362 effectively secures the two strands of the working portion 1352 to the line lock 1310, just as the knot 2262 of the previous embodiment secured the single strand of the working portion 2252 to the line lock 2210. As with the knot 2262, the loop 1362 may be inserted through the bore 1332 prior to commencement of the surgical procedure. For example, the loop 1362 may be inserted through the bore 1332 at a manufacturing or packaging facility, prior to packaging of the line lock 1310 for shipping such that the suture 1350 is shipped pre-attached to the line lock 1310. A needle (not shown) may similarly be included in the package.

The first and second locking portions 1356, 1357 extend along a pathway similar to that followed by the locking portion 2256 of the previous embodiment. Accordingly, when the standing portion 1352 is drawn taught, the first and second compression sections 1360, 1361 press the first and second working portions 1354, 1355 against the groove 1336 to keep the working portions 1354, 1355 from moving back through the working passageway 1328.

Figure 59:
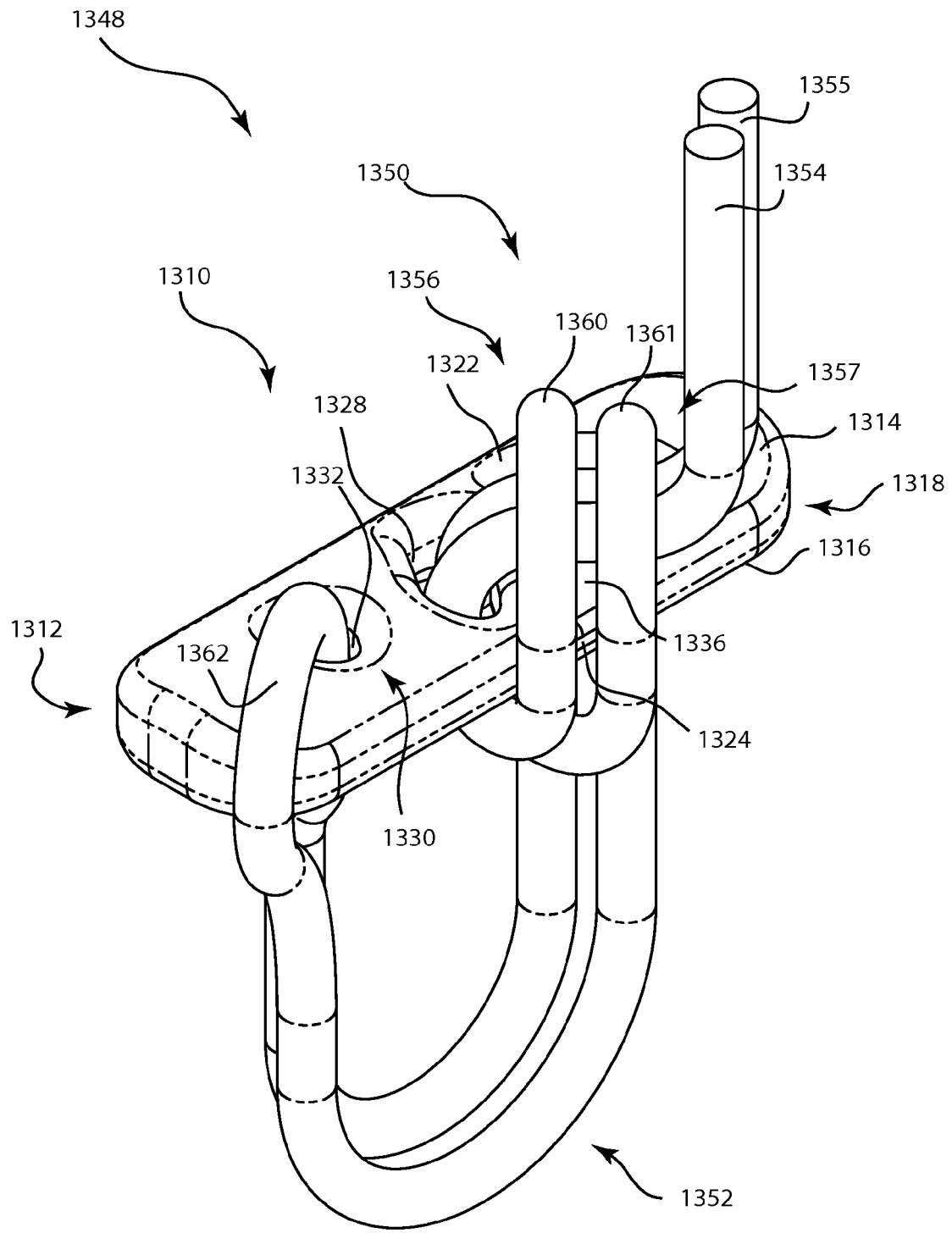
FIG. 59 is a perspective view of the line lock of FIG. 57, with the suture threaded tightly therethrough.

Referring to FIG. 59, a perspective view illustrates the system 1348, with the suture 1350 routed relatively tightly through the passageways 1322, 1324, 1328 of the line lock 1310. As described previously, the compression sections 1360, 1361 press the working portions 1354, 1355 against the groove 1336 to retain the working portions 1354, 1355. Bends (not shown) may be formed in the working portions 1354, 1355 as the working portions 1354, 1355 conform to the shape of the groove 1336 to enhance locking of the working portions 1354, 1355. Thus, the locking portions 1356, 1357 cooperate with the loop 1362 to retain both ends of the standing portion 1352, thereby enabling the standing portion 1352 to securely retain tissue.

As mentioned previously, it may be desirable to package the line lock 190 in a cartridge that facilitates threading of the line 100 through the passageways 158, 160, 162. One example of such a cartridge is illustrated in FIGS. 60 through 64, and is shown with respect to the line lock 190 of FIGS. 14A and 14B. However, those of skill in the art will recognize that a similar cartridge may be provided for a line lock according to any other embodiment of the invention, such as the line locks 2210, 1310 of FIGS. 54-59.

Figure 60:
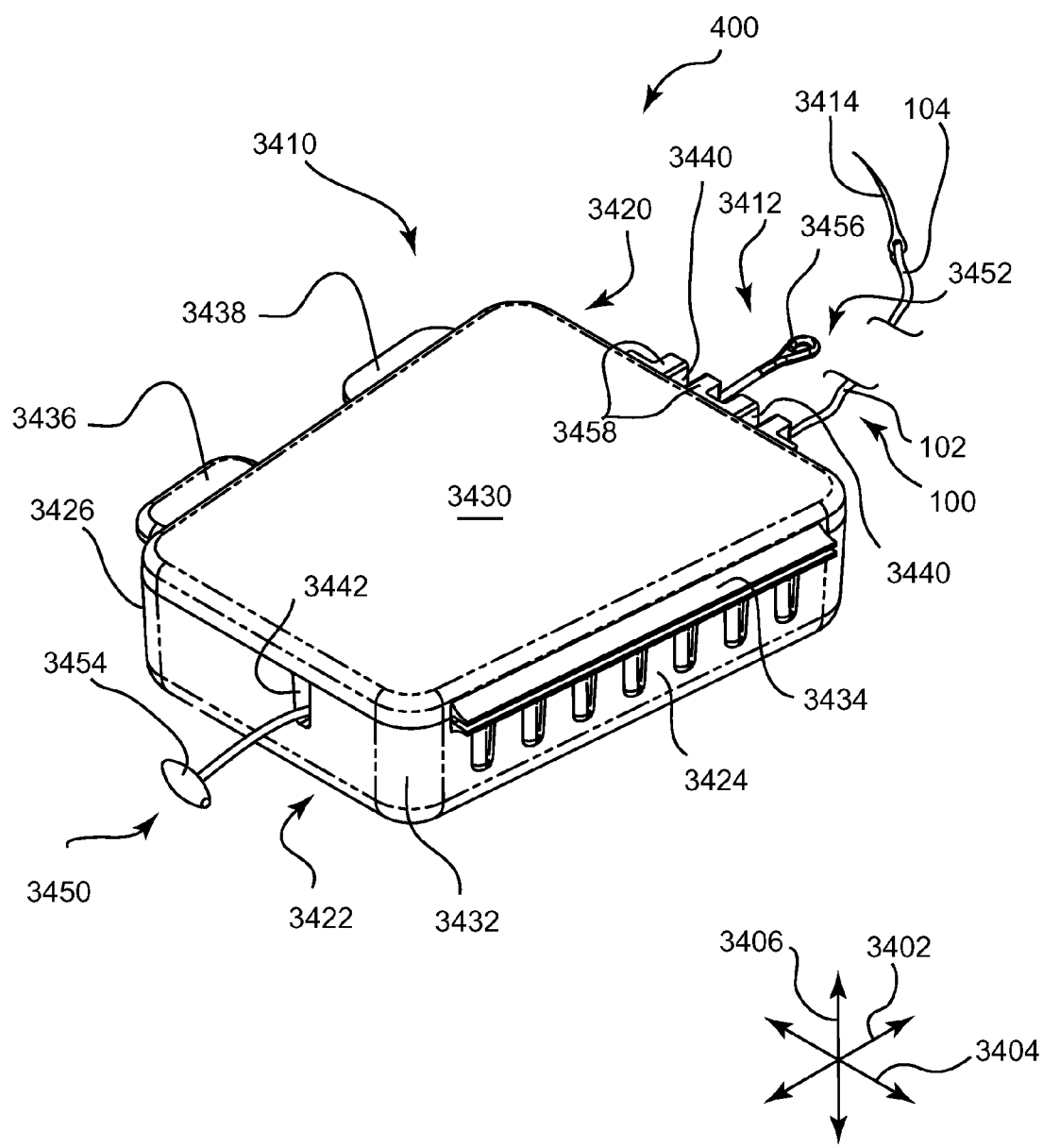
FIG. 60 is a perspective view of a system including a cartridge with a threader that facilitates the insertion of the pre-attached suture through the passageways of the line lock of FIGS. 14A and 14B.

Referring to FIG. 60, a perspective view illustrates one embodiment of a system 400 including the line lock 190 of FIGS. 14A and 14B (not visible in FIG. 60), and various implements to help insert, or "thread," the line 100 through the 158, 160, 162 of the line lock 190. A longitudinal direction 3402, a lateral direction 3404, and a transverse direction 3406 cooperate to form a system of orthogonal axes that will be used for reference in the following description.

In addition to the line lock 190, the system 3400 includes a cartridge 3410, a threader 3412, and a needle 3414. The cartridge 3410 contains the line lock 190 and, when in the closed configuration shown in FIG. 60, substantially encloses the line lock 190 to facilitate insertion of the line 100 through the passageways 158, 160, 162, and possibly, to help isolate the line lock 190 from contaminants. In this application, the phrase "substantially enclose" does not require full enclosure; rather, some portion(s) of the substantially enclosed part may protrude from the enclosure.

The cartridge 3410 may be formed of a plastic such as polypropylene, PEEK, or the like. The threader 3412 passes through the cartridge 3410 along a pathway to enable a user to draw the line 100 through the passageways 158, 160, 162 along the correct pattern, as will be described in greater detail subsequently. The threader 3412 may be formed substantially of a fibrous material or a plastic, such as nylon.

The needle 3414 is attached to the working end 104 of the line 100, for example, by knotting, ultrasonic welding, swaging, or the like. The needle 3414 may be attached to the working end 104 prior to packaging of the system 3400 for shipping. Thus, the surgeon need not locate and attach an appropriate needle to the line 100 prior to surgical use. The needle 3414 may be any of a variety types suitable for surgical use.

As shown in FIG. 60, the cartridge 3410 has a first longitudinal end 3420, a second longitudinal end 3422, a first lateral end 3424, and a second lateral end 426. The threader 3412 passes through the longitudinal ends 3420, 3422. Furthermore, the cartridge 3410 has a lid 3430 designed to move with respect to the remainder of the cartridge 3410, which will be referred to as a containment portion 3432. More specifically, a living hinge 3434 extends generally along the first lateral end 3424, between the adjacent edges of the lid 3430 and the containment portion 3432. The living hinge 3434 is integrally formed with the lid 3430 and the containment portion 3432 and flexes to enable pivotal motion of the lid 3430 with respect to the containment portion 3432. In alternative embodiments, a conventional hinge may be used, or a lid may be slidable with respect to and/or fully removable from the remainder of the cartridge, thereby obviating the need for a hinging mechanism.

A first tab 3436 integrally formed with the lid 3430 and a second tab 3438 integrally formed with the containment portion 3432 may easily be pushed in opposite directions, for example, by a user's thumbs, to open the cartridge 3410. The lid 3430 and the containment portion 3432 may be designed to adhere to each other at the second lateral end 3426 so that the cartridge 3410 only opens when a threshold force is applied. Thus, the cartridge 3410 may not open if dropped or jostled.

The first longitudinal end 3420 has a first set of slots 3440 through which the threader 3412 and the line 100 pass. More precisely, the threader 3412 passes through one slot of the first set of slots 3440. From the end 192, the standing portion 102 of the line 100 extends out of the cartridge 3410 through the other of the first set of slots 3440.

Similarly, the second longitudinal end 3422 has a slot 3442 through which the threader 3412 passes. Thus, the threader 3412 extends into the cartridge 3410 through the first longitudinal end 3420 and out again through the second longitudinal end 3422. The threader 3412 has a leading end 3450 adjacent to the second slot 3442 and a trailing end 3452 adjacent to the first set of slots 3440.

The leading end 3450 has a pull feature designed to facilitate grasping and drawing of the leading end 3450 by hand. In the embodiment of FIG. 60, the pull feature takes the form of a grip 3454 that may be easily grasped, for example, between a thumb and an index finger. The grip 3454 may be a plastic rod crimped, insert molded, adhesive bonded, or otherwise attached to the remainder of the threader 3412. In alternative embodiments, one or more differently configured pull features may be used, including rigid rings, flexible loops, spherical beads, squared beads, and the like.

Additionally, the trailing end 3452 has a suture retention feature designed to retain a portion of the line 100 to enable the threader 3412 to draw the line 100 through the passageways 158, 160, 162 of the line lock 190. In FIG. 60, the suture retention feature takes the form of an eyelet 3456, which is able to receive an end of the line 100 such that the end can double back on itself to be drawn through the cartridge 3410. The eyelet 3456 may be crimped, adhesive bonded, insert molded, or otherwise attached to the remainder of the threader 3412. In alternative embodiments, one or more differently configured suture retention features may be used, including adhesive-coated surfaces, collets, clips, flexible loops, and the like.

The eyelet 3456 may be retained to ensure that it is not drawn into the cartridge 3410 prior to attachment to the line 100. For example, the containment portion 3432 may have retention posts 3458 that extend in the longitudinal direction 3402 on either side of the slots of the first set of slots 3440 through which the threader 3412 passes. The eyelet 3456 may optionally be looped around the retention posts 3458 so that the eyelet 3456 is unable to enter the corresponding slot of the first set of slots 3440 until the eyelet 3456 is removed from around the retention posts 3458. The eyelet 3456 may need to be slightly larger than shown in FIG. 60 to enable it to encircle a pair of the retention posts 3458. The retention posts 3458 may also serve a similar function if a loop or other flexible suture retention feature is used in place of the eyelet 3456.

Figure 61:
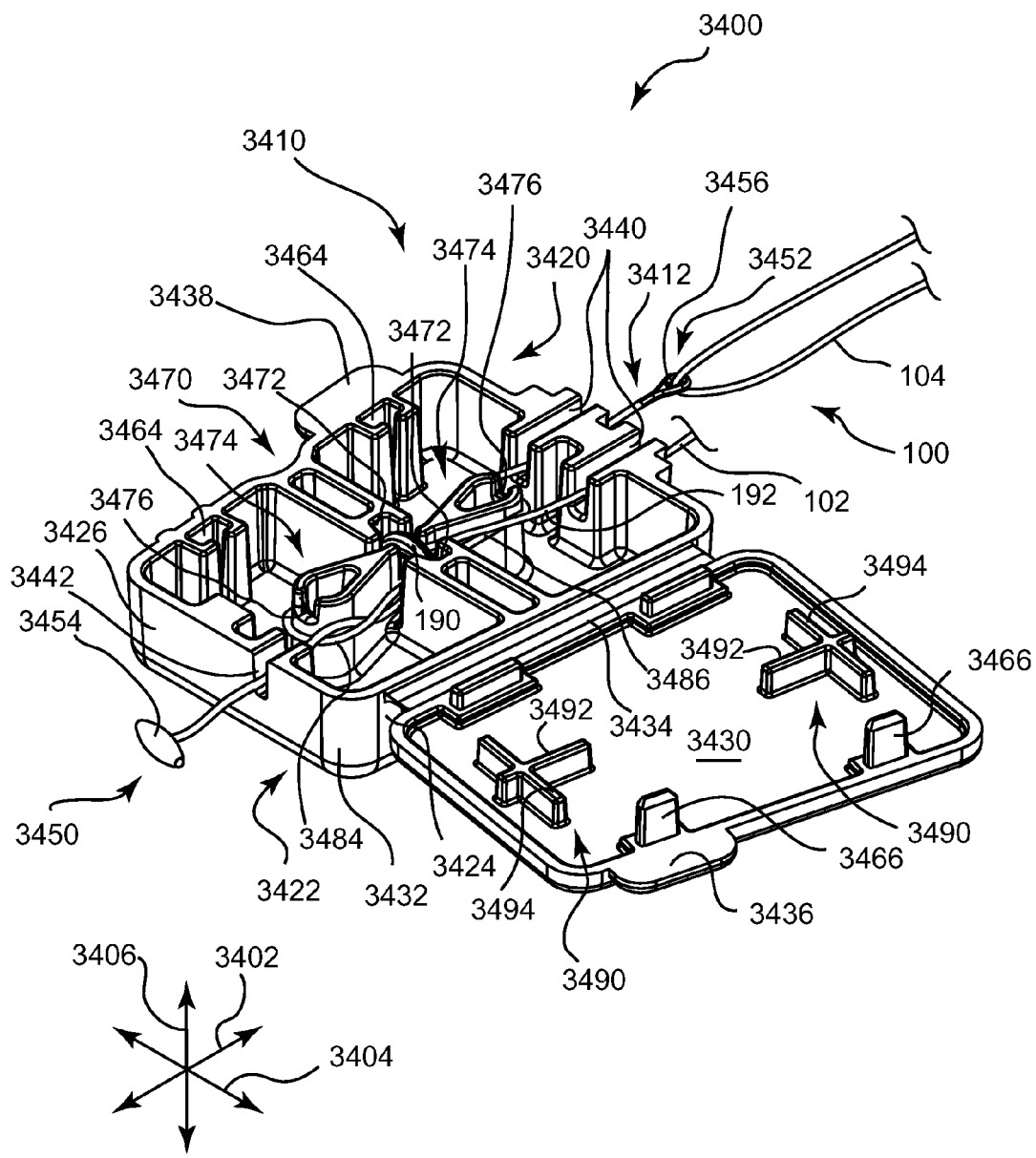
FIG. 61 is a perspective view of the system of FIG. 60, with the lid of the cartridge open and the suture coupled to the trailing end of the threader.

Referring to FIG. 61, a perspective view illustrates the system 3400 of FIG. 60, with the cartridge 3410 in the open configuration to expose the line lock 190. The line 100 has also been inserted into engagement with the trailing end 3452 of the threader 3412. More precisely, the needle 3414 and the working portion 104 have already been inserted through or around the tissue or tissues to be retained, and the needle 3414 has been removed from the working portion 104. The working portion 104 has then been inserted through the eyelet 3456 of the threader 3412. The working portion 104 is doubled back on itself to permit the eyelet 3456 to draw it through the cartridge 3410 and through the passageways 158, 160, 162 (not visible in FIG. 61) of the line lock 190.

In alternative embodiments, multiple sutures or ends may need to be inserted through passageways of a line lock, such as the line lock 1310 of FIGS. 57 through 59. A cartridge (not shown) for such an embodiment may have multiple threaders, each of which is positioned to draw one suture or one end through the corresponding passageways. Operation of such a cartridge may otherwise be similar to that of the cartridge 3410.

Returning to FIG. 61, the containment portion 3432 has a pair of sockets 3464 formed therein. Each of the sockets 3464 may provide a generally rectangular cavity surrounded by a wall that is slotted to permit expansion of the socket 3464. The lid 3430 has a pair of posts 3466 that are generally rectangular in shape, and are sized and positioned to slide into the sockets 3464 when the cartridge 3410 is in the closed configuration. The posts 3466 may be sized to fit relatively tightly into the sockets 3464 so that the cartridge 3410 does not open until the threshold force is applied to remove the posts 3466 from the sockets 3464.

The containment portion 3432 also has a central divider 3470 that extends generally along the lateral direction 3404 to effectively separate the containment portion 3432 into two separate compartments. The containment portion 3432 defines a retention feature designed to retain the line lock 190. In this application, the terms "retention feature" and "threading feature" are to be broadly interpreted to include, not just single structural elements, but also groups of elements that cooperate to carry out line lock retention or suture threading.

In FIG. 61, the retention feature takes the form of a pair of troughs 3472 positioned on either side of a space in which the line lock 190 rests within the containment portion 3432. The troughs 3472 face each other such that they retain the line lock 190 to resist motion of the line lock 190 along the longitudinal and transverse directions 3402, 3406. The troughs 3472 are exposed on the open side of the containment portion 3432 so that the line lock 190 can be inserted into the space between the troughs 3472, or removed therefrom, by moving the line lock 190 along the transverse direction 3406.

Additionally, the containment portion 432 has a threading feature designed to help guide the line 100 through the passageways 158, 160, 162 along the desired pattern. In FIG. 61, the threading feature takes the form of a pair of posts 3474 positioned on either side of the central divider 3470, and thus on either side of the space in which the line lock 190 rests. Each of the posts 3474 may have a generally teardrop-shaped cross section, as taken through a plane parallel to the longitudinal and transverse directions 3402, 3406. Each of the posts 3474 also has a slot 3476 facing the adjacent one of the first and second longitudinal ends 3420, 3422.

The threader 3412 is wrapped around the posts 3474 along a configuration similar to that provided by the line 100 illustrated in FIGS. 14A and 14B. More precisely, from its trailing end 3452, the threader 3412 passes through one of the first set of slots 3440, then through the primary passageway 158 (not visible in FIG. 61) and then through the secondary passageway 160 (not visible) to define a first loop 3484 of the threader 3412. From the secondary passageway 160, the threader 3412 passes through the working passageway 162 (not visible) to define a second loop 3486 of the first threader 3412. From the working passageway 162, the threader 3412 extends through the first loop 3484 and then passes through the second slot 3442, to the leading end 3450.

The various portions of the threader 3412 may be positioned to correspond to portions of the line 100, as labeled in FIGS. 14A and 14B. For example, the trailing end 3452 may correspond to the standing portion 102 of the line 100, the leading end 3450 may correspond to the working portion 104, and the loops 3484, 3486 may correspond to the locking portion 106. The first loop 3484 of the threader 3412 may more precisely correspond to the compression section 110 of the locking portions 106. Accordingly, when the line 100 is drawn through the passageways 158, 160, 162 by the threader 3412, the line 100 assumes a configuration having the various portions 102, 104, 106, as illustrated in FIGS. 14A and 14B.

As also shown in FIG. 61, the lid 3430 has a pair of blocking members 3490 that engage the posts 3474 when the cartridge 3410 is closed to keep the first and second loops 3484, 3486 in place. More precisely, each of the blocking members 3490 has a longitudinal portion 3492 extending along the longitudinal direction 3402, and a transverse portion 3494 extending along the transverse direction 3406. The longitudinal portions 3492 may be positioned to seat in the slots 3476 of the posts 3474 to ensure that the loops 3484, 3486 cannot slip from the posts 3474 by moving laterally toward the lid 3430, into a gap that may exist between the posts 3474 and the lid 3430. Similarly, the transverse portions 3494 may be positioned inward of and adjacent to the first set of slots 3440 and to the second slot 3442 to ensure that the leading and trailing ends 3450, 3452 of the threader 3412 are unable to slide out of the slots 3440, 3442 by moving laterally toward the lid 3430, into a gap that may exist between the slots 3440, 3442 and the lid 3430.

Figure 62:
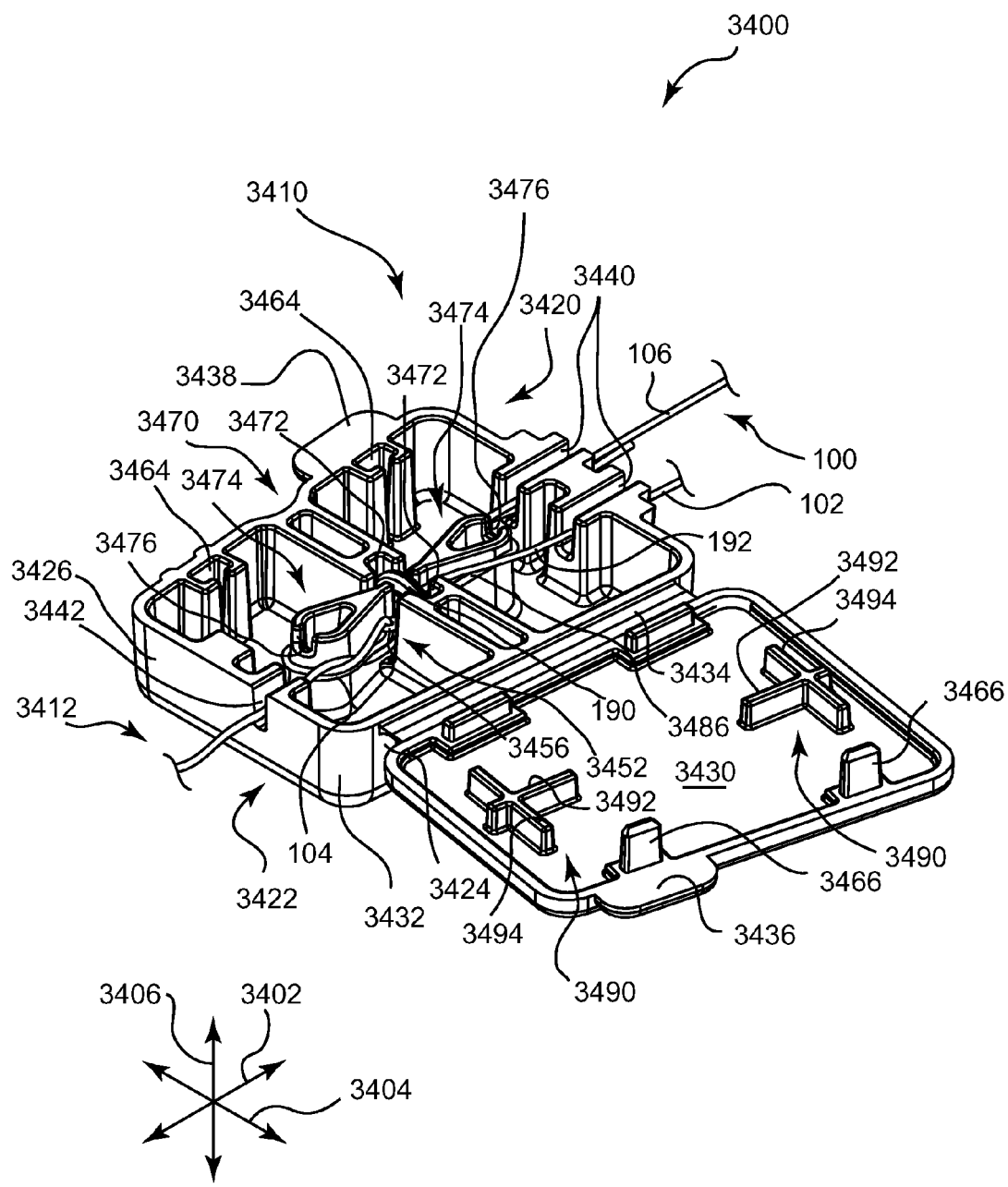
FIG. 62 is a perspective view of the system of FIG. 60, with the cartridge open and the suture drawn part-way through the cartridge.

Referring to FIG. 62, a perspective view illustrates the system 3400 of FIG. 62, with the cartridge 3410 open to expose the line lock 190. In FIG. 62, the threader 3412 is drawn partially through the cartridge 3410 so that the working portion 104 of the line 100 is drawn partially along the pathway followed by the threader 3412. More precisely, the working portion 104 has been drawn through the corresponding one of the first set of slots 3420 and through the primary passageway 158 (not visible in FIG. 62) of the line lock 190. Further, the working portion 104 has been drawn along the first loop 3484 of the threader 3412 so that the working portion 104 encircles the post 3474 toward the second longitudinal side 3422, in place of the first loop 3484.

The leading, doubled-over portion of the working portion 104 is thus poised to enter the secondary passageway 160 (not visible). From the secondary passageway 160, the working portion 104 will then be drawn along the second loop 3486 of the threader 3412, through the working passageway 162 (not visible), and then through the second slot 3442 in the second longitudinal end 3422. The leading, doubled-over portion of the working portion 104 will then protrude from the cartridge 3410 and may easily be grasped and drawn by hand until the line lock 190 is positioned at the desired location along the length of the line 100.

The line 100 may be drawn through the cartridge 3410 with the cartridge in the open configuration, as illustrated in FIG. 62, or with the cartridge 3410 in the closed configuration. If desired, part or all of the cartridge 3410 may be made translucent or transparent so that a user can easily verify proper threading without opening the cartridge 3410.

Figure 63:
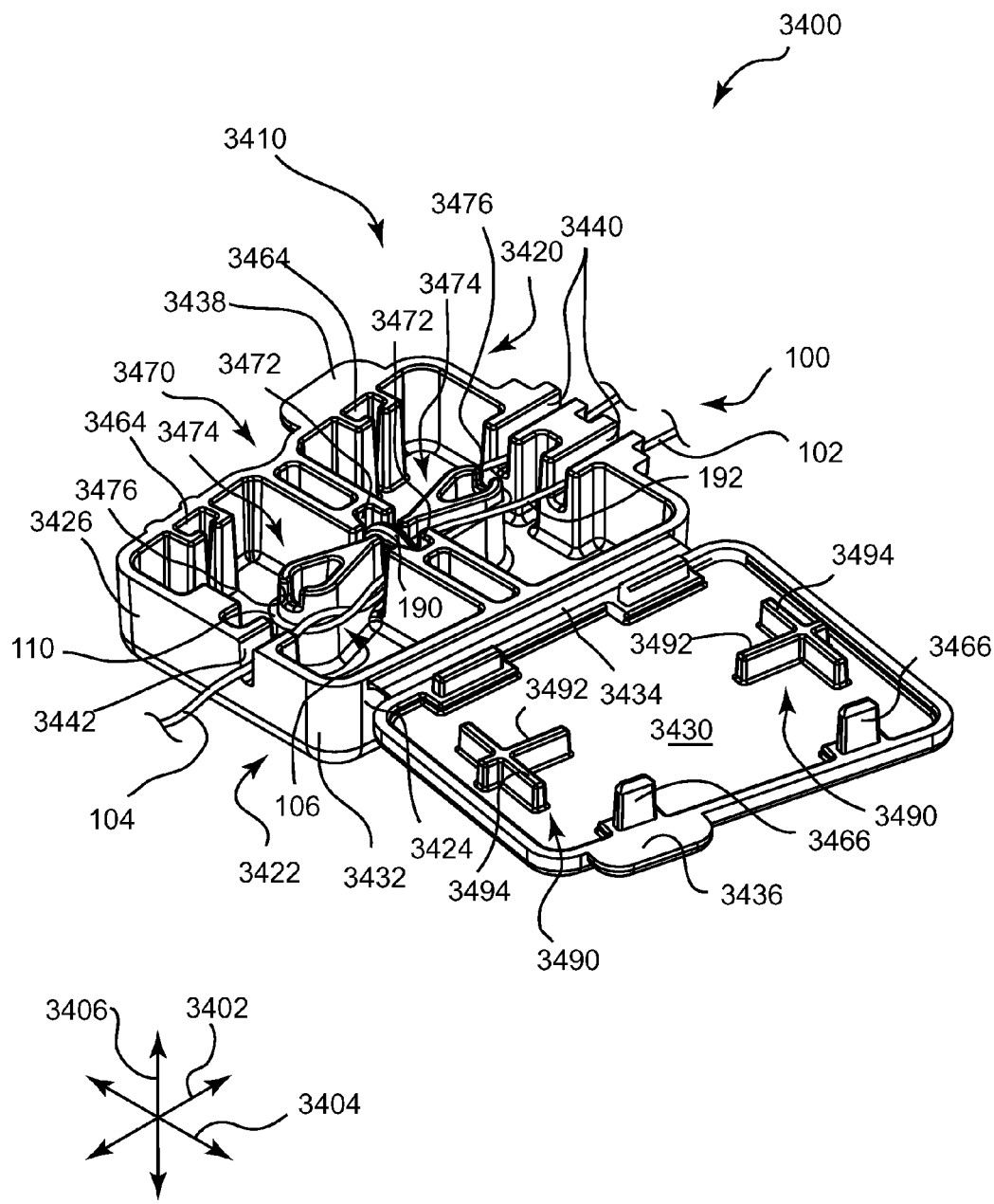
FIG. 63 is a perspective view of the system of FIG. 60, with the cartridge open and the suture fully drawn through the cartridge to pass through the passageways of the line lock.

Referring to FIG. 63, a perspective view illustrates the system 3400 of FIG. 60, with the cartridge 3410 in the open configuration to expose the line lock 190. The line 100 has been fully threaded through the passageways 158, 160, 162 of the line lock 190 in the manner illustrated in FIGS. 14A and 14B. Accordingly, the line lock 190 need only be removed from the cartridge 3410 prior to use to retain tissue.

Figure 64:
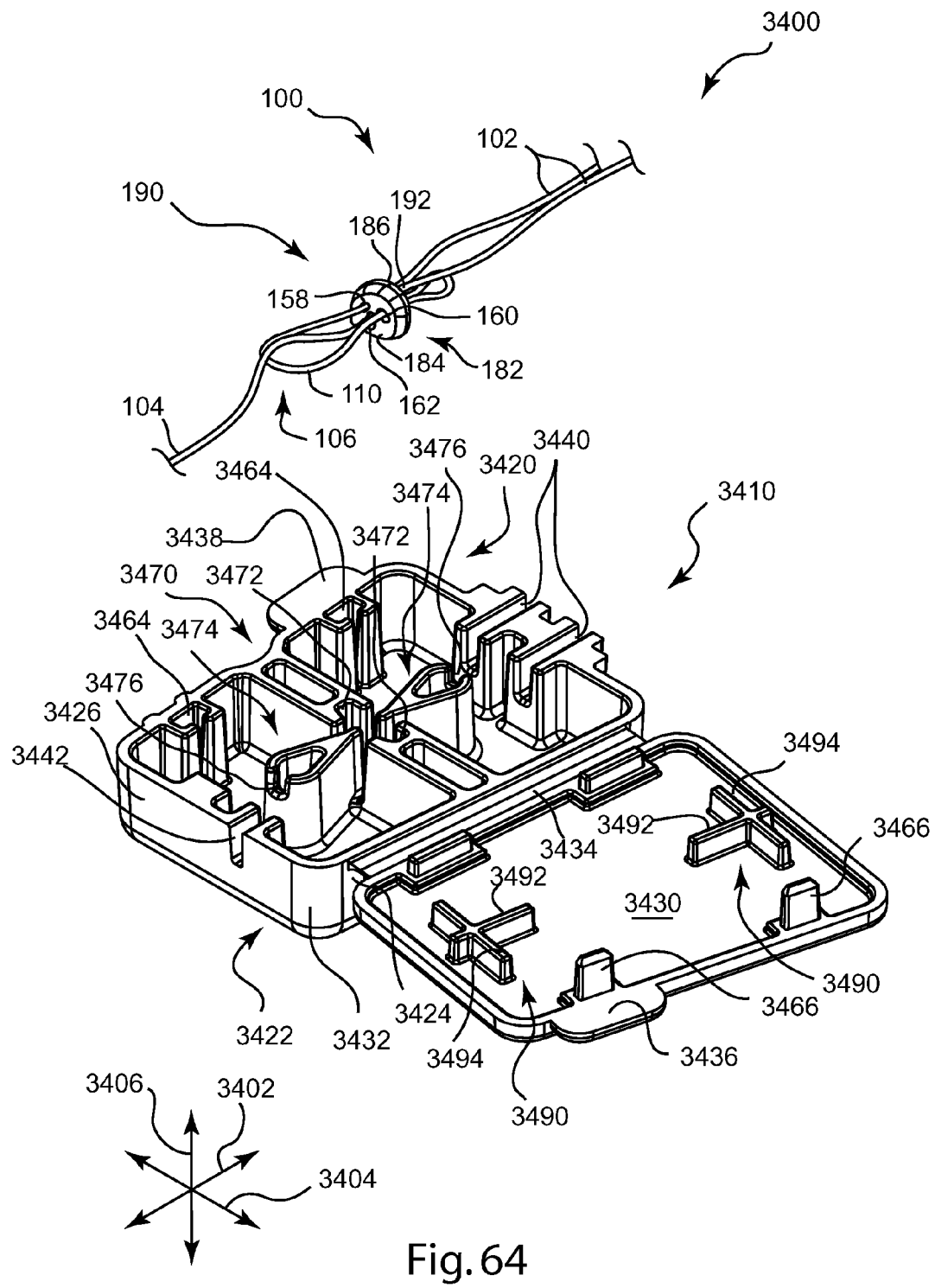
FIG. 64 is a perspective view of the system of FIG. 60, with the cartridge open and the suture and line lock removed from the cartridge for use.

Referring to FIG. 64, a perspective view illustrates the system 3400 of FIG. 60, with the cartridge 3410 in the open configuration, and with the line lock 190 and the line 100 removed from the cartridge 3410 for use. The line lock 190 has been drawn from the space between the troughs 3472 by drawing the line lock 190 along the transverse direction 3406, toward the space the lid 3430 would occupy if the cartridge 3410 were closed. The line 100 is also drawn along the same direction to slide free of the posts 3474 and the slots 3440, 3442.

As shown, the various portions and sections 102, 104, 106, 110 of the line 100 are arranged substantially as shown in FIGS. 14A and 14B. The standing portion 102 may be inserted through an anchor embedded in tissue, or otherwise positioned behind tissues to be retained by the system 400, prior to performance of the threading process set forth above. If the standing portion 102 is not required to pass through an enclosed aperture, the standing portion 102 may be positioned with respect to the tissue to be retained after the line 100 has been threaded through the line lock 190.

Once the line 100 has been properly threaded through the passageways 158, 160, 162, the line lock 190 may then be used to retain the tissue as desired. This may be accomplished by following the procedures outlined previously, i.e., holding the working portion 104 and advancing the line lock 190 along the line 100 to constrict the standing portion 102, either with or without an insertion tool, and then trimming the line 100 to the desired length.

Thus, the line 100 may easily be threaded through the line lock 190 in the proper pattern to ensure that the line lock 190 is able to perform as desired. Threading may be performed without significantly compromising the sterility of the line lock 190, the line 100, or the operating environment. Thus, the convenience, reliability, and safety of tissue retention operations may be enhanced through the present invention.

According to one alternative embodiment of the invention, one end of a suture may be removably or permanently secured to a line lock, and the other end may be received by a plurality of passageways in such a manner that the second end is only able to move through the passageways along one direction. The first end may be secured to the line lock via insert molding, knotting, ultrasonic welding, adhesive bonding, or the like. The passageways that receive the second end may be arranged in a manner similar to any of those described in the embodiments set forth above, or equivalents thereof.

The present invention has particular relevance to surgery, and more particularly to tissue retention through the use of sutures. However, the principles, structures, and methods of the present invention may also be extended to other fields, including the use of larger line locks for locking ropes or cables in a wide variety of applications.

While the present invention has application to any need for securing a line, it is particularly advantages to surgical suture applications as a way to conveniently and reliable replace the need to tie suture knots. The advantage is even greater in arthroscopic and endoscopic applications, where sophisticated sliding knots followed by "back-up" knots must be tied outside of a cannula and slid into final position at an internal body site. The sophisticated sliding knots are difficult to tie, time consuming, and bulky. The present invention provides an easy to apply, quick to deliver, and low profile solution that will reliably maintain the desired suture tension.

The present invention may be embodied in other specific forms without departing from its spirit or essential characteristics. For example, above are described various alternative examples of different adjustable line locks. It is appreciated that various features of the line locks can be mixed and matched to form a variety of other alternatives, a different threading system according to the invention. As such the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system comprising:
   a line, wherein the line comprises a standing portion, a working portion, and a locking portion between the standing and working portions, wherein the locking portion comprises a compression section and a compressed section; and a line lock, wherein the line lock comprises a body, a primary passageway, and a working passageway, wherein the line lock comprises a hollow chamber at least partially bounded within the body, wherein the body comprises a top wall and an opposing bottom wall, wherein the primary and working passageways extend through the bottom wall to communicate with the chamber;

wherein the locking portion is routed through the primary and working passageways so that the compressed section is disposed between the compression section and the body, such that the line slides through the line lock in response to tension on the line in a first direction so that the working portion lengthens and the standing portion shortens, and such that the line passively locks in response to tension on the line in a second direction, wherein the second direction is opposite the first direction, wherein the compression section biases the compressed section against the body in response to tension on the line in the second direction.

2. The system of claim 1,
wherein the body comprises a top surface and an opposing bottom surface, wherein the primary and working passageways extend through the body between the top and bottom surfaces.

3. The system of claim 2,
wherein the locking portion is routed sequentially up through the primary passageway from the bottom surface to the top surface, down from the top surface to the bottom surface, up through the working passageway from the bottom surface to the top surface, and between the compression section and the body.

4. The system of claim 3,
wherein the line lock comprises a secondary passageway, wherein the secondary passageway extends through the body between the top and bottom surfaces.

5. The system of claim 4,
wherein the locking portion is routed down from the top surface to the bottom surface through the secondary passageway.

6. The system of claim 5,
wherein the compression section extends between the primary and secondary passageways.

7. The system of claim 2,
wherein the line lock comprises a secondary passageway, wherein the secondary passageway extends through the body between the top and bottom surfaces;
wherein the locking portion is routed consecutively up through the secondary passageway from the bottom surface to the top surface, down through the primary passageway from the top surface to the bottom surface, up through the working passageway from the bottom surface to the top surface, and between the compression section and the body.

8. The system of claim 1,
wherein the locking portion is routed sequentially up through the primary passageway from the bottom wall into the chamber, out of the chamber and down to the bottom wall, up through the working passageway from the bottom wall into the chamber, and between the compression section and the body.

9. The system of claim 8,
wherein the body comprises a side wall extending between the top and bottom walls;
wherein the line lock comprises a secondary passageway, wherein the secondary passageway extends through the side wall to communicate with the chamber.

10. The system of claim 9,
wherein the locking portion is routed out of the chamber through the secondary passageway and down to the bottom wall.

11. The system of claim 10,
wherein the compression section extends between the primary and secondary passageways.

12. The system of claim 1,
wherein the body comprises a side wall extending between the top and bottom walls;
wherein the line lock comprises a secondary passageway, wherein the secondary passageway extends through the side wall to communicate with the chamber;
wherein the locking portion is routed sequentially through the secondary passageway from the side wall into the chamber, out of the chamber and down to the bottom wall, up through the working passageway from the bottom wall into the chamber, and between the compression section and the body.

13. A system comprising:
a line, wherein the line comprises a standing portion, a working portion, and a locking portion between the standing and working portions, wherein the locking portion comprises a compression section and a compressed section; and a line lock, wherein the line lock comprises a body, a primary passageway, and a working passageway, wherein the working passageway comprises a constricted capture slot;

wherein the locking portion is routed through the primary and working passageways so that the compressed section is disposed between the compression section and the body, such that the line slides through the line lock in response to tension on the line in a first direction so that the working portion lengthens and the standing portion shortens, and such that the line frictionally locks in response to tension on the line in a second direction, wherein the second direction is opposite the first direction, wherein the compression section biases the compressed section against the body in response to tension on the line in the second direction, wherein the compression section forces the compressed section into wedged frictional engagement in the capture slot in response to tension on the line in the second direction.

14. The system of claim 13,
wherein the body comprises a top surface and an opposing bottom surface, wherein the primary and working passageways extend through the body between the top and bottom surfaces.

15. The system of claim 14,
wherein the line lock comprises a sharp working corner where the working passageway extends through the top surface, wherein the compression section biases the compressed section into frictional engagement against the sharp working corner in response to tension on the line in the second direction.

16. The system of claim 14,
wherein the line lock comprises a sharp primary corner where the primary passageway extends through the top surface, wherein the line frictionally engages the sharp primary corner in response to tension on the line in the second direction.

17. The system of claim 16,
wherein the line lock comprises a secondary passageway, wherein the secondary passageway extends through the body between the top and bottom surfaces;
wherein the line lock comprises a sharp secondary corner where the secondary passageway extends through the top surface, wherein the line frictionally engages the sharp secondary corner in response to tension on the line in the second direction;
wherein the line lock comprises a generously rounded secondary corner where the secondary passageway extends through the bottom surface, wherein the line slides easily over the generously rounded secondary corner in response to tension on the line in the first direction.

18. The system of claim 14,
wherein the line lock comprises a generously rounded working corner where the working passageway extends through the bottom surface, wherein the line slides easily over the generously rounded working corner in response to tension on the line in the first direction.

19. A system comprising:
a line, wherein the line comprises a standing portion, a working portion, and a locking portion between the standing and working portions, wherein the locking portion comprises a compression section and a compressed section; and
a line lock, wherein the line lock comprises a body, a primary passageway, and a working passageway, wherein the line lock comprises a hollow chamber at least partially bounded within the body, wherein the body comprises a top wall and an opposing bottom wall, wherein the primary and working passageways extend through the bottom wall to communicate with the chamber;
wherein the locking portion is routed through the primary and working passageways so that the compressed section is disposed between the compression section and the body, such that the line slides through the line lock in response to tension pulling the line in a first direction tending to remove slack from the standing portion, and such that the line passively locks in response to tension pulling the line in a second direction, wherein the second direction is opposite the first direction, wherein the compression section biases the compressed section against the body in response to tension on the line in the second direction.

20. The system of claim 19,
wherein the body comprises a top surface and an opposing bottom surface, wherein the primary and working passageways extend through the body between the top and bottom surfaces.

21. The system of claim 20,
wherein the locking portion is routed sequentially up through the primary passageway from the bottom surface to the top surface, down from the top surface to the bottom surface, up through the working passageway from the bottom surface to the top surface, and between the compression section and the body.

22. The system of claim 21,
wherein the line lock comprises a secondary passageway, wherein the secondary passageway extends through the body between the top and bottom surfaces, wherein the locking portion is routed down from the top surface to the bottom surface through the secondary passageway.

23. The system of claim 19,
wherein the locking portion is routed sequentially up through the primary passageway from the bottom wall into the chamber, out of the chamber and down to the bottom wall, up through the working passageway from the bottom wall into the chamber, and between the compression section and the body.

24. The system of claim 23,
wherein the body comprises a side wall extending between the top and bottom walls;
wherein the line lock comprises a secondary passageway, wherein the secondary passageway extends through the side wall to communicate with the chamber;
wherein the locking portion is routed out of the chamber through the secondary passageway and down to the bottom wall.

\* \* \* \* \*